(12) United States Patent
Lopez

(10) Patent No.: US 7,038,029 B2
(45) Date of Patent: May 2, 2006

(54) IMMUNOSTIMULATORY OLIGONUCLEOTIDES AND USES THEREOF

(75) Inventor: Ricardo Agustin Lopez, Autonama de Buenos Aires (AR)

(73) Assignee: Immunotech S.A., Ciudad Autonoma de Buenos Aires (AR)

( * ) Notice: Subject to any disclaimer, the term of this patent is extended or adjusted under 35 U.S.C. 154(b) by 118 days.

(21) Appl. No.: 10/309,775

(22) Filed: Dec. 4, 2002

(65) Prior Publication Data

US 2004/0006032 A1 Jan. 8, 2004

(30) Foreign Application Priority Data

May 30, 2002 (CA) ............................................. 2388049

(51) Int. Cl.
*C07H 21/00* (2006.01)
*A61K 39/00* (2006.01)

(52) U.S. Cl. .................................. 536/23.1; 424/184.1
(58) Field of Classification Search ................ 536/23.1; 424/184.1
See application file for complete search history.

(56) References Cited

U.S. PATENT DOCUMENTS

| | | | |
|---|---|---|---|
| 5,663,153 A | 9/1997 | Hutcherson et al. | 514/44 |
| 5,723,335 A | 3/1998 | Hutcherson et al. | 435/375 |
| 5,968,909 A | 10/1999 | Agrawal et al. | 514/44 |
| 6,090,791 A | 7/2000 | Sato et al. | |
| 6,194,388 B1 | 2/2001 | Krieg et al. | 514/44 |
| 6,207,646 B1 | 3/2001 | Krieg et al. | 514/44 |
| 6,214,806 B1 | 4/2001 | Krieg et al. | 514/44 |
| 6,218,371 B1 * | 4/2001 | Krieg et al. | 514/44 |
| 6,225,292 B1 | 5/2001 | Raz et al. | 514/44 |
| 6,239,116 B1 | 5/2001 | Krieg et al. | 514/44 |
| 6,339,068 B1 | 1/2002 | Krieg et al. | 514/44 |
| 6,406,705 B1 | 6/2002 | Davis et al. | 424/278.1 |
| 6,429,199 B1 | 8/2002 | Krieg et al. | 514/44 |
| 6,455,689 B1 | 9/2002 | Schlingensiepen et al. | |
| 6,653,292 B1 * | 11/2003 | Krieg et al. | 514/44 |
| 2001/0044416 A1 | 11/2001 | McCluskie et al. | |
| 2002/0137714 A1 | 9/2002 | Kandimalla et al. | |
| 2002/0156033 A1 | 10/2002 | Bratzler et al. | |
| 2002/0165178 A1 | 11/2002 | Schetter et al. | |
| 2002/0198165 A1 | 12/2002 | Bratzler et al. | |
| 2003/0040499 A1 | 2/2003 | Schlingensiepen et al. | |
| 2003/0050268 A1 | 3/2003 | Krieg et al. | |

FOREIGN PATENT DOCUMENTS

| | | |
|---|---|---|
| WO | 0468520 | 1/1992 |
| WO | WO 94/25588 A2 | 11/1994 |
| WO | WO 95/26204 | 10/1995 |
| WO | WO 96/02555 | 2/1996 |
| WO | WO 98/40100 | 9/1998 |
| WO | WO 98/52962 | 11/1998 |
| WO | WO 99/33488 | 7/1999 |
| WO | WO 99/56755 A1 | 11/1999 |
| WO | WO 99/62923 A2 | 12/1999 |
| WO | WO 00/14217 A2 | 3/2000 |
| WO | WO 00/61151 A2 | 10/2000 |
| WO | 00/62800 | 10/2000 |
| WO | 00/62802 | 10/2000 |
| WO | WO 00/67023 A1 * | 11/2000 |
| WO | WO 00/67787 A2 | 11/2000 |
| WO | 00/75304 | 12/2000 |
| WO | WO 01/00231 | 1/2001 |
| WO | WO 01/00232 | 1/2001 |
| WO | WO 01/02007 A1 | 1/2001 |
| WO | WO 01/07055 A1 | 2/2001 |
| WO | 01/12804 | 2/2001 |
| WO | WO-01/22972 | 4/2001 |
| WO | WO 01/22972 A2 | 4/2001 |
| WO | WO-01/22990 | 4/2001 |
| WO | WO 01/22990 A2 | 4/2001 |
| WO | 01/32877 | 5/2001 |
| WO | WO 01/48018 A1 | 7/2001 |

(Continued)

OTHER PUBLICATIONS

Dias Neto et al. Shotgun sequencing of the human transcriptome with ORF expressed sequence tags, PNAS USA, 2000, 97(7):3491–3496.*

Liang et al. Activation of Human B cells by Phosphorothioate Oligodeoxynucleotides, Journal of Clinical Investigation, 1996, 98(5):1119–1129.*

Johan Bylund, et al., "Immunostimulatory DNA induces degranulation and NADPH–oxidase activation in human neutrophils while concomitantly inhibiting chemotaxis and phagocytosis", Eur. J. Immunol. 2002, 32:2847–2856.

Ekambar R. Kandimalla, et al., "Effect of Chemical Modifications of Cytosine and Guanine in a CpG–Motif of Oligonucleotides: Structure–Immunostimulatory Activity Relationships", Bioorganic & Medicinal Chemistry, 9(2001) 807–813.

(Continued)

*Primary Examiner*—James Housel
*Assistant Examiner*—Stacy B. Chen
(74) *Attorney, Agent, or Firm*—Darby & Darby

(57) ABSTRACT

Oligonucleotides containing the non-palindromic sequence motif:

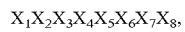

$X_1X_2X_3X_4X_5X_6X_7X_8$, wherein $X_1$ is C,T,G or A (preferably T or C); wherein $X_2$ is C,T,G or A; wherein $X_7$ is C,T,G or A (preferably G); at least three, and preferably all, of $X_3$, $X_4$, $X_5$, $X_6$ and $X_8$ are T; and with the proviso that, in the motif, a C does not precede a G (in other terms, the nucleic acid motif does not consist of a CpG oligonucleotide), that modulate the immune response of animals of the order Primate, including humans, are disclosed. This immune modulation is characterized by stimulation of proliferation, differentiation, cytokine production and antibody production on B-cells and cell differentiation on plasmacytoid dendritic cells.

11 Claims, 23 Drawing Sheets

FOREIGN PATENT DOCUMENTS

| WO | 01/51083 | 7/2001 |
|---|---|---|
| WO | WO 01/55341 A2 | 8/2001 |
| WO | 01/55370 | 8/2001 |
| WO | WO 01/62909 A1 | 8/2001 |
| WO | WO 01/62910 A1 | 8/2001 |
| WO | WO 01/68077 A2 | 9/2001 |
| WO | WO 01/68116 A2 | 9/2001 |
| WO | WO 01/68143 A2 | 9/2001 |
| WO | WO 01/68144 A2 | 9/2001 |
| WO | 01/68673 | 9/2001 |
| WO | 01/83503 | 11/2001 |
| WO | WO 01/93905 A1 | 12/2001 |
| WO | 02/16549 | 2/2002 |
| WO | 02/26757 | 4/2002 |
| WO | 02/32454 | 4/2002 |
| WO | WO 02/056909 A2 | 7/2002 |
| WO | WO 02/069369 A2 | 9/2002 |
| WO | WO 02/095027 A2 | 11/2002 |
| WO | WO 02/102825 A2 | 12/2002 |
| WO | PCT/EP 03/05691 | of 2003 |
| WO | WO 03/002065 A2 | 1/2003 |

OTHER PUBLICATIONS

Roland Lang, et al., "Guanosine–rich oligodeoxynucleotides induce proliferation of macrophage progenitors in cultures of murine bone marrow cells", Eur. J. Immunol., 1999, 29:3496–3506.

David K. Monteith, et al., "Immune stimulation–a class effect of phosphorothioate oligodeoxynucleotides in rodents", Anti–Cancer Drug Design (1997), 12:421–432.

M. Oumouna, et al., "Activation of nonspecific cytotoxic cells (NCC) with synthetic oligodeoxynucleotides and bacterial genomic DNA: Binding, specificity and identification of unique immunostimulatory motifs", Developmental and Comparative Immunology, 26 (2002) 257–269.

Qiuyan Zhao, et al., "Effect of Different Chemically Modified Oligodeoxynucleotides on Immune Stimulation", Biochemical Pharmacology, vol. 51, (1996), pp. 173–182.

Alexander H. Dalpke, et al., "Phosphodiester CpG oligonucleotides as adjuvants: polyguanosine runs enhance cellular uptake and improve immunostimulative activity of phosphodiester CpG oligonucleotides in vitro and in vivo", Immunology (2002) 106:102–112.

Michael J. McCluskie, "The potential of oligodeoxynucleotides as mucosal and parenteral adjuvants", Vaccine, 19 (2001) 2657–2660.

Paola Parronchi, et al., "Phosphorothioate Oligodeoxynucleotides Promote the In Vitro Development of Human Allergen–Specific CD4+ T Cells into Th1 Effectors", The Journal of Immunology, 1999, 163:5946–5953.

Vollmer, J., et al., "Highly Immunostimulatory CpG–Free Oligodeoxynucleotides for Activiation of Human Leukocytes", Antisense & Nucleic Acid Drug Development, 12:165–175 (2002).

Coley Pharmaceutical Group, Inc., www.clinicaltrials.gov, Linking patients to medical research "Trastuzumab Plus CpG 7909 in Treating Women With Metastatic Breat Cancer That Has Not Responded to Previous Trastuzumab and Chemotherapy", (2002).

Coley Pharmaceutical Group, Inc., www.clinicaltrials.gov, Linking patients to medical research "Continuation Study of CpG 7909 in Patients with Stable Disease or Who Have Responded to Therapy for their Malignancies", (2002).

Coley Pharmaceutical Group, Inc., www.clinicaltrials.gov, Linking patients to medical research "Phase I/II Open Label Multi–Center Study of CpG 7909 in Patients with Stage IV Renal Cell Cancer", (2002).

The Albert B. Sabine Vaccine Institute, Proceeding of the Second Annual Walker's Cay Colloguium on Cancer Vaccines and Immunotherapy, Mar. 9–10, 2000. pp. 1–80.

Gunther Hartmann et al., "Mechanism and Function of a Newly Identified CpG DNA Motif in Human Primary B Cells1", The Journal of Immunology, Jan. 2000, vol. 164 No. 2, pp. 944–952.

Sabrina Mariotti, et al., "Immunogenicity of anti–Haemophilus influenzae type b CRM 197 cojugate following mucosal vaccination with oligodeoxynucleotide containing immunostimulatory sequences as adjuvant", Vaccine, May 2002, vol. 20 No. 17–18, pp. 2229–2239.

G. Van Nest et al., "An Immunostimulatory Oligonucleotide (ISS ODN) Enhances Immune Responses to HBV Vaccine in a Variety of Animal Species Including Primates", Annual ICAC Abstracts, Sep. 1999, vol. 39, p. 374.

Juan M. Rodriguez et al., "Potent (non–CpG) immunostimulatory Oligonucleotides", FASEB Journal, Apr. 2003, vol. 17, No. 7, p. C289, XP0008029386, Abstract.

Fernanda Elias, et al., "Strong Cytosine–Guanosine–Independent Immunostimulation in Humans and Other Primates by Synthetic Oligonucleotides with PyNTTTTGT Motifs", The Journal of Immunology, Oct. 2003, vol. 171, No. 7, pp. 3697–3704.

Angier, N., "Microbe DNA Seen as Alien By Immune Cells," New York Times, Apr. 11, 1995.

Azad, R.F., et al., "Antiviral Activity of a Phosphorothioate Oligonucleotide Complementary to RNA of the Human Cytomegalovirus Major Immediate–Early Region", Antimicrobial Agents and Chemotherapy, 37: 1945–1954, Sep. 1993.

Azuma, "Biochemical and Immunological Studies on Cellular Components of Tubercle Bacilli," Kekkaku, Feb. 1998;73(2):65–70.

Ballas ZK, Rasmussen WL, Krieg AM. "Induction of natural killer activity in murine and human cells by CpG motifs in oligodeoxynucleotides and bacterial DNA." J. Immunol.157, 1840–1845, (1996).

Bauer M, Redecke V, Ellwart JW, Scherer B, Kremer JP, Wagner H, Lipford GB. "Bacterial CpG–DNA triggers activation and maturation of human CD11c–, CD123+ dendritic cells." J Immunol. 166:5000–7 (2001).

Bauer S, Kirschning CJ, Hacker H, Redecke V, Hausmann S, Akira S, Wagner H, Lipford GB. "Human TLR9 confers responsiveness to bacterial DNA via species–specific CpG motif recognition." Proc Natl Acad Sci U S A.98: 9237–9242, (2001).

Boggs RT et al., "Characterization and modulation of immune stimulation by modified oligonucleotides." Antisense Nucleic Acid Drug Dev 7(5):461–71, Oct. 1997.

Branda RF et al., "Amplification of antibody production by phosphorothioate oligodeoxynucleotides." J. Lab Clin Med 128(3):329–38, Sep. 1996.

Carpentier, AF, Chen L, Maltoni F, Delattre JY. "Oligodeoxynucleotides containing CpG motifs can induce rejection of a neuroblastoma in mice." Cancer Res. 59, 5429–5432, (1999).

Chace JH, Hooker NA, Mildenstein KL, Krieg AM, Chowdery JS. "Bacterial DNA–induced NK cell IFNγ production is dependent on macrophage secretion of IL–12." Clin. Immunol. Immunopathol. 84, 185–193, (1997).

Chen W, Yu Y, Shao C, Zhang M, Wang W, Zhang L, Cao X. "Enhancement of antigen–presenting ability of B lymphoma cells by immunostimulatory CpG–oligonucleotides and anti–CD40 antibody." Immunol Lett. 77: 17–23 (2001).

Chu RS, Targoni OS, Krieg AM, Lehman PV, Harding CV. "CpG oligodeoxynucleotides act as adjuvants that switch on T helper 1 (Th1) immunity." J. Exp. Med.186, 1623–1631, (1997).

Cowdery JS et al., "Bacterial DNA induces NK cells to produce IFN–gamma in vivo and increases the toxicity of lipopolysaccharides." J Immunol 156(12):4570–5, Jun. 15, 1996.

Davis HL, Weeratna R, Waldschmidt TJ, Tygrett L, Schorr J, Krieg AM. "CpG DNA is a potent enhancer of specific immunity in mice immunized with recombinant hepatitis B surface antigen." J. Immunol. 160, 870–876, (1998).

Decker T and Peschel C, "Effect of Immunostimulatory CpG–oligonucleotides in chronic lymphocytic leukemia B cells." Leuk Lymphoma 42:301–307 (2001).

Decker T et al., "ImmunostimulatoryCpG–oligonucleotides induce functional high affinity IL–2 receptors on B–CLL cells: costimulation with IL–2 results in a highly immunogenic phenotype." Exp Hematol 28:558–568 (2000).

Decker T, Schneller F, Kronschnabl M, Dechow T, Lipford GB, Wagner H, Peschel C. "Immunostimulatory CpG–oligonucleotides induce functional high affinity IL–2 receptors on B–CLL cells: costimulation with IL–2 results in a highly immunogenic phenotype." Exp Hematol. 28:558–68 (2000).

Erb KJ et al., "Infection of mice with Mycobacterium bovis–Bacillus Calmette–Guerin (BCG) suppresses allergen–induced airway eosinophilia." J Exp Med 187(4):561–9, Feb. 16, 1998.

Gursel M, Verthelyi D, Gursel I, Ishii KJ, Klinman DM. "Differential and competitive activation of human immune cells by distinct classes of CpG oligodeoxynucleotide." J Leukoc Biol.71: 813–820, (2002).

Gursel M, Verthelyi D, Klinman DM. "CpG oligodeoxynucleotides induce human monocytes to mature into functional dendritic cells." Eur J Immunol. 32 :2617–22 (2002).

Hadden J et al., "Immunopharmacology," JAMA, (1992) 268:20:2964–2969.

Hadden J et al., "Immunostimulants." TIPS, (1993), 141:169–174.

Halpern MD et al., "Bacterial DNA induces murine interferon–gamma production by stimulation of interleukin–12 and tumor necrosis factor–alpha." Cell Immunol 167(1):72–8, 1996.

Hartmann G, Weeratna R, Ballas ZK, Payette P, Suparto, I, Rasmussen WL, Wadschmidt M, Sajuthi D, Purcells RH, Davis HL, Krieg AM. "Delineation of a CpG phosphorothioate oligodeoxynucleotide for activating primate immune responses in vitro and in vivo." J. Immunol.164, 1617–1624, (2000).

Homung V, Rothenfusser S, Britsch S, Krug A, Jahrsdorfer B, Giese T, Endres S, Hartmann G. Quantitative expression of toll–like receptor 1–10 mRNA in cellular subsets of human peripheral blood mononuclear cells and sensitivity to CpG oligodeoxynucleotides. J Immunol.168, 4531–4537, (2002).

Jahrsdorfer B, Hartmann G, Racila E, Jackson W, Muhlenhoff L, Meinhardt G, Endres S, Link BK, Krieg AM, Weiner GJ. "CpG DNA increases primary malignant B cell expression of costimulatory molecules and target antigens." J Leukoc Biol.69:81–8 (2001).

Jahrsdorfer B, Jox R, Muhlenhoff L, Tschoep K, Krug A, Rothenfusser S, Meinhardt G, Emmerich B, Endres S, Hartmann G. "Modulation of malignant B cell activation and apoptosis by bcl–2 antisense ODN and immunostimulatory CpG ODN." J Leukoc Biol. 72 :83–92 (2002).

Kadowaki N, Antonenko S, Liu YJ. "Distinct CpG DNA and polyinosinic–polycytidylic acid double–stranded RNA, respectively, stimulate CD11c$^-$ type 2 dendritic cell precursors and CD11c$^+$ dendritic cells to produce type I IFN." J. Immunol. 166, 2291–2295, (2001).

Kadowaki N, Ho S, Antonenko S, Malefyt RW, Kastelein RA, Bazan F, Liu YJ. "Subsets of human dendritic cell precursors express different toll–like receptors and respond to different microbial antigens." J Exp Med. 17;194:863–9 (2001).

Kataoka, T., et al., "Antitumor Activity of Synthetic Oligonucleotides with Sequences from cDNA Encoding Proteins of Mycobacterium bovis BCG," Jpn. J. Cancer Res., 83:244–247, Mar. 1992.

Kimura, T., et al., "Binding of Oligoguanylate to Scavenger Receptors Is Requiered for Oligonucleotides to Augment NK Cell Activity and Induce IFN," J. Biochem., vol. 116, 5:991–994, 1994.

Kline JN et al., "CpG motif oligonucleotides are effective in prevention of eosinophilic inflammation in a murine model of asthma." J Invest Med 44(7):380A, 1996.

Kline JN et al., "CpG oligonucleotides can reverse as well as prevent TH2–mediated inflammation in a murine model of asthma." J Invest Med 45(7):298A, 1997.

Kline JN et al., "Immune redirection by CpG oligonucleotides. Conversion of a Th2 response to a Th1 response in a murine model of asthma." J Invest Med 45(3):282A, 1997.

Kline JN, Businga TR, Waldschmidt TJ, Weinstock JV, Krieg AM. "Cutting Edge: Modulation of airway inflammation by CpG oligodeoxynucleotides in a murine model of asthma." J. Immunol. 15, 2555–2559, (1998).

Klinman DM et al., "CpG motifs present in bacteria DNA rapidly induce lymphocytes to secrete interleukin 6, interleukin 12, and interferon gamma." Proc Natl Acad Sci USA 93(7):2879–83, Apr. 2, 1996.

Krieg AM el al, "A Role for Endogenous Retroviral Sequences in the Regulation of Lymphocyte Activation," the Journal of Immunology, vol. 143, 2448–2451, (1989).

Krieg AM et al, "The role of CpG dinucleotides in DNA vaccines", Trends in Microbiology, vol. 6, pp. 23–37, Jan. 1998.

Krieg AM et al, "Phosphorothioate Oligodeoxynucleotides: Antisense or Anti–Protein?," Antisense Research and Development, (1995), 5:241.

Krieg AM et al., "CpG DNA: A Pathogenic Factor in Systemic Lupus Erythematosus?", Journal of Clinical Immunology, (1995) 15:6:284–292.

Krieg AM et al., "Leukocyte Stimulation by Oligodeoxynucleotides," Applied Antisense Oligonucleotide Technology, (1998), 431–448.

Krieg AM et al., "CpG motifs in bacterial DNA trigger direct B–cell activation." Nation 374:546–9, Apr. 6, 1995.

Krieg AM et al., "Oligodeoxynucleotide modifications determine the magnitude of B cell stimulation by CpG motifs." Antisense Nucleic Acid Drug Dev 6(2):133–9, Summer 1996.

Krieg Am, "An innate immune defense mechanism based on the recognition of CpG motifs in microbial DNA." J Lab Clin Med 128(2):128–33, Aug. 1996.

Krieg AM. "GpG motifs in bacterial DNA and their immune effects." Annu. Rev. Immunol. 20, 709–760, (2002).

Krug A, Rothenfusser S, Hormung V, Jahrsdorfer B, Blackwell S, Ballas ZK, Endres S, Krieg AM, Hartmann G. "Identification of CpG oligonucleotide sequences with high induction of IFN–$\alpha/\beta$ in plasmacytoid dendritic cells." Eur. J. Immunol. 31, 2154–2163, (2001).

Krug A, Towarowski A, Britsch S, Rothenfusser S, Hornung V, Bals R, Giese T, Engelmann H, Endres S, Krieg AM, Hartmann G. "Toll–like receptor expression reveals CpG DNA as a unique microbial stimulus for plasmacytoid dendritic cells which synergizes with CD40 ligand to induce high amounts of IL–12." Eur J Immunol. 31, 3026–3037, 2001.

Kuramoto, et al., "Oligonucleotide Sequences Required for Natural Killer Cell Activation," Jpn. J. Cancer Res., 83:1128–1131, Nov. 1992.

Liang H, Nishioka Y, Reich CF, Pisetsky DS, Lipsky PE. "Activation of human B cells by phosphorothioate oligodeoxynucleotides." J. Clin. Invest. 98, 1119–1129, (1996).

Lipford GB et al., "Immunostimulatory DNA: sequence–dependent production of potentially harmful or useful cytokines." Eur J Immunol 27:3420–3426, (1997).

Lipford GB, Bauer M, Blank C, Reiter R, Wagner H, Heeg K. "CpG–containing synthetic oligodeoxynucleotides promote B and cytotoxic T cell responses to protein antigen: A new class of vaccine adjuvants." Eur. J. Immunol. 27, 2340–2344, (1997).

Macfarlane DE and Manzel L, "Antagonism of immunostimulatory CpG–oligodeoxynucleotides by quinacrine, chloroquine, and structurally related compounds." J Immunol 160(3):1122–31, Feb. 1, 1998.

Magone, MT, Chan CC, Beck L, Whitcup SM, Raz E. "Systemic or mucosal administration of immunostimulatory DNA inhibits early and late phases of murine allergic conjunctivitis." Eur. J. Immunol. 30, 1841–1850, (2000).

Matson S and Krieg AM, "Nonspecific suppression of [3H]thymidine incorporation by "control" oligonucleotides." Antisense Res Dev 2(4):325–30, Winter 1992.

Messina, et al., "Stimulation of in vitro Murine Lymphocyte Proliferation by Bacterial DNA," J. Immunol., vol. 147, 6:1759–1674, Sep. 15, 1991.

Messina, et al., "The Influence of DNA Structure on the in vitro Stimulation of Murine Lymphocytes by Natural and Synthetic Polynucleotide Antigens", Cellular Immunology, 147:148–157, 1993.

Mojcik, C., et al., "Administration of a Phosphorothioate Oligonucleotide Antisense Murine Endogenous Retroviral MCF env Causes Immune Effect in vivo in a Sequence–Specific Manner," Clinical Immunology and Immunopathology, (1993), 67:2:130–136.

Moldovenu GJ, Love–Homan L, Huang WQ, Krieg AM. "CpG DNA, a novel immune enhancer for systemic and mucosal immunization with influenza virus." Vaccine.16, 1216–1224, (1998).

Olbrich AR, Schimmer S, Heeg K, Schepers K, Schumacher TN, Dittmer U. "Effective postexposure treatment of retrovirus–induced disease with immunostimulatory DNA containing CpG motifs." J Virol. 76:11397–404 (2002).

Pisetsky et al., "Stimulation of Murine Lymphocyte Proliferation by a Phosphorothioate Oligonucleotide with Antisense Activity for Herpes Simplex Virus." Life Science, vol. 54, pp. 101–107 (1994).

Pisetsky, "Immunological Consequences of Nucleic Acid Therapy," Antisense Research and Development, 5:219–225 (1995).

Pisetsky, "The Immunological Properties of DNA," The Journal of Immunology, pp. 421–423 (1996).

Rankin R, Pontarollo R, loannou X, Krieg AM, Hecker R, Babiuk LA, Van Drunen Littel–van Den Hurk S. "CpG motif identification for veterinary and laboratory species demonstrates that sequence recognition is highly conserved." Antisense Nucleic Acid Drug Dev. 11, 333–340, (2001).

Sato et al., "Immunostimulatory DNA Sequences Necessary for Effective Intradermal Gene Immunization," Science, vol. 273, pp. 352–354, 1996.

Schwartz DA et al., CpG motifs in bacterial DNA cause inflammation in the lower respiratory tract. J Clin Invest 100(1):68–73, Jul. 1, 1997.

Sparwasser T, Koch ES, Vabulas RM, Heeg K, Lipford GB, Ellwart JW, Wagner. "Bacterial DNA and immunostimulatory CpG oligodeoxynucleotides trigger maturation and activation of murine dendritic cells." Eur. J. Immunol. 28, 2045–2054, 1998.

Takeshita F, Leifer CA, Gursel I, Ishii KJ, Takeshita S, Gursel M, Klinman DM. "Cutting edge: Role of Toll–like receptor 9 in CpG DNA–induced activation of human cells." J Immunol. 67:3555–3558, (2001).

Tokunaga T et al., "A synthetic single–stranded DNA, poly(dG,dC), induces interferon–alpha/beta and –gamma, augments natural killer activity, and suppresses tumor growth." Jpn J Cancer Res 79:682–6, Jun. 1988.

Tokunaga, T., et al., "Synthetic Oligonucleotides with Particular Base Sequences from the cDNA Encoding Proteins of Mycobacterium bovis BCG Induce Interferons and Activate Natural Killer Cells", Microbiol. Immunol., vol. 36, 1:55–66, 1992.

Verthelyi D, Ishii KJ, Gursel M, Takeshita F, Klinman DM. "Human peripheral blood cells differentially recognize and respond to two distinct CPG motifs." J Immunol. 166: 2372–2377, (2001).

Weeratna R, McCluskie MJ, Yu X, Davis HL. "CpG DNA Induces stronger immune responses with less toxicity than other adjuvants." Vaccine. 18, 1755–1762, (2000).

Wooldridge JE, Ballas Z, K, Krieg AM, Weiner GJ. "Immunostimulatory oligodeoxynucleotides containing CpG motifs enhance the efficacy of monoclonal antibody therapy of lymphoma." Blood. 89, 2994–2998, (1997).

Yamamoto S et al., "In vitro augmentation of natural killer cell activity and production of interferon–alpha/beta and—gamma with deoxyribonucleic acid fraction from Mycobacterium bovis BCG." Jpn J Cancer Res 79:866–73, Jul. 1988.

Yamamoto S, Yamamoto T, Kataoka T, Kuramoto E, Yano O, Tokunaga T. Unique palindromic sequences in synthetic oligodeoxynucleotides are required to induce IFN and augment IFN–mediated natural killer activity. J immunol. 148, 4072–4076, (1992).

Yamamoto, S., "Mode of Action Of Oligonucleotide Fraction Extracted From Mycobacterium bovis BCG", Kekkaku, vol. 69, 9:29–32, 1994.

Yamamoto, S., et al., "DNA from Bacteria, but Not from Vertebrates, Induces interferons, Activates Natural Killer Cells, and Inhibits Tumor Growth," Microbiol. Immunol., vol. 36, 9:983–997, 1992.

Yamamoto, T., et al., "Ability of Oligonucleotides with Certain Palindromes to Induce Interferon Produtin and Augment Natural Killer Cell Activity Is Associated with Their Base Length", Antisense Res. and Devel., 4:119–123, 1994.

Yamamoto, T., et al., "Lipofection of Synthetic Oligodeoxyribonucleotide Having a Palindromic Sequence AACGTT to Murine Splenocytes Enhances Interferon Production and Natural Killer Activity", Microbiol. Immunol., vol. 38, 10:831–836, 1994.

Yamamoto, T., et al., "Synthetic Oligonucleotides with Certain Palindromes Stimulate Interferon Production Of Human Peripheric B Lymphocytes in vitro," Jpn. J. Cancer Res., 85:775–779, 1994.

Yi Ak et al., "Rapid immune activation by CpG motifs in bacterial DNA. Systemic induction of IL–6 transcription through an antioxidant–sensitive pathway." J Immunol 157:5394–402, Dec. 15, 1996.

Yi, Ae–Kyung et al., "IFN–.gamma. Promotes IL–6 and IgM Secretion in Response to CpG Motifs in Bacterial DNA and Oligonucleotides," The Journal of Immunology, pp. 558–564 (1996).

* cited by examiner

IMT 021 (SEQ. ID N° 1); IMT 023 (SEQ. ID N° 9)

IMT 021 (SEQ. ID N° 1); IMT 023 (SEQ. ID N° 9)

| ODN(S) | Sequence |
|---|---|
| IMT 182 | TTTTCATTTTGTCATTTTGTTTTT |
| IMT 181 | TTTTTTTTTTTTTTTCATTTTGT |
| IMT 180 | TTTTTTTTTTTTTCATTTTGTTT |
| IMT 179 | TTTTTTTTTTTCATTTTGTTTTT |
| IMT 178 | TTTTTTTTTCATTTTGTTTTTTT |
| IMT 177 | TTTTTTTCATTTTGTTTTTTTTT |
| IMT 176 | TTTTTCATTTTGTTTTTTTTTTT |
| IMT 175 | TTTCATTTTGTTTTTTTTTTTTT |
| IMT 174 | TTCATTTTGTTTTTTTTTTTTTT |
| IMT 173 | CATTTTGTTTTTTTTTTTTTTTT |
| IMT 053 | TTTTTTTTTTTTTTTTTTTTTTT |
| IMT 022 | TGCTGCAAAAGAGCAAAAGAGCAA |

IMT 022 (SEQ.ID N°8); IMT 053 (SEQ ID N°19); IMT 173 (SEQ ID N°20); IMT174 (SEQ. ID N°21); IMT 175 (SEQ ID N°22); IMT 176 (SEQ ID N°23); IMT 177 (SEQ ID N°24); IMT 178 (SEQ ID N°25); IMT 179 (SEQ. ID N°26); IMT 180 (SEQ ID N°27); IMT 181 (SEQ ID N°28); IMT 182 (SEQ ID N°29)

Figure 3a

IMT 022 (SEQ.ID N°8); IMT 053 (SEQ ID N°19); IMT 173 (SEQ ID N°20); IMT174 (SEQ. ID N°21); IMT 175 (SEQ ID N°22); IMT 176 (SEQ ID N°23); IMT 177 (SEQ ID N°24); IMT 178 (SEQ ID N°25); IMT 179 (SEQ. ID N°26); IMT 180 (SEQ ID N°27); IMT 181 (SEQ ID N°28); IMT 182 (SEQ ID N°29)

IMT 022 (SEQ.ID N°8); IMT 053 (SEQ ID N°19); IMT 173 (SEQ ID N°20);
IMT174 (SEQ. ID N°21); IMT 175 (SEQ ID N°22); IMT 176 (SEQ ID N°23);
IMT 177 (SEQ ID N°24); IMT 178 (SEQ ID N°25); IMT 179 (SEQ. ID N°26);
IMT 180 (SEQ ID N°27); IMT 181 (SEQ ID N°28); IMT 182 (SEQ ID N°29)

IMT 022 (SEQ. ID N° 8); IMT 504 (SEQ. ID N° 2)

IMT 022 (SEQ. ID N° 8); IMT 504 (SEQ. ID N° 2)

Class II MHC

IMT 022 (SEQ. ID N° 8); IMT 504 (SEQ. ID N° 2)

IMT 021 (SEQ. ID N° 1); IMT 022 (SEQ. ID N°8); IMT 504 (SEQ ID N°2); IMT 506 (SEQ ID N°4)

IMT 021 (SEQ. ID N° 1); IMT 022 (SEQ. ID N° 8); IMT 504 (SEQ ID N° 2); IMT 506 (SEQ ID N° 4)

IMT 021 (SEQ. ID N° 1); IMT 022 (SEQ. ID N°8); IMT 504 (SEQ ID N°2); IMT 506 (SEQ ID N°4)

IMT 021 (SEQ. ID N° 1); IMT 022 (SEQ. ID N° 8); IMT 504 (SEQ ID N°2);
IMT 506 (SEQ ID N° 4); ODN(O): phosporodiester ODN

CD 40

IMT 021 (SEQ. ID N° 1); IMT 022 (SEQ. ID N° 8); IMT 504 (SEQ ID N° 2);
IMT 506 (SEQ ID N° 4); ODN(O): phosporodiester ODN Class I MHC IMT 021 (SEQ. ID N° 1); IMT 022 (SEQ. ID N°8); IMT 504 (SEQ ID N°2);
IMT 506 (SEQ ID N°4); ODN(O): phosporodiester ODN IMT 021 (SEQ. ID N 1); IMT 022 (SEQ. ID N 8);
IMT 504 (SEQ ID N 2); IMT 506 (SEQ ID N 4)

IMT 021 (SEQ. ID N 1); IMT 022 (SEQ. ID N 8);
IMT 504 (SEQ ID N 2); IMT 506 (SEQ ID N 4)

IMT 021 (SEQ. ID N° 1); IMT 022 (SEQ. ID N° 8); IMT 504 (SEQ ID N° 2)

CD 40

IMT 021 (SEQ. ID N° 1); IMT 022 (SEQ. ID N° 8); IMT 504 (SEQ ID N° 2)

IMT 021 (SEQ. ID Nº 1); IMT 022 (SEQ. ID Nº 8); IMT 504 (SEQ ID Nº 2)

IMT 021 (SEQ. ID N° 1); IMT 022 (SEQ. ID N° 8); IMT 504 (SEQ ID N° 2)

IMT 021 (SEQ. ID N° 1); IMT 022 (SEQ. ID N° 8); IMT 504 (SEQ ID N° 2)

IMT 021 (SEQ. ID N° 1); IMT 022 (SEQ. ID N° 8); IMT 504 (SEQ ID N° 2)

SEQUENCE LISTING

```
<160> NUMBER OF SEQ ID NOS: 74

<210> SEQ ID NO 1
<211> LENGTH: 24
<212> TYPE: DNA
<213> ORGANISM: Artificial Sequence
<220> FEATURE:
<223> OTHER INFORMATION: PCR primer

<400> SEQUENCE: 1
tgctgctttt gtgcttttgt gctt                                        24

<210> SEQ ID NO 2
<211> LENGTH: 24
<212> TYPE: DNA
<213> ORGANISM: Artificial Sequence
```

```
-continued

<220> FEATURE:
<223> OTHER INFORMATION: PCR primer

<400> SEQUENCE: 2
tcatcatttt gtcattttgt catt                                              24

<210> SEQ ID NO 3
<211> LENGTH: 24
<212> TYPE: DNA
<213> ORGANISM: Artificial Sequence
<220> FEATURE:
<223> OTHER INFORMATION: PCR primer

<400> SEQUENCE: 3
tcctcctttt gtcctttgt cctt                                               24

<210> SEQ ID NO 4
<211> LENGTH: 24
<212> TYPE: DNA
<213> ORGANISM: Artificial Sequence
<220> FEATURE:
<223> OTHER INFORMATION: PCR primer

<400> SEQUENCE: 4 tcttctttt gtctttttgt cttt                                               24

<210> SEQ ID NO 5
<211> LENGTH: 24
<212> TYPE: DNA
<213> ORGANISM: Artificial Sequence
<220> FEATURE:
<223> OTHER INFORMATION: PCR primer

<400> SEQUENCE: 5
tagtagtttt gtagttttgt agtt                                              24

<210> SEQ ID NO 6
<211> LENGTH: 24
<212> TYPE: DNA
<213> ORGANISM: Artificial Sequence
<220> FEATURE:
<223> OTHER INFORMATION: PCR primer

<400> SEQUENCE: 6
tggtggtttt gtggttttgt ggtt                                              24

<210> SEQ ID NO 7
<211> LENGTH: 24
<212> TYPE: DNA
<213> ORGANISM: Artificial Sequence
<220> FEATURE:
<223> OTHER INFORMATION: PCR primer

<400> SEQUENCE: 7
ttgttgtttt gttgttttgt tgtt                                              24

<210> SEQ ID NO 8
<211> LENGTH: 24
<212> TYPE: DNA
<213> ORGANISM: Artificial Sequence
<220> FEATURE:
<223> OTHER INFORMATION: PCR primer

<400> SEQUENCE: 8
tgctgcaaaa gagcaaaaga gcaa                                              24
```

<210> SEQ ID NO 9
<211> LENGTH: 24
<212> TYPE: DNA
<213> ORGANISM: Artificial Sequence
<220> FEATURE:
<223> OTHER INFORMATION: PCR primer

<400> SEQUENCE: 9
tgctgccccc gcgccccgc gccc                24

<210> SEQ ID NO 10
<211> LENGTH: 24
<212> TYPE: DNA
<213> ORGANISM: Artificial Sequence
<220> FEATURE:
<223> OTHER INFORMATION: PCR primer

<400> SEQUENCE: 10
tcattttttt gttttttgt catt                24

<210> SEQ ID NO 11
<211> LENGTH: 24
<212> TYPE: DNA
<213> ORGANISM: Artificial Sequence
<220> FEATURE:
<223> OTHER INFORMATION: PCR primer

<400> SEQUENCE: 11
tcattgtttt gttgttttgt catt               24

<210> SEQ ID NO 12
<211> LENGTH: 24
<212> TYPE: DNA
<213> ORGANISM: Artificial Sequence
<220> FEATURE:
<223> OTHER INFORMATION: PCR primer

<400> SEQUENCE: 12
tcattctttt gttcttttgt catt               24

<210> SEQ ID NO 13
<211> LENGTH: 24
<212> TYPE: DNA
<213> ORGANISM: Artificial Sequence
<220> FEATURE:
<223> OTHER INFORMATION: PCR primer

<400> SEQUENCE: 13
aaaaaactaa aaaaaactaa aaaa               24

<210> SEQ ID NO 14
<211> LENGTH: 24
<212> TYPE: DNA
<213> ORGANISM: Artificial Sequence
<220> FEATURE:
<223> OTHER INFORMATION: PCR primer

<400> SEQUENCE: 14
tcataatttt gtaattttgt catt               24

<210> SEQ ID NO 15
<211> LENGTH: 24
<212> TYPE: DNA
<213> ORGANISM: Artificial Sequence
<220> FEATURE:
<223> OTHER INFORMATION: PCR primer

```
<400> SEQUENCE: 15
tcattatttt gttattttgt catt                                              24

<210> SEQ ID NO 16
<211> LENGTH: 24
<212> TYPE: DNA
<213> ORGANISM: Artificial Sequence
<220> FEATURE:
<223> OTHER INFORMATION: PCR primer

<400> SEQUENCE: 16
tcatgatttt gtgattttgt catt                                              24

<210> SEQ ID NO 17
<211> LENGTH: 24
<212> TYPE: DNA
<213> ORGANISM: Artificial Sequence
<220> FEATURE:
<223> OTHER INFORMATION: PCR primer

<400> SEQUENCE: 17
tcatcctttt gtccttttgt catt                                              24

<210> SEQ ID NO 18
<211> LENGTH: 24
<212> TYPE: DNA
<213> ORGANISM: Artificial Sequence
<220> FEATURE:
<223> OTHER INFORMATION: PCR primer

<400> SEQUENCE: 18
tcatcttttt gtcttttgt catt                                               24

<210> SEQ ID NO 19
<211> LENGTH: 24
<212> TYPE: DNA
<213> ORGANISM: Artificial Sequence
<220> FEATURE:
<223> OTHER INFORMATION: PCR primer

<400> SEQUENCE: 19
tttttttttt tttttttttt tttt                                              24

<210> SEQ ID NO 20
<211> LENGTH: 24
<212> TYPE: DNA
<213> ORGANISM: Artificial Sequence
<220> FEATURE:
<223> OTHER INFORMATION: PCR primer

<400> SEQUENCE: 20
cattttgttt tttttttttt tttt                                              24

<210> SEQ ID NO 21
<211> LENGTH: 24
<212> TYPE: DNA
<213> ORGANISM: Artificial Sequence
<220> FEATURE:
<223> OTHER INFORMATION: PCR primer

<400> SEQUENCE: 21
ttcattttgt tttttttttt tttt                                              24
```

```
<210> SEQ ID NO 22
<211> LENGTH: 24
<212> TYPE: DNA
<213> ORGANISM: Artificial Sequence
<220> FEATURE:
<223> OTHER INFORMATION: PCR primer

<400> SEQUENCE: 22
ttttcatttt gttttttttt tttt                                              24

<210> SEQ ID NO 23
<211> LENGTH: 24
<212> TYPE: DNA
<213> ORGANISM: Artificial Sequence
<220> FEATURE:
<223> OTHER INFORMATION: PCR primer

<400> SEQUENCE: 23 tttttcatt ttgttttttt tttt                                               24

<210> SEQ ID NO 24
<211> LENGTH: 24
<212> TYPE: DNA
<213> ORGANISM: Artificial Sequence
<220> FEATURE:
<223> OTHER INFORMATION: PCR primer

<400> SEQUENCE: 24
ttttttttca ttttgttttt tttt                                              24

<210> SEQ ID NO 25
<211> LENGTH: 24
<212> TYPE: DNA
<213> ORGANISM: Artificial Sequence
<220> FEATURE:
<223> OTHER INFORMATION: PCR primer

<400> SEQUENCE: 25
tttttttttt cattttgttt tttt                                              24

<210> SEQ ID NO 26
<211> LENGTH: 24
<212> TYPE: DNA
<213> ORGANISM: Artificial Sequence
<220> FEATURE:
<223> OTHER INFORMATION: PCR primer

<400> SEQUENCE: 26
tttttttttt ttcattttgt tttt                                              24

<210> SEQ ID NO 27
<211> LENGTH: 24
<212> TYPE: DNA
<213> ORGANISM: Artificial Sequence
<220> FEATURE:
<223> OTHER INFORMATION: PCR primer

<400> SEQUENCE: 27
tttttttttt ttttcatttt gttt                                              24

<210> SEQ ID NO 28
<211> LENGTH: 24
<212> TYPE: DNA
<213> ORGANISM: Artificial Sequence
<220> FEATURE:
<223> OTHER INFORMATION: PCR primer
```

-continued

```
<400> SEQUENCE: 28
tttttttttt tttttcatt ttgt                                              24

<210> SEQ ID NO 29
<211> LENGTH: 24
<212> TYPE: DNA
<213> ORGANISM: Artificial Sequence
<220> FEATURE:
<223> OTHER INFORMATION: PCR primer

<400> SEQUENCE: 29
ttttcatttt gtcattttgt tttt                                             24

<210> SEQ ID NO 30
<211> LENGTH: 24
<212> TYPE: DNA
<213> ORGANISM: Artificial Sequence
<220> FEATURE:
<223> OTHER INFORMATION: PCR primer

<400> SEQUENCE: 30
tcatcaattt gtcaatttgt catt                                             24

<210> SEQ ID NO 31
<211> LENGTH: 24
<212> TYPE: DNA
<213> ORGANISM: Artificial Sequence
<220> FEATURE:
<223> OTHER INFORMATION: PCR primer

<400> SEQUENCE: 31
tcatcatatt gtcatattgt catt                                             24

<210> SEQ ID NO 32
<211> LENGTH: 24
<212> TYPE: DNA
<213> ORGANISM: Artificial Sequence
<220> FEATURE:
<223> OTHER INFORMATION: PCR primer

<400> SEQUENCE: 32
tcatcattat gtcattatgt catt                                             24

<210> SEQ ID NO 33
<211> LENGTH: 24
<212> TYPE: DNA
<213> ORGANISM: Artificial Sequence
<220> FEATURE:
<223> OTHER INFORMATION: PCR primer

<400> SEQUENCE: 33
tcatcattta gtcatttagt catt                                             24

<210> SEQ ID NO 34
<211> LENGTH: 24
<212> TYPE: DNA
<213> ORGANISM: Artificial Sequence
<220> FEATURE:
<223> OTHER INFORMATION: PCR primer

<400> SEQUENCE: 34
tcatcatttt atcattttat catt                                             24
```

```
<210> SEQ ID NO 35
<211> LENGTH: 24
<212> TYPE: DNA
<213> ORGANISM: Artificial Sequence
<220> FEATURE:
<223> OTHER INFORMATION: PCR primer

<400> SEQUENCE: 35
tcatcatttt ttcatttttt catt                                              24

<210> SEQ ID NO 36
<211> LENGTH: 24
<212> TYPE: DNA
<213> ORGANISM: Artificial Sequence
<220> FEATURE:
<223> OTHER INFORMATION: PCR primer

<400> SEQUENCE: 36
tcatcatttt ctcattttct catt                                              24

<210> SEQ ID NO 37
<211> LENGTH: 24
<212> TYPE: DNA
<213> ORGANISM: Artificial Sequence
<220> FEATURE:
<223> OTHER INFORMATION: PCR primer

<400> SEQUENCE: 37
tcatcatttt gacatttga catt                                               24

<210> SEQ ID NO 38
<211> LENGTH: 24
<212> TYPE: DNA
<213> ORGANISM: Artificial Sequence
<220> FEATURE:
<223> OTHER INFORMATION: PCR primer

<400> SEQUENCE: 38
tcatcattta gacatttaga catt                                              24

<210> SEQ ID NO 39
<211> LENGTH: 24
<212> TYPE: DNA
<213> ORGANISM: Artificial Sequence
<220> FEATURE:
<223> OTHER INFORMATION: PCR primer

<400> SEQUENCE: 39
tcatcattat gacattatga catt                                              24

<210> SEQ ID NO 40
<211> LENGTH: 24
<212> TYPE: DNA
<213> ORGANISM: Artificial Sequence
<220> FEATURE:
<223> OTHER INFORMATION: PCR primer

<400> SEQUENCE: 40
tcatcatatt gacatattga catt                                              24

<210> SEQ ID NO 41
<211> LENGTH: 24
<212> TYPE: DNA
<213> ORGANISM: Artificial Sequence
<220> FEATURE:
<223> OTHER INFORMATION: PCR primer
```

```
<400> SEQUENCE: 41
tcatcattaa gacattaaga catt                                    24

<210> SEQ ID NO 42
<211> LENGTH: 24
<212> TYPE: DNA
<213> ORGANISM: Artificial Sequence
<220> FEATURE:
<223> OTHER INFORMATION: PCR primer

<400> SEQUENCE: 42
tcatcatata gacatataga catt                                    24

<210> SEQ ID NO 43
<211> LENGTH: 24
<212> TYPE: DNA
<213> ORGANISM: Artificial Sequence
<220> FEATURE:
<223> OTHER INFORMATION: PCR primer

<400> SEQUENCE: 43
tcatcataat gacataatga catt                                    24

<210> SEQ ID NO 44
<211> LENGTH: 24
<212> TYPE: DNA
<213> ORGANISM: Artificial Sequence
<220> FEATURE:
<223> OTHER INFORMATION: PCR primer

<400> SEQUENCE: 44
tcatcataaa gacataaaga catt                                    24

<210> SEQ ID NO 45
<211> LENGTH: 24
<212> TYPE: DNA
<213> ORGANISM: Artificial Sequence
<220> FEATURE:
<223> OTHER INFORMATION: PCR primer

<400> SEQUENCE: 45
tcatcaaaaa gacaaaaaga catt                                    24

<210> SEQ ID NO 46
<211> LENGTH: 24
<212> TYPE: DNA
<213> ORGANISM: Artificial Sequence
<220> FEATURE:
<223> OTHER INFORMATION: PCR primer

<400> SEQUENCE: 46
acatcatttt gtcattttgt catt                                    24

<210> SEQ ID NO 47
<211> LENGTH: 24
<212> TYPE: DNA
<213> ORGANISM: Artificial Sequence
<220> FEATURE:
<223> OTHER INFORMATION: PCR primer

<400> SEQUENCE: 47
ccatcatttt gtcattttgt catt                                    24
```

```
<210> SEQ ID NO 48
<211> LENGTH: 24
<212> TYPE: DNA
<213> ORGANISM: Artificial Sequence
<220> FEATURE:
<223> OTHER INFORMATION: PCR primer

<400> SEQUENCE: 48
gcatcatttt gtcattttgt catt                                              24

<210> SEQ ID NO 49
<211> LENGTH: 24
<212> TYPE: DNA
<213> ORGANISM: Artificial Sequence
<220> FEATURE:
<223> OTHER INFORMATION: PCR primer

<400> SEQUENCE: 49
taatcatttt gtcattttgt catt                                              24

<210> SEQ ID NO 50
<211> LENGTH: 24
<212> TYPE: DNA
<213> ORGANISM: Artificial Sequence
<220> FEATURE:
<223> OTHER INFORMATION: PCR primer

<400> SEQUENCE: 50
ttatcatttt gtcattttgt catt                                              24

<210> SEQ ID NO 51
<211> LENGTH: 24
<212> TYPE: DNA
<213> ORGANISM: Artificial Sequence
<220> FEATURE:
<223> OTHER INFORMATION: PCR primer

<400> SEQUENCE: 51
tgatcatttt gtcattttgt catt                                              24

<210> SEQ ID NO 52
<211> LENGTH: 24
<212> TYPE: DNA
<213> ORGANISM: Artificial Sequence
<220> FEATURE:
<223> OTHER INFORMATION: PCR primer

<400> SEQUENCE: 52
tcctcatttt gtcattttgt catt                                              24

<210> SEQ ID NO 53
<211> LENGTH: 24
<212> TYPE: DNA
<213> ORGANISM: Artificial Sequence
<220> FEATURE:
<223> OTHER INFORMATION: PCR primer

<400> SEQUENCE: 53
tcttcatttt gtcattttgt catt                                              24

<210> SEQ ID NO 54
<211> LENGTH: 24
<212> TYPE: DNA
<213> ORGANISM: Artificial Sequence
<220> FEATURE:
<223> OTHER INFORMATION: PCR primer
```

<400> SEQUENCE: 54 tcgtcattttt gtcattttgt catt                                    24

<210> SEQ ID NO 55
<211> LENGTH: 24
<212> TYPE: DNA
<213> ORGANISM: Artificial Sequence
<220> FEATURE:
<223> OTHER INFORMATION: PCR primer

<400> SEQUENCE: 55 tcaacattttt gtcattttgt catt                                    24

<210> SEQ ID NO 56
<211> LENGTH: 24
<212> TYPE: DNA
<213> ORGANISM: Artificial Sequence
<220> FEATURE:
<223> OTHER INFORMATION: PCR primer

<400> SEQUENCE: 56 tcaccattttt gtcattttgt catt                                    24

<210> SEQ ID NO 57
<211> LENGTH: 24
<212> TYPE: DNA
<213> ORGANISM: Artificial Sequence
<220> FEATURE:
<223> OTHER INFORMATION: PCR primer

<400> SEQUENCE: 57 tcagcattttt gtcattttgt catt                                    24

<210> SEQ ID NO 58
<211> LENGTH: 24
<212> TYPE: DNA
<213> ORGANISM: Artificial Sequence
<220> FEATURE:
<223> OTHER INFORMATION: PCR primer

<400> SEQUENCE: 58 tcatcattttt gtcattttgt aatt                                    24

<210> SEQ ID NO 59
<211> LENGTH: 24
<212> TYPE: DNA
<213> ORGANISM: Artificial Sequence
<220> FEATURE:
<223> OTHER INFORMATION: PCR primer

<400> SEQUENCE: 59 tcatcattttt gtcattttgt tatt                                    24

<210> SEQ ID NO 60
<211> LENGTH: 24
<212> TYPE: DNA
<213> ORGANISM: Artificial Sequence
<220> FEATURE:
<223> OTHER INFORMATION: PCR primer

<400> SEQUENCE: 60 tcatcattttt gtcattttgt gatt                                    24

```
<210> SEQ ID NO 61
<211> LENGTH: 24
<212> TYPE: DNA
<213> ORGANISM: Artificial Sequence
<220> FEATURE:
<223> OTHER INFORMATION: PCR primer

<400> SEQUENCE: 61
tcatcatttt gtcattttgt cctt                                      24

<210> SEQ ID NO 62
<211> LENGTH: 24
<212> TYPE: DNA
<213> ORGANISM: Artificial Sequence
<220> FEATURE:
<223> OTHER INFORMATION: PCR primer

<400> SEQUENCE: 62
tcatcatttt gtcattttgt cttt                                      24

<210> SEQ ID NO 63
<211> LENGTH: 24
<212> TYPE: DNA
<213> ORGANISM: Artificial Sequence
<220> FEATURE:
<223> OTHER INFORMATION: PCR primer

<400> SEQUENCE: 63
tcatcatttt gtcattttgt cgtt                                      24

<210> SEQ ID NO 64
<211> LENGTH: 24
<212> TYPE: DNA
<213> ORGANISM: Artificial Sequence
<220> FEATURE:
<223> OTHER INFORMATION: PCR primer

<400> SEQUENCE: 64
tcatcatttt gtcattttgt caat                                      24

<210> SEQ ID NO 65
<211> LENGTH: 24
<212> TYPE: DNA
<213> ORGANISM: Artificial Sequence
<220> FEATURE:
<223> OTHER INFORMATION: PCR primer

<400> SEQUENCE: 65
tcatcatttt gtcattttgt cact                                      24

<210> SEQ ID NO 66
<211> LENGTH: 24
<212> TYPE: DNA
<213> ORGANISM: Artificial Sequence
<220> FEATURE:
<223> OTHER INFORMATION: PCR primer

<400> SEQUENCE: 66
tcatcatttt gtcattttgt cagt                                      24

<210> SEQ ID NO 67
<211> LENGTH: 24
<212> TYPE: DNA
<213> ORGANISM: Artificial Sequence
<220> FEATURE:
<223> OTHER INFORMATION: PCR primer
```

```
<400> SEQUENCE: 67
tcatcatttt gtcattttgt cata                                  24

<210> SEQ ID NO 68
<211> LENGTH: 24
<212> TYPE: DNA
<213> ORGANISM: Artificial Sequence
<220> FEATURE:
<223> OTHER INFORMATION: PCR primer

<400> SEQUENCE: 68
tcatcatttt gtcattttgt catc                                  24

<210> SEQ ID NO 69
<211> LENGTH: 24
<212> TYPE: DNA
<213> ORGANISM: Artificial Sequence
<220> FEATURE:
<223> OTHER INFORMATION: PCR primer

<400> SEQUENCE: 69
tcatcatttt gtcattttgt catg                                  24

<210> SEQ ID NO 70
<211> LENGTH: 12
<212> TYPE: DNA
<213> ORGANISM: Artificial Sequence
<220> FEATURE:
<223> OTHER INFORMATION: PCR primer

<400> SEQUENCE: 70
ttttcatttt gt                                               12

<210> SEQ ID NO 71
<211> LENGTH: 16
<212> TYPE: DNA
<213> ORGANISM: Artificial Sequence
<220> FEATURE:
<223> OTHER INFORMATION: PCR primer

<400> SEQUENCE: 71
ttttcatttt gttttt                                           16

<210> SEQ ID NO 72
<211> LENGTH: 20
<212> TYPE: DNA
<213> ORGANISM: Artificial Sequence
<220> FEATURE:
<223> OTHER INFORMATION: PCR primer

<400> SEQUENCE: 72
ttttcatttt gttttttttt                                       20

<210> SEQ ID NO 73
<211> LENGTH: 24
<212> TYPE: DNA
<213> ORGANISM: Artificial Sequence
<220> FEATURE:
<223> OTHER INFORMATION: PCR primer

<400> SEQUENCE: 73
tttttttttt ttcattttgt tttt                                  24
```

```
<210> SEQ ID NO 74
<211> LENGTH: 28
<212> TYPE: DNA
<213> ORGANISM: Artificial Sequence
<220> FEATURE:
<223> OTHER INFORMATION: PCR primer

<400> SEQUENCE: 74
ttttcatttt gtttttttttt tttttttt                                            28
```

IMMUNOSTIMULATORY OLIGONUCLEOTIDES AND USES THEREOF

FIELD OF THE INVENTION

The present invention relates generally to oligonucleotides containing the non-palindromic sequence motif:

$X_1X_2X_3X_4X_5X_6X_7X_8$, wherein $X_1$ is C,T,G or A (preferably T or C); $X_2$ is C,T,G or A; $X_7$ is C,T,G or A (preferably G); at least three, and preferably all, of $X_3$, $X_4$, $X_5$, $X_6$ and $X_8$ are T; with the proviso that, in the motif, a C does not precede a G, that are immunostimulatory in animals of the order Primate, including humans.

RELEVANT REFERENCES

Patent Documents

U.S. Pat. No. 5,663,153
U.S. Pat. No. 5,723,335
U.S. Pat. No. 6,090,791
U.S. Pat. No. 6,194,388
U.S. Pat. No. 6,207,646
U.S. Pat. No. 6,239,116
U.S. Pat. No. 6,429,199
EP 0468520
WO 95/26204
WO 96/02555
WO 98/40100
WO 98/52962
WO 99/33488
WO 99/56755
WO 00/62802
WO 01/00231
WO 01/00232
WO 01/55370

Other References

Azad, R. F., et al., "Antiviral Activity of a Phosphorothioate Oligonucleotide Complementary to RNA of the Human Cytomegalovirus Major Immediate-Early Region", Antimicrobial Agents and Chemotherapy, 37: 1945–1954, September 1993. Azuma, "Biochemical and Immunological Studies on Cellular Components of Tubercle Bacilli", Kekkaku, vol. 69. 9:45–55, 1992.

Kataoka, T., et al., "Antitumor Activity of Synthetic Oligonucleotides with Sequences from cDNA Encoding Proteins of Mycobacterium bovis BCG", Jpn. J. Cancer Res., 83:244–247, March 1992.

Kimura, T., et al., "Binding of Oligoguanylate to Scavenger Receptors Is Requiered for Oligonucleotides to Augment NK Cell Activity and Induce IFN", J. Biochem., vol. 116, 5:991–994, 1994.

Kuramoto, et al., "Oligonucleotide Sequences Required for Natural Killer Cell Activation", Jpn. J. Cancer Res., 83:1128–1131, November 1992.

Messina, et al., "The Influence of DNA Structure on the in vitro Stimulation of Murine Lymphocytes by Natural and Synthetic Polynucleotide Antigens", Cellular Immunology, 147:148–157, 1993.

Messina, et al., "Stimulation of in vitro Murine Lymphocyte Proliferation by Bacterial DNA", J. Immunol., vol.147, 6:1759–1764, Sep. 15, 1991.

Sato et al., "Immunostimulatory DNA Sequences Necessary for Effective Intradermal Gene Immunization", Science, vol. 273, pp. 352–354, 1996.

Tokunaga, T., et al., "Synthetic Oligonucleotides with Particular Base Sequences from the cDNA Encoding Proteins of Mycobacterium bovis BCG Induce Interferons and Activate Natural Killer Cells", Microbiol. Immunol., vol. 36, 1:55–66, 1992.

Tokunaga, et al., "A Synthetic Single-Stranded DNA, Ply (dG, dC), Induces Interferon .alpha./.beta and -.gamma., Augments Natural Killer Activity and Suppresses Tumor Growth" Jpn. J. Cancer Res., 79:682–686, June 1988.

Yamamoto, S., "Mode of Action Of Oligonucleotide Fraction Extracted From Mycobacterium bovis BCG", Kekkaku, vol. 69, 9:29–32, 1994.

Yamamoto, S., et al., "DNA from Bacteria, but Not from Vertebrates, Induces Interferons, Activates Natural Killer Cells, and Inhibits Tumor Growth", Microbiol. Immunol., vol. 36, 9:983–997,1992.

Yamamoto, S., et al., "Unique Palindromic Sequences in Synthetic Oligonucleotides are Required to Induce INF and Augment INF-Mediated Natural Killer Activity", J. Immunol., vol. 148,12:4072–4076, Jun. 15, 1992.

Yamamoto, T., et al., "Ability of Oligonucleotides with Certain Palindromes to Induce Interferon Produtin and Augment Natural Killer Cell Activity Is Associated with Their Base Length", Antisense Res. and Devel., 4:119–123, 1994.

Yamamoto, T., et al., "Lipofection of Synthetic Oligodeoxyribonucleotide Having a Palindromic Sequence AACGTT to Murine Splenocytes Enhances Interferon Production and Natural Killer Activity", Microbiol. Immunol., vol. 38, 10:831–836, 1994.

Yamamoto, T., et al., Synthetic Oligonucleotides with Certain Palindromes Stimulate Interferon Production Of Human Peripheric B Lymphocytes in vitro, Jpn. J. Cancer Res., 85:775–779, 1994.

Angier, N., Microbe DNA Seen as Alien By Immune System, New York Times, Apr. 11, 1995.

Ballas Z K et al., Induction of NK activity in murine and human cells by CpG motifs in oligodeoxynucleotides and bacterial DNA. J Immunol 157(5):1840–5, 1996.

Boggs R T et al., Characterization and modulation of immune stimulation by modified oligonucleotides. Antisense Nucleic Acid Drug Dev 7(5):461–71, October 1997.

Branda R F et al., Amplification of antibody production by phosphorothioate oligodeoxynucleotides. J. Lab Clin Med 128(3):329–38, September 1996.

Chu R S et al., CpG oligodeoxynucleotides act as adjuvants that switch on T helper 1 (Th1) immunity. J Exp Med 186(10):1623–31, Nov. 17, 1997.

Erb K J et al., Infection of mice with Mycobacterium bovis-Bacillus Calmette-Guerin (BCG) suppresses allergen-induced airway eosinophilia. J Exp Med 187(4): 561–9, Feb. 16, 1998.

Hadden J et al., Immunostimulants. TIPS, (1993), 141:169–174.

Hadden J et al., Immunopharmacology, JAMA, (1992) 268:20:2964–2969.

Halpern M D et al., Bacterial DNA induces murine interferon-gamma production by stimulation of interleukin-12 and tumor necrosis factor-alpha. Cell Immunol 167(1):72–8, 1996.

Krieg A M et al., "CpG DNA: A Pathogenic Factor in Systemic Lupus Erythematosus?", Journal of Clinical Immunology, (1995) 15:6:284–292.

Krieg A M et al, Phosphorothioate Oligodeoxynucleotides: Antisense or Anti-Protein?, Antisense Research and Development, (1995), 5:241.

Krieg A M et al., "Leukocyte Stimulation by Oligodeoxynucleotides", Applied Antisense Oligonucleotide Technology, (1998), 431–448.

Krieg A M et al, "The role of CpG dinucleotides in DNA vaccines", Trends in Microbiology, vol. 6, pp. 23–37, January 1998.

Krieg A M el al, A Role for Endogenous Retroviral Sequences in the Regulation of Lymphocyte Activation, the Journal of Immunology, vol. 143, 2448–2451.

Macfarlane D E and Manzel L, Antagonism of immunostimulatory CpG-oligodeoxynucleotides by quinacrine, chloroquine, and structurally related compounds. J Immunol 160(3):1122–31, Feb. 1, 1998.

Matson S and Krieg A M, Nonspecific suppression of [3H]thymidine incorporation by "control" oligonucleotides. Antisense Res Dev 2(4):325–30, Winter 1992.

Mojcik, C., et al., "Administration of a Phosphorothioate Oligonucleotide Antisense Murine Endogenous Retroviral MCF env Causes Immune Effect in vivo in a Sequence-Specific Manner", Clinical Immunology and Immunopathology, (1993), 67:2:130–136.

Schwartz D A et al., CpG motifs in bacterial DNA cause inflammation in the lower respiratory tract. J Clin Invest 100(1):68–73, Jul. 1, 1997.

Yamamoto S et al., In vitro augmentation of natural killer cell activity and production of interferon-alpha/beta and—gamma with deoxyribonucleic acid fraction from Mycobacterium bovis BCG. Jpn J Cancer Res 79:866–73, July 1988.

Pisetsky et al., Stimulation of Murine Lymphocyte Proliferation by a Phosphorothioate Oligonucleotide with Antisense Activity for Herpes Simplex Virus. Life Science, vol. 54, pp. 101–107 (1994).

Pisetsky, The Immunological Properties of DNA, The Journal of Immunology, pp. 421–423 (1996).

Pisetsky, Immunological Consequences of Nucleic Acid Therapy, Antisense Research and Development, 5:219–225 (1995).

Yi, Ae-Kyung et al., IFN-.gamma. Promotes IL-6 and IgM Secretion in Response to CpG Motifs in Bacterial DNA and Oligonucleotides, The Journal of Immunology, pp. 558–564 (1996).

Yi, Ae-Kyung et al., Rapid Immune Activation by CpG Motifs in Bacterial DNA, The Journal of Immunology, pp. 5394–5402 (1996).

Cowdery J S et al., Bacterial DNA induces NK cells to produce IFN-gamma in vivo and increases the toxicity of lipopolysaccharides. J Immunol 156(12):4570–5, Jun. 15, 1996.

Kline J N et al., CpG motif oligonucleotides are effective in prevention of eosinophilic inflammation in a murine model of asthma. J Invest Med 44(7):380A, 1996.

Kline J N et al., Immune redirection by CpG oligonucleotides. Conversion of a Th2 response to a Th1 response in a murine model of asthma. J Invest Med 45(3):282A, 1997.

Kline J N et al., CpG oligonucleotides can reverse as well as prevent TH2-mediated inflammation in a murine model of asthma. J Invest Med 45(7):298A, 1997.

Klinman D M et al., CpG motifs present in bacteria DNA rapidly induce lymphocytes to secrete interleukin 6, interleukin 12, and interferon gamma. Proc Natl Acad Sci USA 93(7):2879–83, Apr. 2, 1996.

Krieg A M, An innate immune defense mechanism based on the recognition of CpG motifs in microbial DNA. J Lab Clin Med 128(2):128–33, August 1996.

Krieg A M et al., CpG motifs in bacterial DNA trigger direct B-cell activation. Nation 374:546–9, Apr. 6, 1995.

Krieg A M et al., Oligodeoxynucleotide modifications determine the magnitude of B cell stimulation by CpG motifs. Antisense Nucleic Acid Drug Dev 6(2):133–9, Summer 1996.

Tokunaga T et al., A synthetic single-stranded DNA, poly (dG,dC), induces interferon-alpha/beta and -gamma, augments natural killer activity, and suppresses tumor growth. Jpn J Cancer Res 79:682–6, June 1988.

Yi A K et al., Rapid immune activation by CpG motifs in bacterial DNA. Systemic induction of IL-6 transcription through an antioxidant-sensitive pathway. J Immunol 157:5394–402, Dec. 15, 1996.

Lipford G B et al., CpG-containing synthetic oligonucleotides promote B and cytotoxic T cell responses to protein antigen: a new class of vaccine adjuvants. Eur J Immunol 27:2340–2344, 1997.

Lipford G B et al., Immunostimulatory DNA: sequence-dependent production of potentially harmful or useful cytokines. Eur J Immunol 27:3420–3426, (1997).

Rankin R et al., CpG motif identification for veterinary and laboratory species demonstrates that sequence recognition is highly concerved. Antisence Nucleic Acid Drug Dev 11:333–340 (2001).

Decker T et al., ImmunostimulatoryCpG-oligonucleotides induce functional high affinity IL-2 receptors on B-CLL cells: costimulation with IL-2 results in a highly immunogenic phenotype. Exp Hematol 28:558–568 (2000).

Decker T and Peschel C, Effect of immunostimulatory CpG-oligonucleotides in chronic lymphocytic leukemia B cells. Leuk Lymphoma 42:301–307 (2001).

Jahrsdorfer B et al., CpG DNA increases primary malignant B cell expression of costimulatory molecules and target antigens. J Leukoc Biol 69:81–88 (2001).

Krieg A M. GpG motifs in bacterial DNA and their immune effects. Annu. Rev. Immunol. 20, 709–760, (2002)

Kadowaki N, Antonenko S, Liu Y J. Distinct CpG DNA and polyinosinic-polycytidylic acid double-stranded RNA, respectively, stimulate CD11c$^-$ type 2 dendritic cell precursors and CD11c$^+$ dendritic cells to produce type I IFN. J. Immunol, 166, 2291–2295, (2001).

Krug A, Rothenfusser S, Hornung V, Jahrsdorfer B, Blackwell S, Ballas Z K, Endres S, Krieg A M, Hartmann G. Identification of CpG oligonucleotide sequences with high induction of IFN-α/β in plasmacytoid dendritic cells. Eur. J. Immunol. 31, 2154–2163, (2001).

Krug A, Towarowski A, Britsch S, Rothenfusser S, Hornung V, Bals R, Giese T, Engelmann H, Endres S, Krieg A M, Hartmann G. Toll-like receptor expression reveals CpG DNA as a unique microbial stimulus for plasmacytoid dendritic cells which synergizes with CD40 ligand to induce high amounts of IL-12. Eur J Immunol. 31, 3026–3037, 2001.

Hartmann G, Krieg A M. Mechanism and function of a newly identified CpG DNA motif in human primary B cells. J. Immunol.164, 944–952, (2000).

Chace J H, Hooker N A, Mildenstein K L, Krieg A M, Chowdery J S. Bacterial DNA-induced NK cell IFNγ production is dependent on macrophage secretion of IL-12. Clin. Immunol. Immunopathol. 84, 185–193, (1997).

Sparwasser T, Koch E S, Vabulas R M, Heeg K, Lipford G B, Ellwart J W, Wagner. Bacterial DNA and immunostimulatory CpG oligodeoxynucleotides trigger maturation and activation of murine dendritic cells. Eur. J. Immunol. 28, 2045–2054, 1998.

Ballas Z K, Rasmussen W L, Krieg A M. Induction of natural killer activity in murine and human cells by CpG motifs in oligodeoxynucleotides and bacterial DNA. J. Immunol. 157, 1840–1845, (1996).

Hornung V, Rothenfusser S, Britsch S, Krug A, Jahrsdorfer B, Giese T, Endres S, Hartmann G. Quantitative expression of toll-like receptor 1–10 mRNA in cellular subsets of human peripheral blood mononuclear cells and sensitivity to CpG oligodeoxynucleotides. J Immunol. 168, 4531–4537, (2002).

Lipford G B, Bauer M, Blank C, Reiter R, Wagner H, Heeg K. CpG-containing synthetic oligodeoxynucleotides promote B and cytotoxic T cell responses to protein antigen: A new class of vaccine adjuvants. Eur. J. Immunol. 27, 2340–2344, (1997).

Chu R S, Targoni O S, Krieg A M, Lehman P V, Harding C V. CpG oligodeoxynucleotides act as adjuvants that switch on T helper 1 (Th1) immunity. J. Exp. Med. 186, 1623–1631, (1997).

Moldovenu G J, Love-Homan L, Huang W Q, Krieg A M. CpG DNA, a novel immune enhancer for systemic and mucosal immunization with influenza virus. Vaccine.16, 1216–1224, (1998).

Davis H L, Weeratna R, Waldschmidt T J, Tygrett L, Schorr J, Krieg A M. CpG DNA is a potent enhancer of specific immunity in mice immunized with recombinant hepatitis B surface antigen. J. Immunol.160, 870–876, (1998).

Weeratna R, McCluskie M J, Yu X, Davis H L. CpG DNA induces stronger immune responses with less toxicity than other adjuvants. Vaccine. 18, 1755–1762, (2000).

Kline J N, Businga T R, Waldschmidt T J, Weinstock J V, Krieg A M. Modulation of airway inflammation by CpG oligodeoxynucleotides in a murine model of asthma. J. Immunol. 15, 2555–2559, (1998).

Magone, M T, Chan C C, Beck L, Whitcup S M, Raz E. Systemic or mucosal administration of immunostimulatory DNA inhibits early and late phases of murine allergic conjunctivitis. Eur. J. Immunol. 30, 1841–1850, (2000).

Wooldridge J E, Ballas Z, K, Krieg A M, Weiner G J. Immunostimulatory oligodeoxynucleotides containing CpG motifs enhance the efficacy of monoclonal antibody therapy of lymphoma. Blood. 89, 2994–2998, (1997).

Carpentier, A F, Chen L, Maltoni F, Delattre J Y. Oligodeoxynucleotides containing CpG motifs can induce rejection of a neuroblastoma in mice. Cancer Res. 59, 5429–5432, (1999).

Hartmann G, Weeratna R, Ballas Z K, Payette P, Suparto, I, Rasmussen W L, Wadschmidt M, Sajuthi D, Purcells R H, Davis H L, Krieg A M. Delineation of a CpG phosphorothioate oligodeoxynucleotide for activating primate immune responses in vitro and in vivo. J. Immunol.164, 1617–1624, (2000).

Rankin R, Pontarollo R, Ioannou X, Krieg A M, Hecker R, Babiuk L A, Van Drunen Littel-van Den Hurk S. CpG motif identification for veterinary and laboratory species demonstrates that sequence recognition is highly conserved. Antisense Nucleic Acid Drug Dev. 11, 333–340, (2001).

Verthelyi D, Ishii K J, Gursel M, Takeshita F, Klinman D M. Human peripheral blood cells differentially recognize and respond to two distinct CPG motifs. J Immunol. 166: 2372–2377, (2001).

Gursel M, Verthelyi D, Gursel I, Ishii K J, Klinman D M. Differential and competitive activation of human immune cells by distinct classes of CpG oligodeoxynucleotide. J Leukoc Biol.71: 813–820, (2002).

Yamamoto S, Yamamoto T, Kataoka T, Kuramoto E, Yano O, Tokunaga T. Unique palindromic sequences in synthetic oligodeoxynucleotides are required to induce IFN and augment IFN-mediated natural killer activity. J immunol 148, 4072–4076, (1992).

Liang H, Nishioka Y, Reich C F, Pisetsky D S, Lipsky P E. Activation of human B cells by phosphorothioate oligodeoxynucleotides. J. Clin. Invest. 98, 1119–1129, (1996).

Takeshita F, Leifer C A, Gursel I, Ishii K J, Takeshita S, Gursel M, Klinman D M. Cutting edge: Role of Toll-like receptor 9 in CpG DNA-induced activation of human cells. J Immunol. 67:3555–3558, (2001).

Bauer S, Kirschning C J, Hacker H, Redecke V, Hausmann S, Akira S, Wagner H, Lipford G B. Human TLR9 confers responsiveness to bacterial DNA via species-specific CpG motif recognition. Proc Natl Acad Sci USA. 98: 9237–9242, (2001).

Vollmer J, Janosch A, Laucht M, Ballas Z K, Schetter C, Krieg A M. Highly immunostimulatory CpG-free oligodeoxynucleotides for activation of human leukocytes. Antisense Nucleic Acid Drug Dev. 12:165–175, (2002).

Jahrsdorfer B, Jox R, Muhlenhoff L, Tschoep K, Krug A, Rothenfusser S, Meinhardt G, Emmerich B, Endres S, Hartmann G. Modulation of malignant B cell activation and apoptosis by bcl-2 antisense ODN and immunostimulatory CpG ODN. J Leukoc Biol. 72 :83–92 (2002)

Gursel M, Verthelyi D, Klinman D M. CpG oligodeoxynucleotides induce human monocytes to mature into functional dendritic cells. Eur J Immunol. 32 :2617–22 (2002).

Hornung V, Rothenfusser S, Britsch S, Krug A, Jahrsdorfer B, Giese T, Endres S, Hartmann G. Quantitative expression of toll-like receptor 1–10 mRNA in cellular subsets of human peripheral blood mononuclear cells and sensitivity to CpG oligodeoxynucleotides. J Immunol. 168:4531–7 (2002).

Krug A, Towarowski A, Britsch S, Rothenfusser S, Hornung V, Bals R, Giese T, Engelmann H, Endres S, Krieg A M, Hartmann G. Toll-like receptor expression reveals CpG DNA as a unique microbial stimulus for plasmacytoid dendritic cells which synergizes with CD40 ligand to induce high amounts of IL-12. Eur J Immunol. 31:3026–37 (2002).

Kadowaki N, Ho S, Antonenko S, Malefyt R W, Kastelein R A, Bazan F, Liu Y J. Subsets of human dendritic cell precursors express different toll-like receptors and respond to different microbial antigens. J Exp Med. 17;194:863–9 (2001).

Krug A, Rothenfusser S, Hornung V, Jahrsdorfer B, Blackwell S, Ballas Z K, Endres S, Krieg A M, Hartmann G. Identification of CpG oligonucleotide sequences with high induction of IFN-alpha/beta in plasmacytoid dendritic cells. Eur J Immunol. 31:2154–63 (2001).

Bauer M, Redecke V, Ellwart J W, Scherer B, Kremer J P, Wagner H, Lipford G B. Bacterial CpG-DNA triggers activation and maturation of human CD11c−, CD123+ dendritic cells. J Immunol. 166:5000–7 (2001).

Olbrich A R, Schimmer S, Heeg K, Schepers K, Schumacher T N, Dittmer U. Effective postexposure treatment of retrovirus-induced disease with immunostimulatory DNA containing CpG motifs. J Virol. 76:11397–404 (2002).

Decker T, Peschel C. Effect of immunostimulatory CpG-oligonucleotides in chronic lymphocytic leukemia B cells. Leuk Lymphoma. 42:301–7 (2001).

Decker T, Schneller F, Sparwasser T, Tretter T, Lipford G B, Wagner H, Peschel C. Immunostimulatory CpG-oligonucleotides cause proliferation, cytokine production, and an immunogenic phenotype in chronic lymphocytic leukemia B cells. Blood. 95:999–1006 (2000).

Decker T, Schneller F, Kronschnabl M, Dechow T, Lipford G B, Wagner H, Peschel C. Immunostimulatory CpG-oligonucleotides induce functional high affinity IL-2 receptors on B-CLL cells: costimulation with IL-2 results in a highly immunogenic phenotype. Exp Hematol. 28:558–68 (2000).

Jahrsdorfer B, Hartmann G, Racila E, Jackson W, Muhlenhoff L, Meinhardt G, Endres S, Link B K, Krieg A M, Weiner G J. CpG DNA increases primary malignant B cell expression of costimulatory molecules and target antigens. J Leukoc Biol.69:81–8 (2001).

Chen W, Yu Y, Shao C, Zhang M, Wang W, Zhang L, Cao X. Enhancement of antigen-presenting ability of B lymphoma cells by immunostimulatory CpG-oligonucleotides and anti-CD40 antibody. Immunol Lett. 77: 17–23 (2001).

BACKGROUND OF THE INVENTION

The Immune System

The major function of the immune system is to protect the host of invading pathogens. A number of different cell types, both antigen-independent and antigen-specific, have evolved to detect and neutralize these invading pathogens. Among them, lymphocytes have an important characteristic, which is their ability to specifically recognize antigens, a feature not possessed by any other cell. This means that any lymphocyte function stimulated by an antigen is directed solely at that antigen.

Lymphocytes may be divided into two major populations: T and B. T lymphocytes have a central role in regulating the immune response and for this they produce and secrete lymphokines (i.e.: interleukins). B-lymphocytes are the only cells that produce antibodies, which are proteins—Immunoglobulins (IgG)—that recognize and bind antigens.

Some T lymphocytes are known as helper (Th lymphocytes) because they assist B cells to produce antibody. T-lymphocytes express a characteristic membrane molecule designated CD4. Other T lymphocytes are known as cytotoxic (CTL) because they are capable of killing certain cells. They express a different characteristic membrane protein designated CD8.

Th lymphocytes, in mice, have been subdivided according to the lymphokines they produce in groups designated Th0, Th1 and Th2. In general, Th 1 lymphocytes produce lymphokines which stimulate macrophages and CTLS (IL2, IFNγ, TNF-β), Th 2 lymphocytes produce lymphokines which stimulate B lymphocytes to proliferate and produce antibody (IL 2, IL5, IL6, IL10, IL13), whilst Th 0 lymphocytes produce a mixture of lymphokines and are thought to be an intermediate stage from which Th 1 and Th 2 lymphocytes are derived. In humans, Th1 and Th2 like lymphocytes have been demonstrated, although they do seem to show a less strict division with respect to their patterns of cytokine secretion.

A third population of lymphocytes, which lack the major makers of T and B cells include the natural killer cells (NK cells), the killer cells (K cells) and the lymphokine-activated killer cells (L A K cells). NK cells can kill certain tumor cells and some virally infected cells, but unlike cytotoxic T lymphocytes they are not capable of recognizing a specific antigen. K cells are able to bind to cells, which have antibody to them via their antigen-binding regions and kill them. L A K cells do not specifically recognize an antigen but they are capable of destroying a wider range of targets a NK cells.

Macrophages and dendritic cells play a critical role in initiating immune responses, helping T cells to respond to antigens.

There are several antibody classes. The IgG class comprises most of the circulating antibodies and it has four subclasses designated IgG1, IgG2, IgG3 and IgG4.

The IgM class comprises about 10% of the circulating antibodies. These are the principal antibodies produce during the primary immunological response. The IgA class comprises most of the antibody secreted at mucous membranes and exerts its protective effect by blocking access of the antigen to the inner body. The IgD class comprises less than 1% of serum antibodies and its biological role is largely unknown. The IgE class comprises antibodies that are mainly bound to the surface of most cells and basophils. These antibodies are associated with reactions that occur in individuals who are undergoing allergic reactions.

Vaccines and Vaccines Adjuvants

Vaccines are preparations used to stimulate animals to mount an immune response against antigens included in the vaccine.

Vaccines often include adjuvants, which are substances that used in combination with specific antigen produce more immunity than the antigen used alone. (Ramon, G., 1926. Procedes pour accroite la production des antitoxins. Ann. Inst. Pasteur. 40, 1–10).

Many kind of compounds function as vaccine adjuvants (Edelman, R., 2000. An overview of adjuvant use, in: Vaccine Adjuvants. Preparation Methods and Research Protocols. D. T. O'Hagan, Ed., Humana Press, Totowa, N.J. References cited in this article are incorporated herein as background material). However, currently, the only adjuvants approved for use in humans are aluminum salts (Gupta, R. K. and Rost, B. E., 2000. Aluminum compounds as vaccine adjuvants in: Vaccine Adjuvants. Preparation Methods and Research Protocols. D. T. O'Hagan, Ed., Humana Press, Totowa, N.J.) and the oil-in-water emulsion M F 59 (Ott, G. Radhakrishman, R. Fang, J. and Hora, M., 2000. The adjuvant M F 59: A 10-Year Perspective, in : Vaccine Adjuvants. Preparation Methods and Research Protocols. D. T. O'Hagan, Ed., Humana Press, Totowa, N.J.).

Nucleic Acids as Immunostimulatory Compounds

Several polynucleotides have been demonstrated to have immunostimulatory properties. For example, poly (I, C) is an inducer of interferon (IFN) production, macrophage activation and NK cell activation (Talmadge, J. E., Adams, J., Phillips, H., Collins, M., Lenz, B., Schneider, M., Schlick, E., Ruffmann, R., Wiltrout, R. H., Chirigos, M. A. 1985. Immunomodulatory effects in mice of polyinosinic-polycytidylic acid complexed with poly-L:-lysine and carboxymethylcellulose. Cancer Res. 45:1058; Wiltrout, R. H., Salup, R. R., Twilley, T. A., Talmage, J. E. 1985. mmuno-modulation of natural killer activity by polyribonucleotides. J. Biol. Resp. Mod. 4:512), poly (dG,dC) is mitogenic for B cells (Messina, J. P., Gilkerson, G. S., Pisetsky, D. S. 1993. The influence of DNA structure on the in vitro stimulation of murine lymphocytes by natural and synthetic polynucleotide antigens. Cell. Immunol. 147:148) and induces IFN and NK activity (Tocunaga, T., Yamamoto, S., Namba, K.1988. A synthetic single-stranded DNA, poly(dG,dC), induces interferon-α/β and -γ, augments natural killer activity, and suppresses tumor growth. Jpn.J. Cancer Res. 79:682).

Bacterial DNA has also been reported to have immunostimulatory properties. These properties include the induction of cytokines (interferon gamma (IFN γ), alpha (IFN α), beta (IFN β); tumor necrosis factor alpha (TNF α), interleukin 6 (IL6), 12 (IL 12) and 18 (IL 18), as well as the direct stimulation of B cells (Yamamoto, S. et al. 1988. In vitro augmentation of natural killer cell activity of interferon α/β and γ with deoxyribonucleic acid fraction from *Mycobacterium bovis* BCG. Jpn. J. Cancer Res. (Gann) 79: 866–873; Yamamoto S. et al, 1992. DNA from bacteria, but not from vertebrates, induces interferons, activates natural killer cells and inhibits tumor growth. Microbiol. Immunol. 36: 983–997.; Klinman, D. M., Yi, A-K., Beaucage, S. L., Conover, J. and Krieg, A. M., 1996.

CpG motifs present in bacterial DNA rapidly induce lymphocytes to secrete interleukin 6, interleukin 12 and interferon γ. Proc. Natl. Acad. Sci. USA 93, 2879–2883. Halpern, M. D., et al. 1996. Bacterial DNA induces murine interferon-γ production by stimulation of interleukin-12 and tumor necrosis factor-α. Cell. Immunol. 167: 72–78. Sparwasser, T. et al, 1997. Macrophages sense pathogens via DNA motifs: induction of tumor necrosis factor-α-mediated shock. Eur. J. Immunol. 27: 1671–1679; Krieg, A. M. et al., 1995. CpG motifs in bacterial DNA trigger direct B-cell activation. Nature 374: 345–349).

In contrast, it has been reported that mammalian DNA has no significant immune effects (Pisetsky, D. S. 1996. The immunologic properties of DNA. J. Immunol. 156: 421–423; Messina et al. 1991. Stimulation of in vitro murine lymphocyte proliferation by bacterial DNA. J. Immunol. 147: 1759).

Synthetic DNA has also been reported to be immunostimulatory if contains unmethylated CpG motifs. (Yamamoto, S et al.; 1992. Unique palindromic sequences in synthetic oligonucleotides are required to induce INF and augment INF-mediated natural killer activity. J. Immunol. 148: 4072–4076; Ballas, Z. K., et al.; 1996. Induction of NK activity in murine and human cells by CpG motifs in oligodeoxynucleotides and bacterial DNA. J. Immunol. 157: 1840–1845; Hartmann, G., Krieg, A. M. 2000. Mechanism and function of a newly identified CpG DNA motif in human primary B cells. J. Immunol. 164:944; Hartmann, G., Weeratna, R. D., Ballas, Z. K., Payette, P., Blackwell, S., Suparto, I., Rasmussen, W. L., Waldschmidt, M., Sajuthi, D., Purcell, R. H., Davis, H. L., Krieg, A. M. 2000. Delineation of a CpG phosphorothioate oligodeoxynucleotide for activating primate immune responses in vitro and in vivo. J. Immunol. 164:1617; Verthelyi, D., Ishii, K. J., Gursel, M., Takeshita, F., Klinman, D. M. 2001. Human peripheric blood cells differentially recognize and respond to two distinct CpG motifs. J. Immunol. 166:2372). However, one oligonucleotide containing phosphorothioate bonds that lack CpG motifs has been found to have some immunostimulatory activity on human B cells (Liang, H., Nishioka, Y., Reich, C. F., Pisetsky, D. S., Lipsky, P. E. 1996. Activation of human B cells by phosphorothioate oligonucleotides. J. Clin. Invest. 98:1119). This particular non-CpG oligonucleotide containing phosphorothioate bonds is a poy-T chain, 20 nucleotides long. Also, Vollmer et al (Vollmer J, Janosch A, Laucht M, Ballas Z K, Schetter C, Krieg A M. Highly immunostimulatory CpG-free oligodeoxynucleotides for activation of human leukocytes. Antisense Nucleic Acid Drug Dev. 12:165–175, 2002) reported immunostimulation by phosphorothioate poly T ODNs. These authors pointed out that poly T ODNs are only active as phosphorothioate ODNs and have much lower activity than CpG ODNs.

It has now been discovered that non-CpG oligonucleotides containing the following non-palindromic sequence motif:

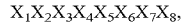

wherein $X_1$ is C,T,G or A (preferably T or C); $X_2$ is C,T,G or A; $X_7$ is C,T,G or A (preferably G); at least three, and preferably all, of $X_3$, $X_4$, $X_5$, $X_6$ and $X_8$ are T; with the proviso that, in the motif, a C does not precede a G, have potent immunostimulatory activity. Therefore, these oligonucleotides can be administered to subjets to treat "immune system deficiencies" or in conjunction with a vaccine, as adjuvants, to boost the immune system in order to have a better response to the vaccine or administered to subjects to increase the responsiveness to tumors.

SUMMARY OF THE INVENTION

It has now been discovered that non-CpG oligonucleotides containing the following non-palindromic sequence motif:

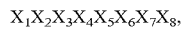

wherein $X_1$, $X_2$ and $X_7$ are C,T,G or A; at least three of $X_3$, $X_4$, $X_5$, $X_6$ and $X_8$ are T; with the proviso that, in the motif, a C does not precede a G, are useful as inmmunostimulants in animals of the order Primate, including humans.

According to a preferred embodiment, $X_1$ consist of a C or a T and $X_7$ consist of a G. More preferably $X_3$,$X_4$,$X_5$,$X_6$ $X_7$ $X_8$ of the immunostimulatory motif consist of TTTTGT. Even more advantageously $X_1X_2X_3X_4X_5X_6X_7X_8$ consist of CNTTTTGT or TNTTTTGT wherein N is C, T, G or A. Those of $X_3$–$X_6$ and $X_8$ that are not T can be any nucleotide (e.g., C, T, G, A) or can be absent so that the nucleotide preceding links directly with the nucleotide following the position of the omitted nucleotide (S). The oligonucleotides of this invention are useful as adjuvants in a vaccine formulation comprising one or more antigens. In embodiments of this aspect, the vaccine formulation can be liquid or lyophilized in dosage form. Many dosage forms are known in the art and can be applied herein. In embodiments of this aspect the oligonucleotides of this invention are present in the composition at a dose of from about 10 to 10,000 µg per dose. In these preparations the oligonucleotides of this invention may be combined with other immunostimulant compounds. Examples of well known immunostimulants are: α-interferon, β-interferon, γ-interferon, granulocyte macrophage colony stimulator factor (GM-CSF), interleukin 2 (IL2), interleukin 12 (IL12) and CpG oligonucleotide.

In preferred embodiments the antigenic component of the vaccine is one or more, natural or recombinant, antigens of viruses like: Human immunodeficiency viruses, such as HIV-1 and HIV-2, polio viruses, hepatitis A virus, human coxsackie viruses, rhinoviruses, echoviruses, equine encephalitis viruses, rubella viruses, dengue viruses, encephalitis viruses, yellow fever viruses, coronaviruses), vesicular stomatitis viruses, rabies viruses, ebola viruses, parainfluenza viruses, mumps virus, measles virus, respiratory syncytial virus, influenza viruses, Hantaan viruses, bunga viruses, hemorrhagic fever viruses, reoviruses, orbiviuises, rotaviruses, Hepatitis B virus, parvoviruses, papilloma viruses, polyoma viruses, adenoviruses), herpes simplex virus (HSV) 1 and 2, varicella zoster virus, cytomegalovirus (CMV), variola viruses, vaccinia viruses, pox viruses, African swine fever virus, the unclassified agent of delta hepatitis, the agents of non-A, non-B hepatitis; of infectious bacteria like: *Helicobacter pylori, Borrelia burgdorferi, Legionella pneumophila, Mycobacterium tuberculosis, Mycobacterium bovis (BCG), Mycobacterium avium, Mycobacterium intracellulare, Staphylococcus aureus, Neisseria gonorrhoeae, Neisseria meningitidis, Listeria monocytogenes, Streptococcus pyogenes, Streptococcus pneumoniae, Haemophilus influenzae, Moraxella catharralis, Klebsiella pneumoniae, Bacillus anthracis, Corynebacterium diphtheriae, Clostridium perfringers, Clostridium tetani, Enterobacter aerogenes, Klebsiella pneumoniae, Pasturella multocida*, and *Treponema pallidum*; of infectious fungi like: *Cryptococcus neoformans, Histoplasma capsulatum, Coccidioides immitis, Blastomyces dermatitidis, Candida albicans*; of infectious protists like: *Plasmodium falciparum, Trypanosoma cruzi, Leishmania donovani* and *Toxoplasma gondii*. and; of human tumoral cells.

In embodiments of this aspect one or more of the oligonucleotides of this invention and the antigen are administered simultaneously locally (by oral, rectal, intranasal or transdermal route) or systemically (by intradermic or intramuscular injection). An aspect of this invention is a method of vaccination of a person. The person can be vaccinated prophylactically or therapeutically.

A prophylactic vaccine is designed to elicit protection from a disease caused by an infectious agent through the induction of specific immunity.

A therapeutic vaccine is designed to induce remission of an illness (i.e. a tumor and metastasis or illness associated with, an infectious agent like the human immunodeficiency virus).

The method of vaccination includes administering one or more of the oligonucleotides of this invention and one or more antigens—that is, the vaccine can be designed against one disease target or a combination of disease targets.

Another aspect of this invention is a method of treatment of a person with a tumoral disease or an immunological disorder, with one or more of the oligonucleotides of this invention to stimulate his/her endogenous immune response. Examples of tumoral disease are: Chronic Myelogenous Leukemia, Precursor B-lymphoblastic lymphoma, B-cell chronic lymphocytic leukaemia, Lymphoplasmacytic lymphoma, Mantle cell lymphoma, Follicle center lymphoma, (follicular and diffuse), Marginal zone-B lymphoma, Extranodal lymphoma, Nodal marginal zone B-cell lymphoma, Splenic marginal zone B-cell lymphoma, Hairy cell leukaemia, Plasmocytoma, Diffuse large B-cell lymphoma, Burkitt's lymphoma, High grade B-cell lymphoma, Burkitt like, Melanoma, Kaposi's Sarcoma, Multiple Myeloma, Renal Cell Carcinoma, Bladder Cancer, Lung Cancer, Skin Cancer, Breast Cancer, Colon Cancer and Uterus Cancer. Examples of immunological disorders are: Allergy, Severe Combined Immunodeficiency, Chronic Granulomatous disease, and Acquired Immunodeficiency Disease.

In embodiments of this aspect, one or more of the oligonucleotide of this invention is/are present in a pharmaceutical formulation that can be liquid or lyophilized in dosage form. Many dosage forms are known in the art and can be applied herein. In embodiments of this aspect one or more of the oligonucleotides of this invention is/are present in the composition at a dose of from about 10 to 10,000 µg per dose. In these preparations one or more of the oligonucleotides of this invention may be combined with other immunostimulant compounds. Examples of well known immunostimulants are: α-interferon, β-interferon, γ-interferon, granulocyte macrophage colony stimulator factor (GM-CSF), interleukin 2 (IL2), interleukin 12 (IL12), CpG oligonucleotides and Mycobacterium bovis BCG cells. Also, one or more of the oligonucleotides of this invention may be combined with an antiinfective or anticancer drug, or a surgical procedure. In all these cases the oligonucleotides of this invention may be administered before, after or simultaneously with the alternative treatment.

Another aspect of this invention is a method of treatment of a person with a tumoral disease or an immunological disorder, contacting lymphocytes or plasmacytoid dendritic cells from the subject with one or more of the oligonucleotides of this invention "ex vivo" and readministering the activated cells to the subject. In embodiments of this aspect one or more of the oligonucleotides of this invention are present in the incubation media in a concentration of about 0.10 to 100 µg per ml.

5' TCGTCGTTTTGTCGTTTTGTCGTT 3', the phosphorothioate non-CpG ODN IMT 021 (SEQ ID NO: 1). Data represent the mean and standard deviation of five independent assays.

Figure 2A:
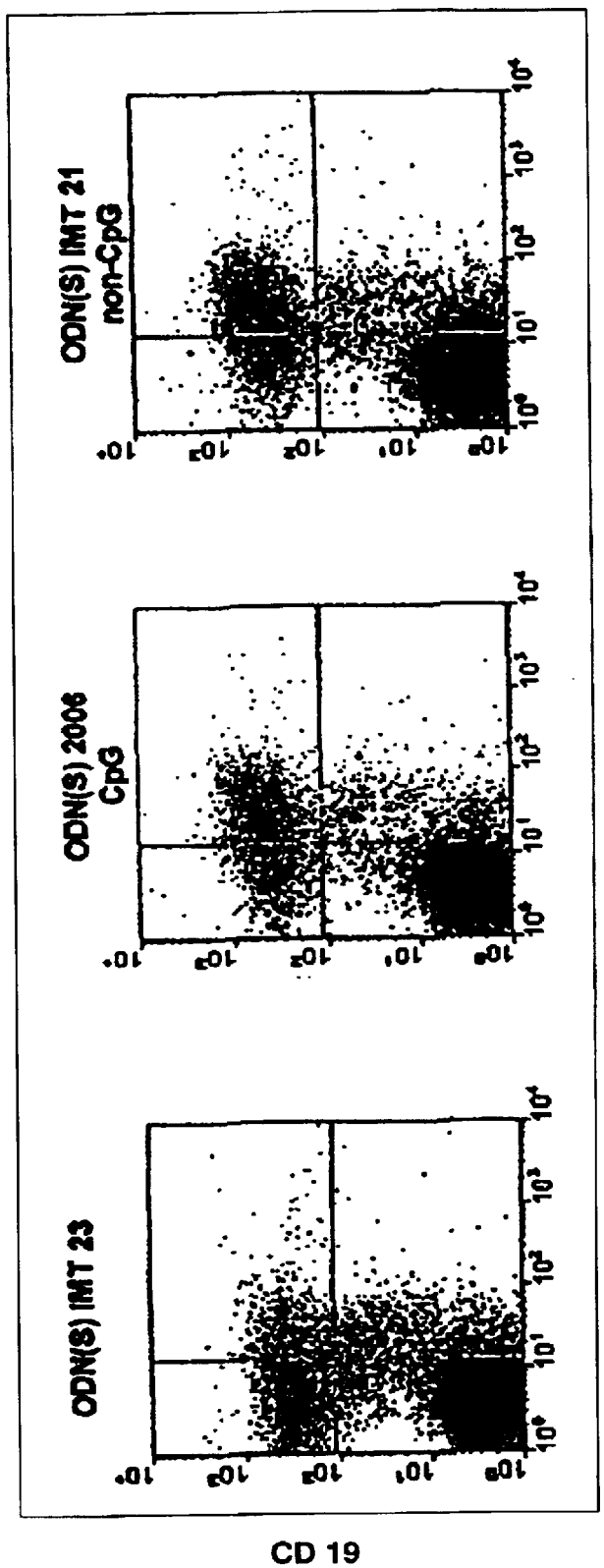
Figure 2B:
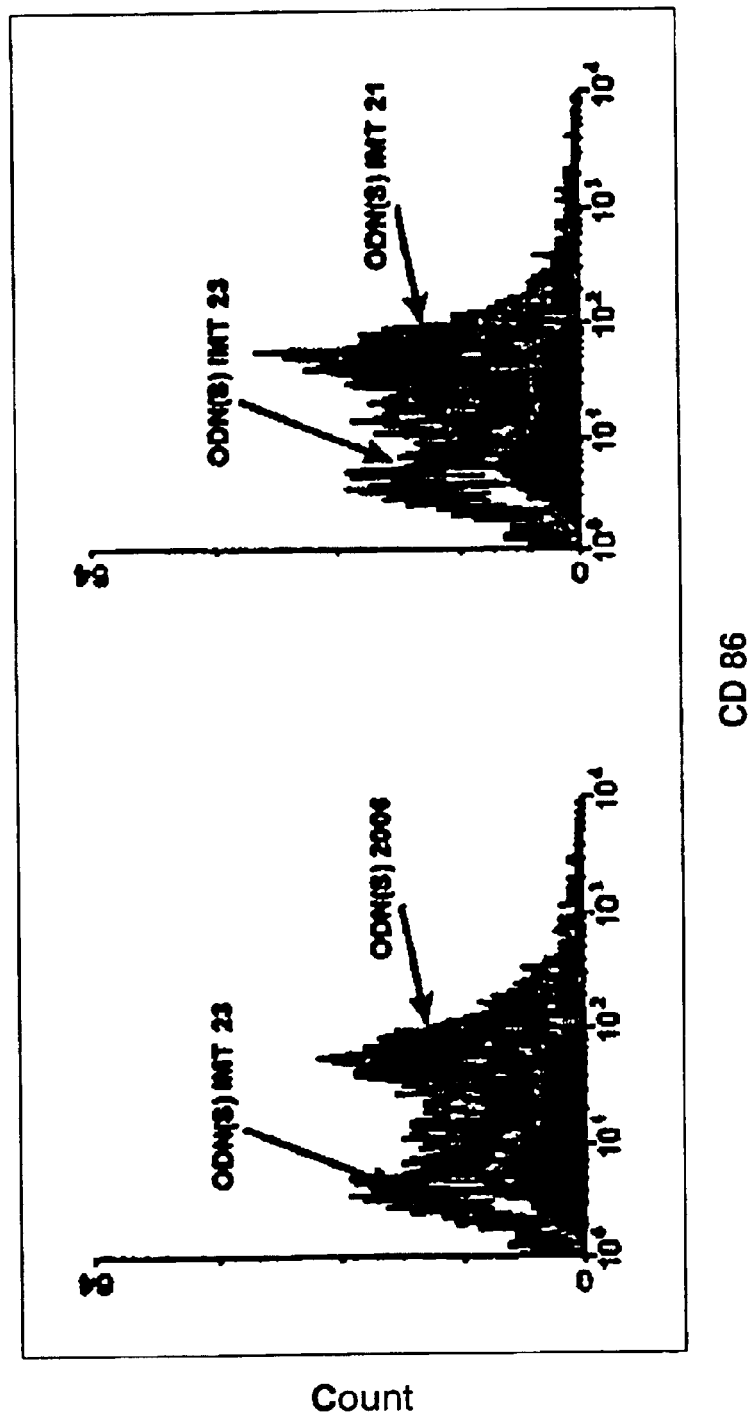

FIG. 2 shows the results from a flow cytometry study using human peripheral blood mononuclear leukocytes (PBMC) to determine the comparative effect of the phosphorothioate CpG ODN 2006:

5' TCGTCGTTTTGTCGTTTTGTCGTT 3' and the phosphorothioate non-CpG ODN IMT 021 (SEQ ID NO: 1)on activation of the B cell population:
(2a) Representative flow cytometry diagrams comparing B cell activation by IMT 023, 2006 and IMT 021 (2b) Representative histograms of the flow cytometry diagrams showed in (a).

Figure 3B:
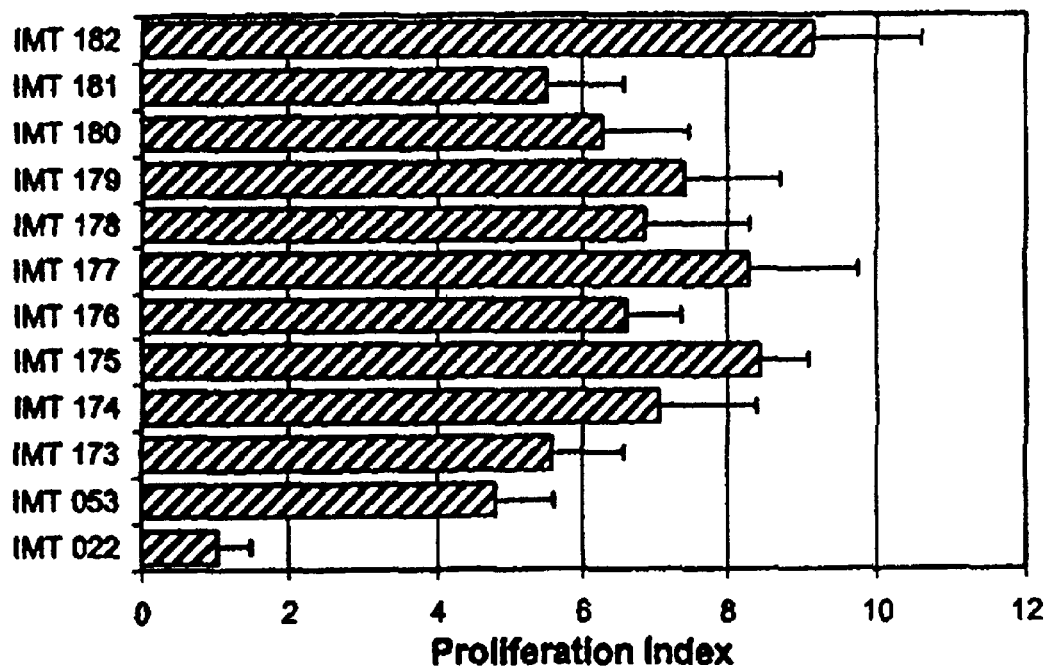
Figure 3C:
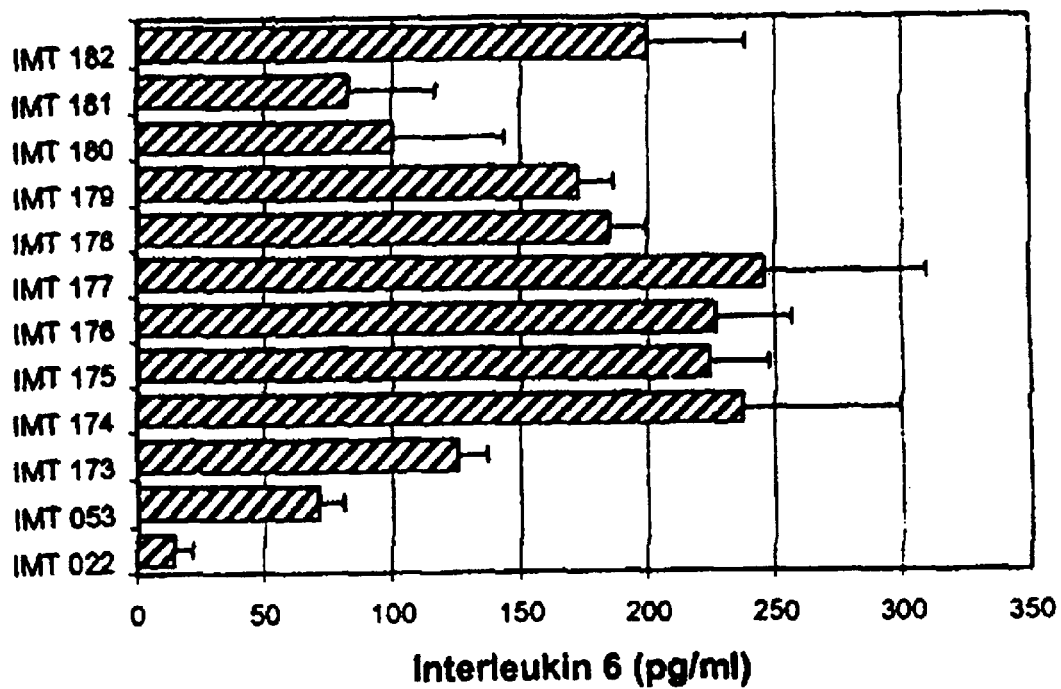

FIG. 3 shows the influence of the position of the immunostimulatory sequence motif (3a) $X_1X_2X_3X_4X_5X_6X_7X_8$ here disclosed on the immunostimulatory activity of non-CpG ODNs as measured by proliferation assay (3b) and IL-6 secretion assay (3c). Data represent the mean and standard deviation of three independent assays performed by quadruplicate each.

Figure 4A:
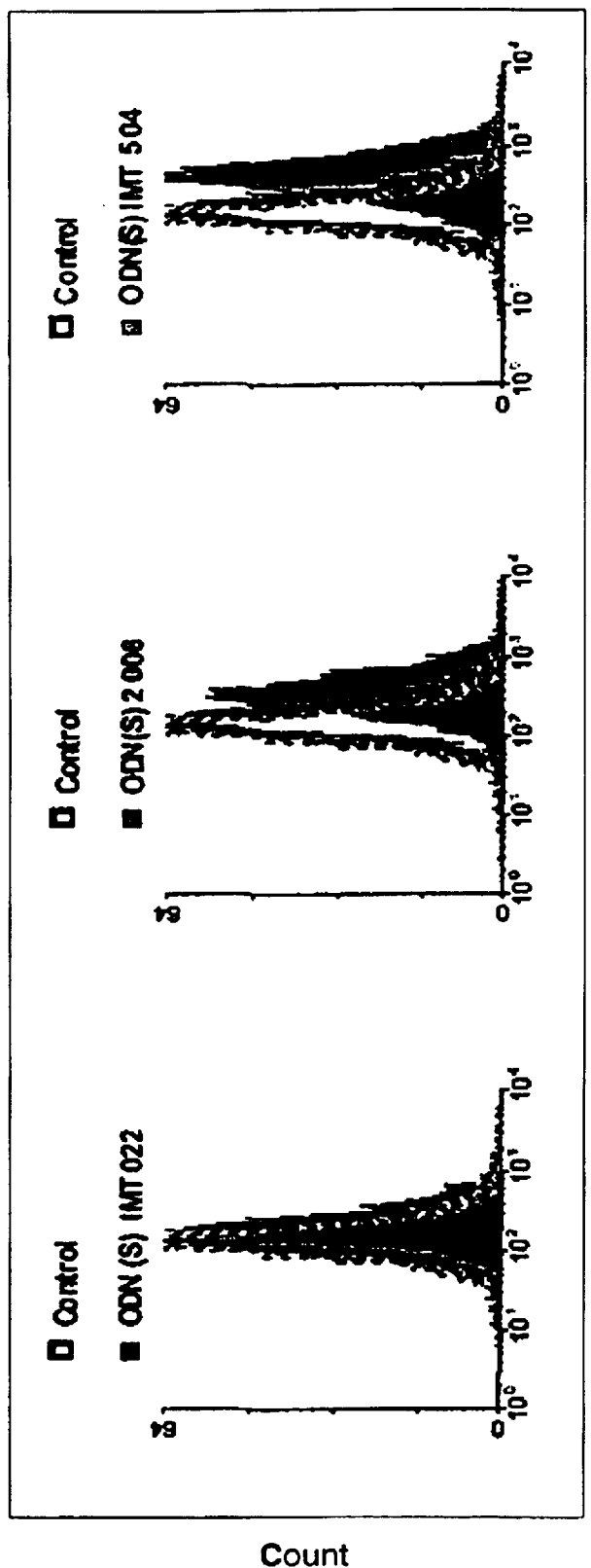
Figure 4B:
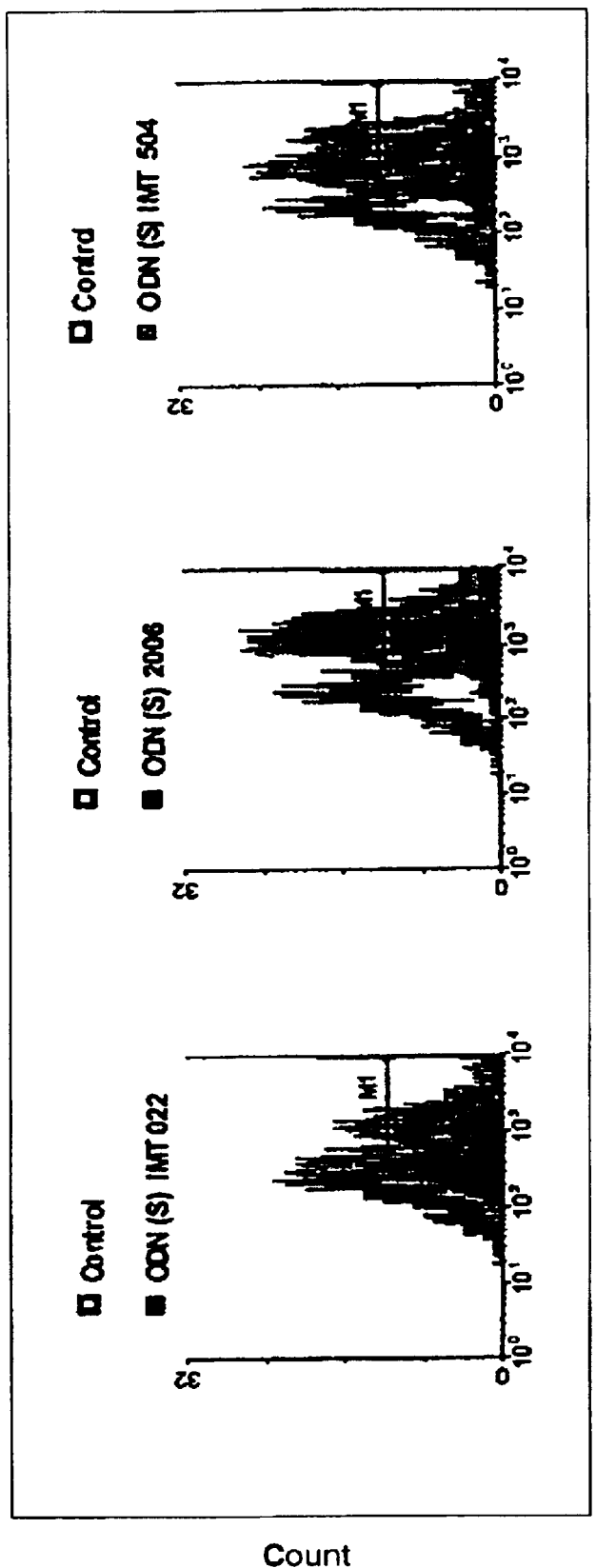
Figure 4C:
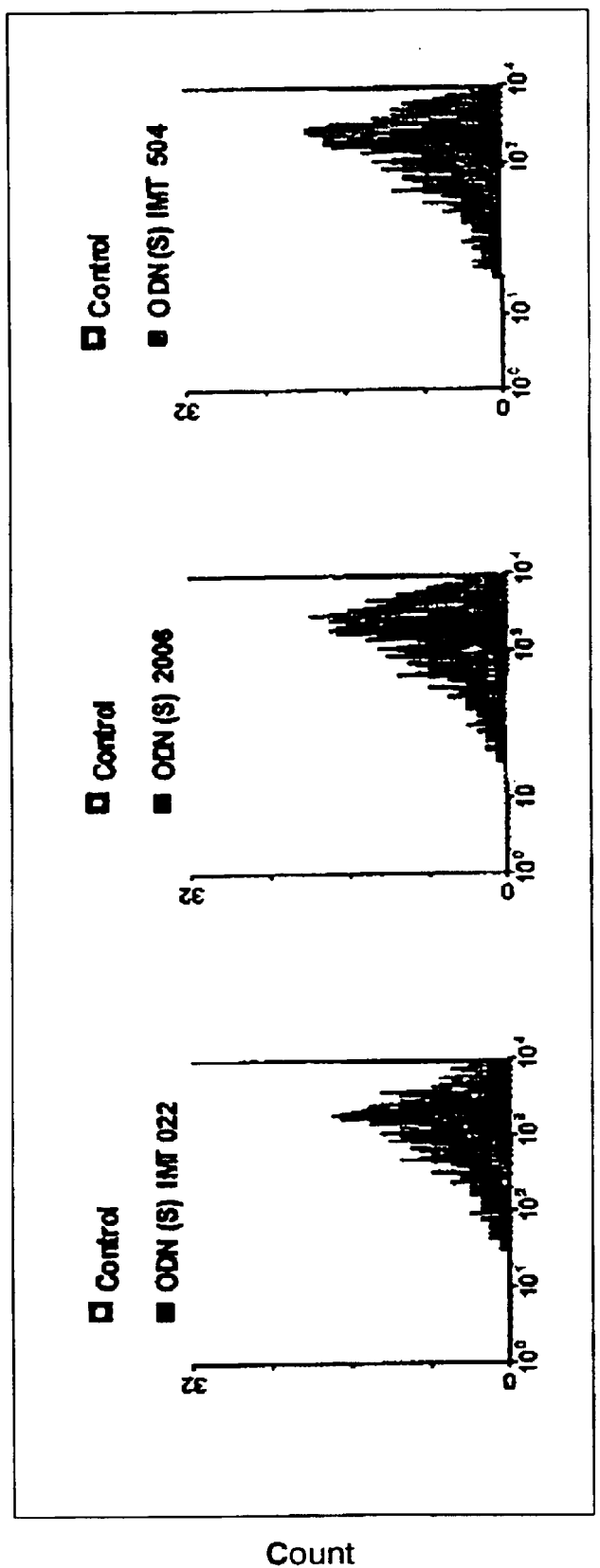

FIG. 4 shows the induction of CD40 (4a), MHC I (4b) and MHC II (4c) on CD19+ cells (B cells) by non-CpG-ODNs bearing the immunostimulatory sequence motif $X_1X_2X_3X_4X_5X_6X_7X_8$ here disclosed. Human PMBC were cultured for 24 hr with indicated ODNs and then stained with fluorescent anti-CD19/anti-CD40 (4a) or, anti-CD19/anti-MHC I (4b) or, anti-MHC II (4c). Flow cytometric results are presented as histograms. Open histograms correspond to cells cultured in absence of ODN and shaded histograms to cells cultured in presence of ODN. ODN (S) means phosphorothioate ODN.

Figure 5A:
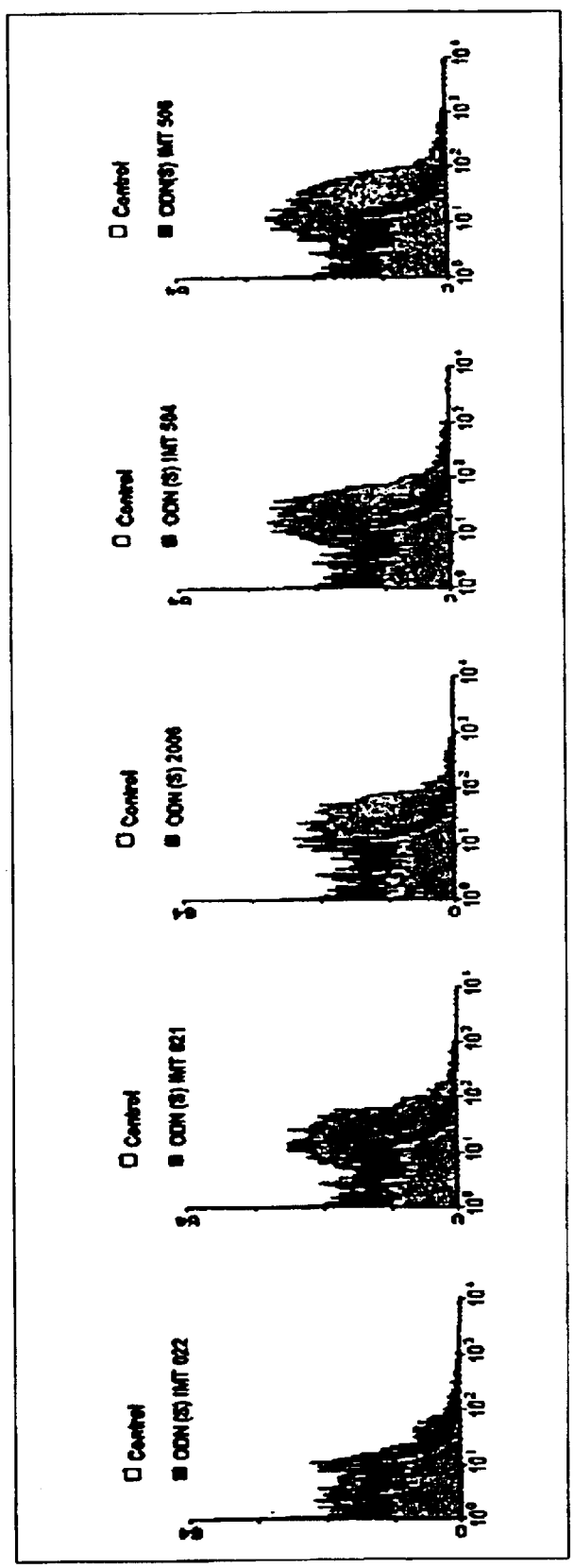
Figure 5B:
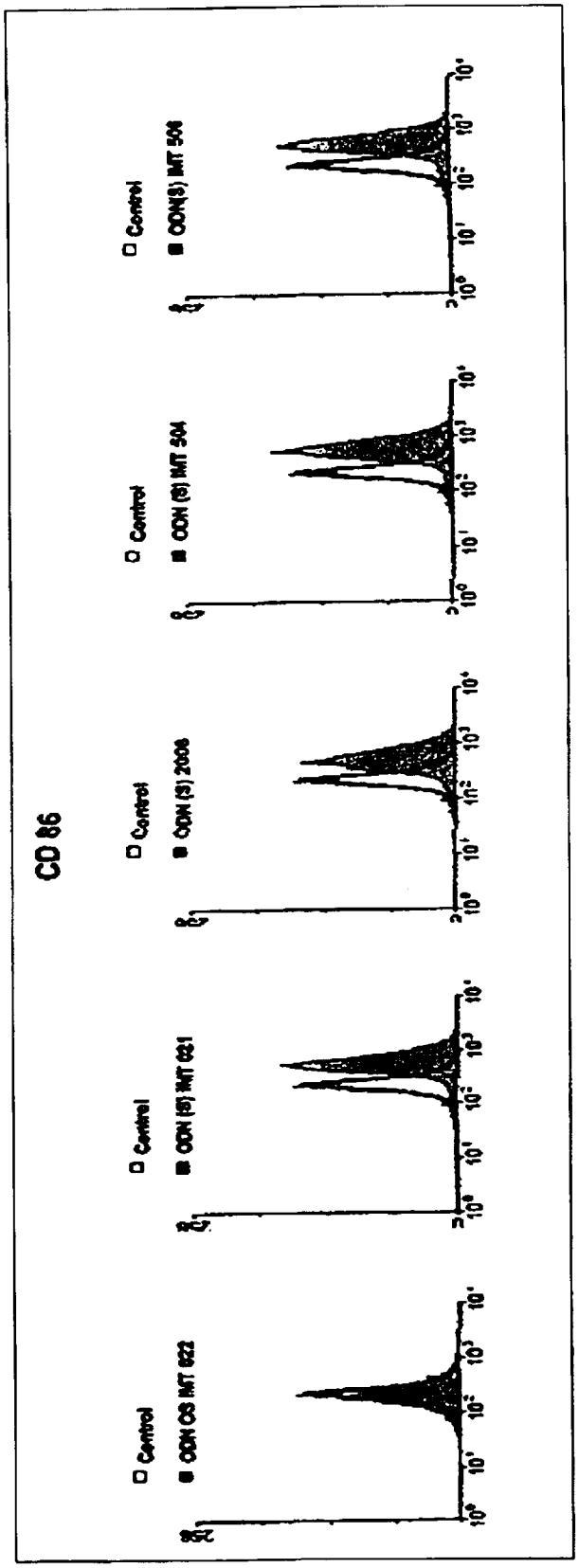
Figure 5C:
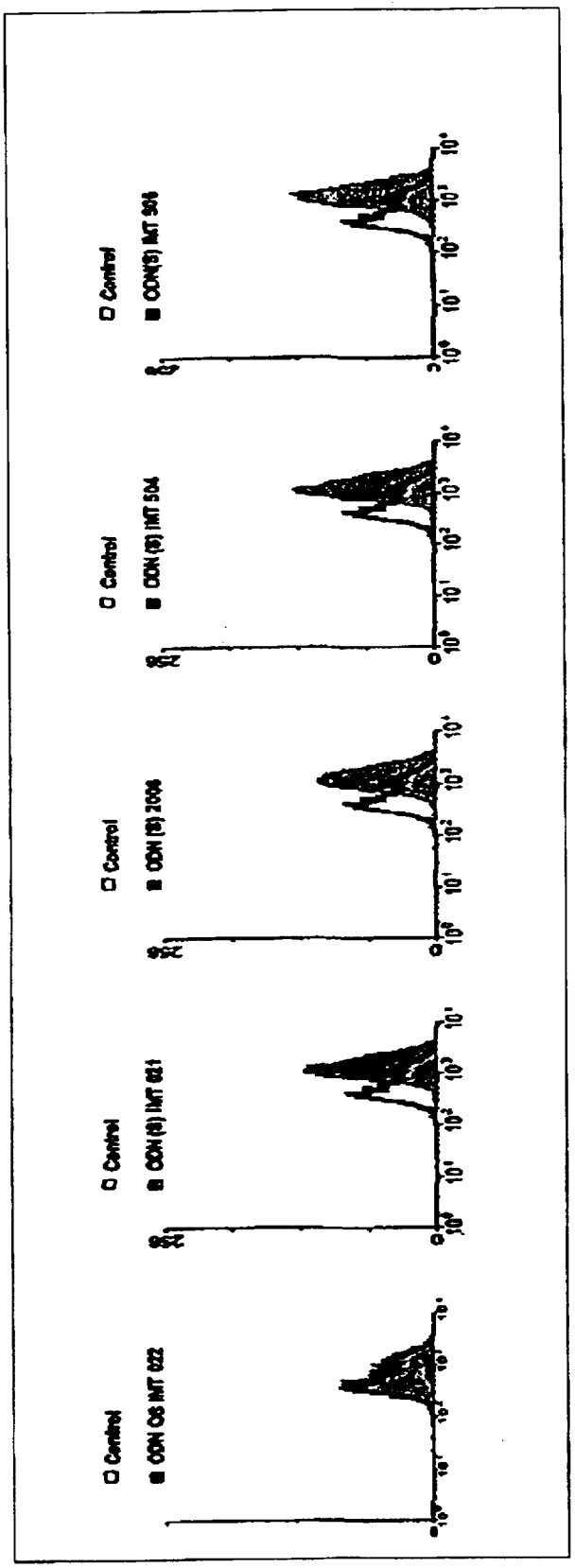

FIG. 5 shows the induction of CD86 (5a), CD40 (5b) and MHC I (5c) on purified B cells by non-CpG-ODNs bearing the immunostimulatory sequence motif $X_1X_2X_3X_4X_5X_6X_7X_8$ here disclosed. Human purified B cells were cultured for 24 hr with indicated ODNs and then stained with fluorescent anti-CD19/anti-CD86 (5a) or, anti-CD19/anti-CD40 (5b) or, anti-CD19/anti-MHC I (5c). Flow cytometric results are presented as histograms. Open histograms correspond to cells cultured in absence of ODN and shaded histograms to cells cultured in presence of ODN. ODN (S) means phosphorothioate ODN.

Figure 6A:
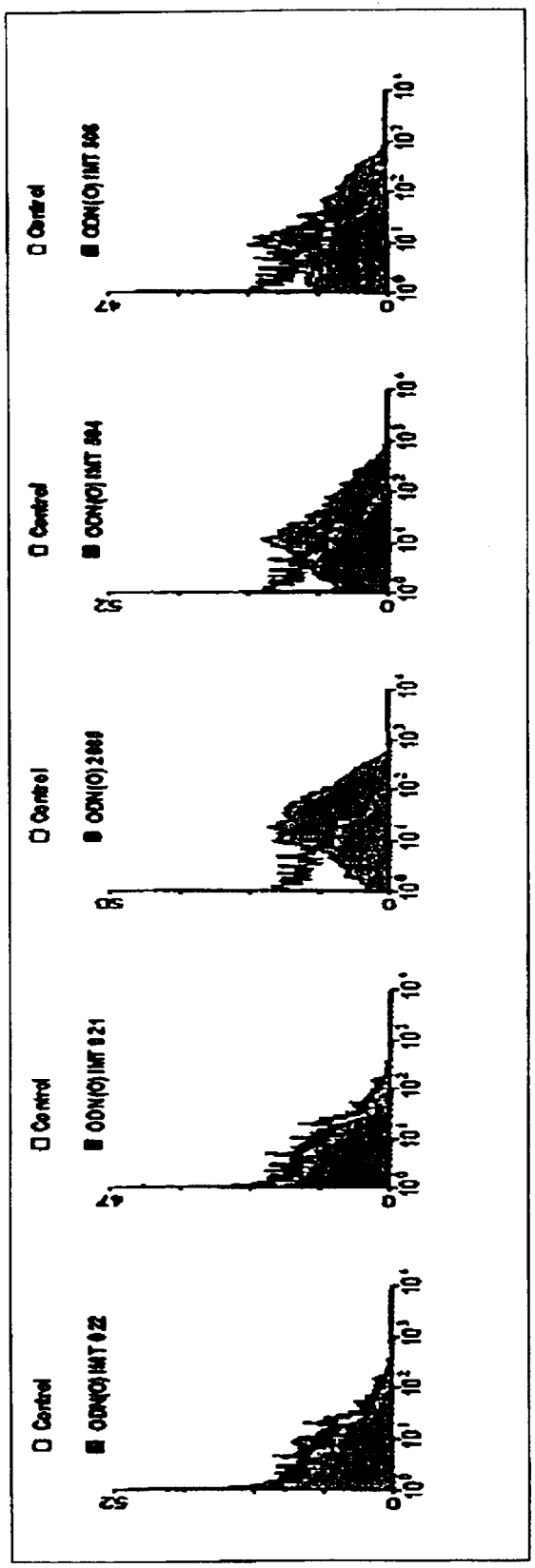
Figure 6B:
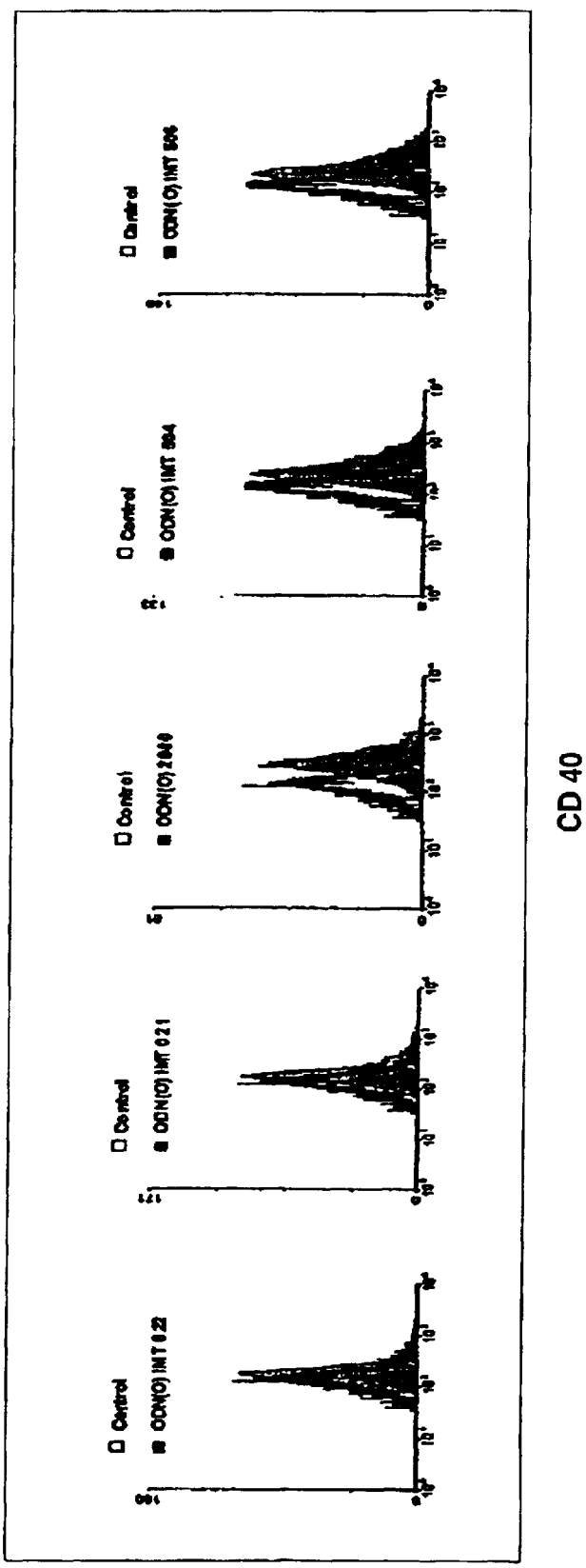
Figure 6C:
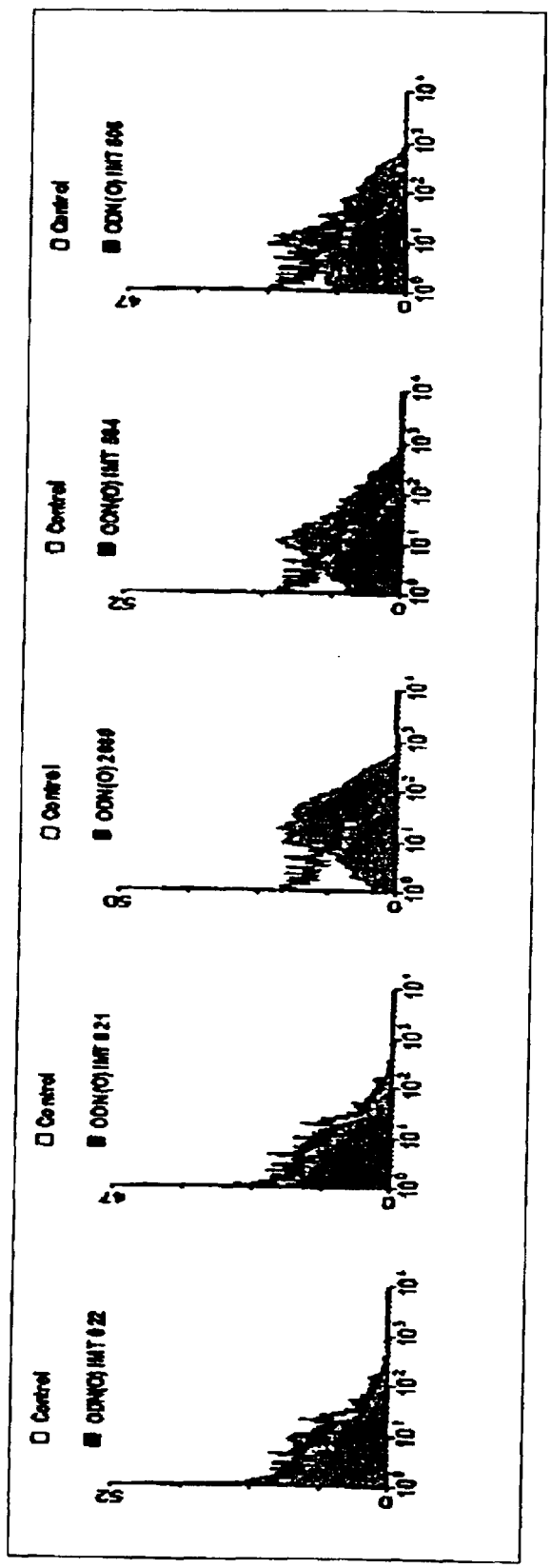

FIG. 6 shows induction of CD86 (6a), CD40 (6b) and MHC I (6c) in CD19+ cells (B cells) by phosphodiester non-CpG-ODNs bearing the immunostimulatory sequence motif $X_1X_2X_3X_4X_5X_6X_7X_8$ here disclosed. Human PMBC were cultured for 48 hr with indicated phosphodiester ODNs and then stained with fluorescent anti-CD19/anti-CD86 (6a) or, anti-CD19/anti-CD40 (6b) or, anti-CD19/anti-MHC I (6c). Flow cytometric results are presented as histograms. Open histograms correspond to cells cultured in absence of ODN and shaded histograms to cells cultured in presence of ODN. ODN (O) means phosphodiester ODN.

Figure 7A:
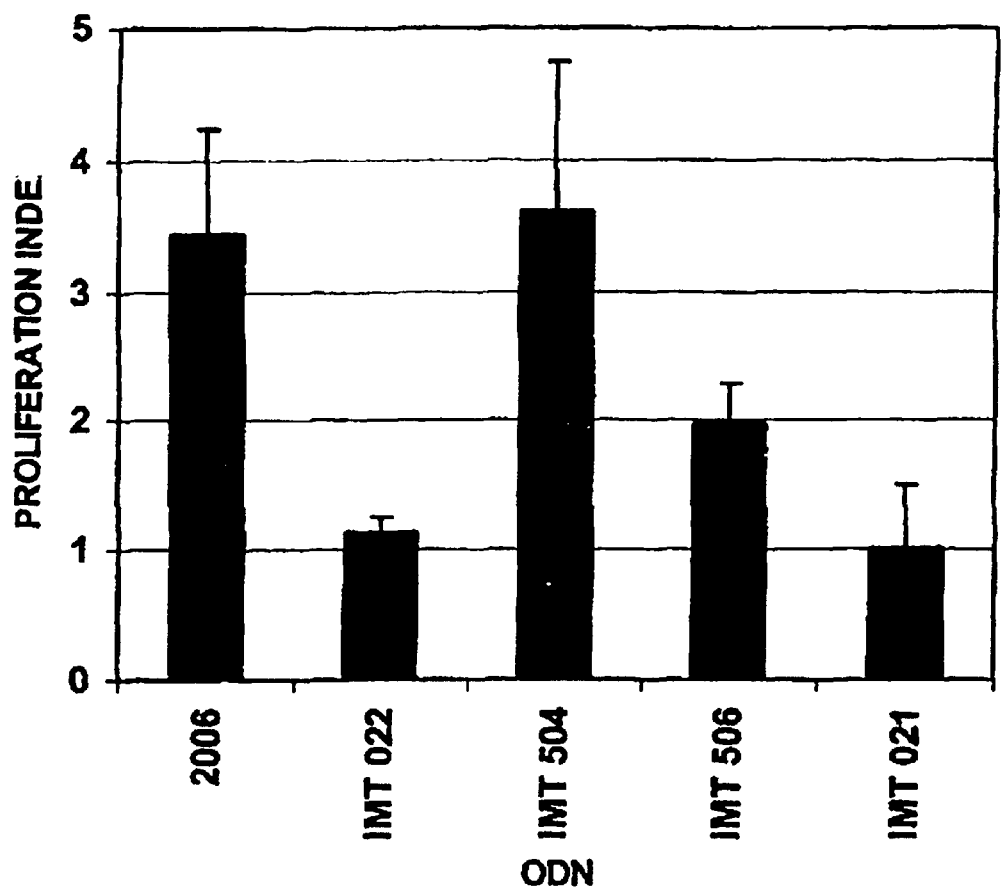
Figure 7B:
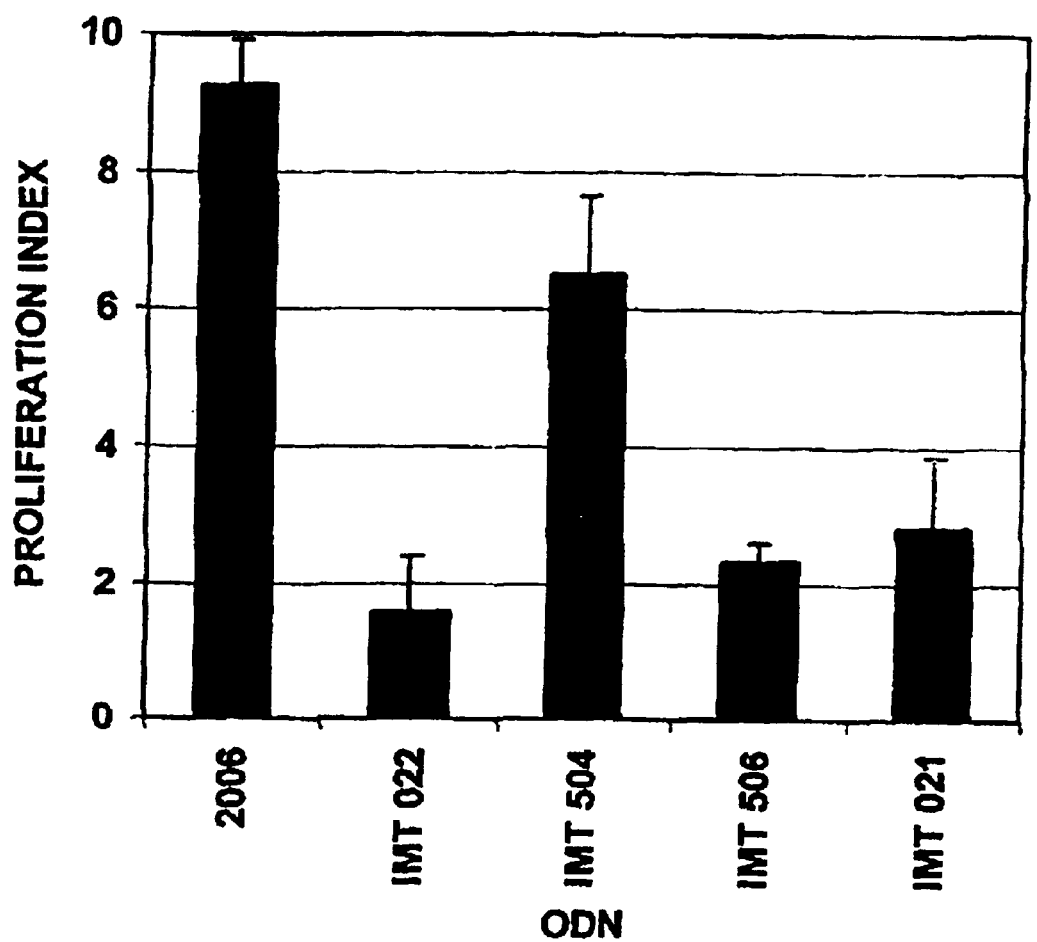

FIG. 7 shows stimulation of PMBC proliferation by non-CpG ODNs bearing the motif $X_1X_2X_3X_4X_5X_6X_7X_8$ here disclosed in non-human primates. *Cebus apella* (7a) or *Macacca fascicularis* PMBC (7b) were cultured for 72 hr with indicated ODNs (6 µg/ml). Data represent the mean and standard deviation of four replicates.

Figure 8A:
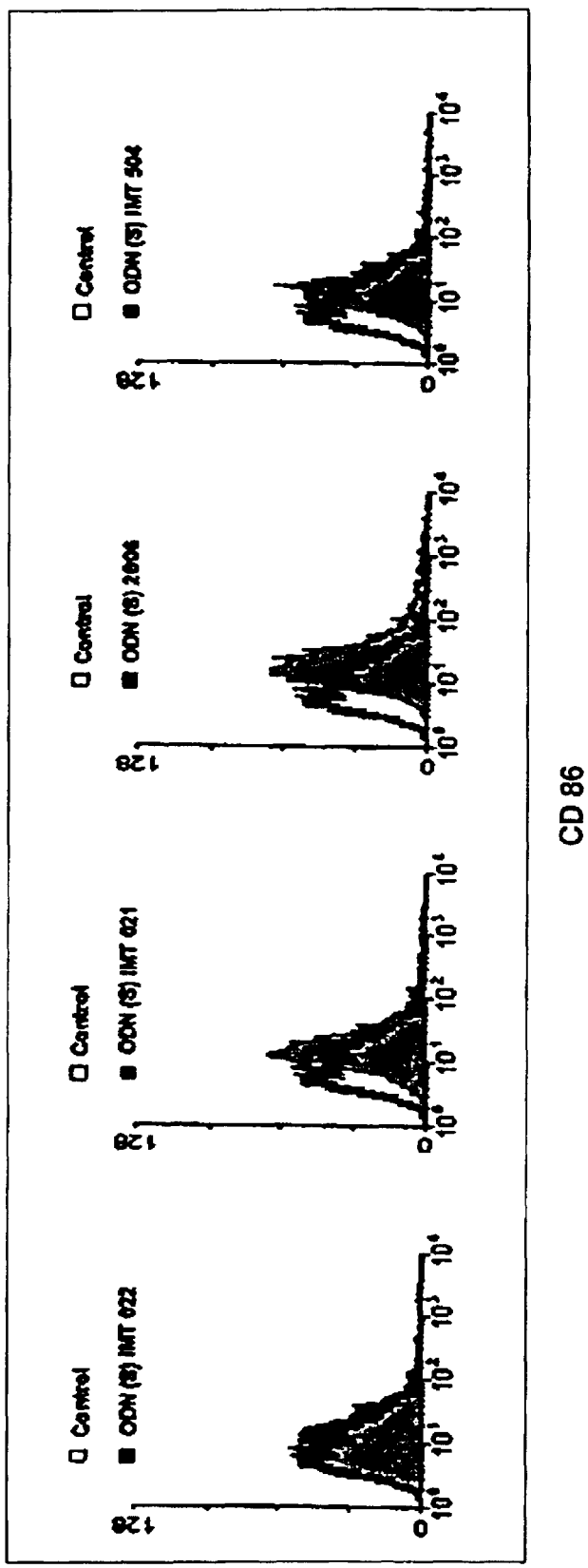
Figure 8B:
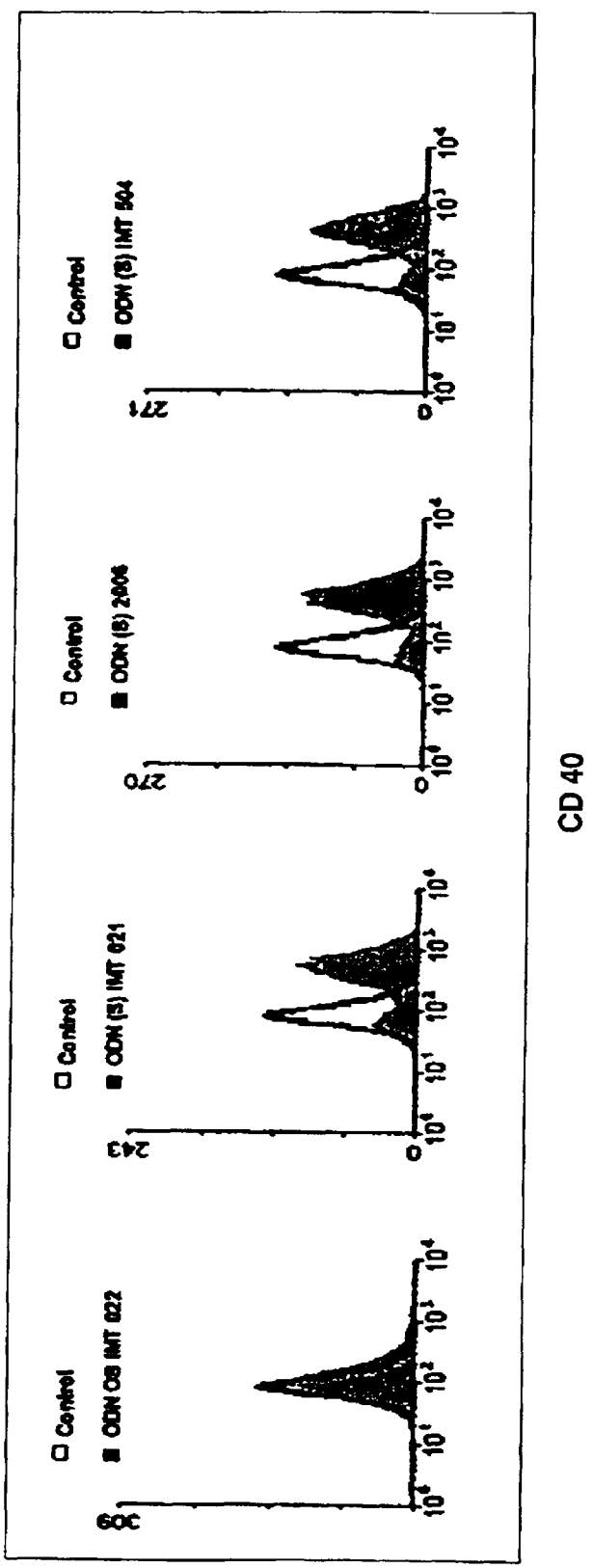
Figure 8C:
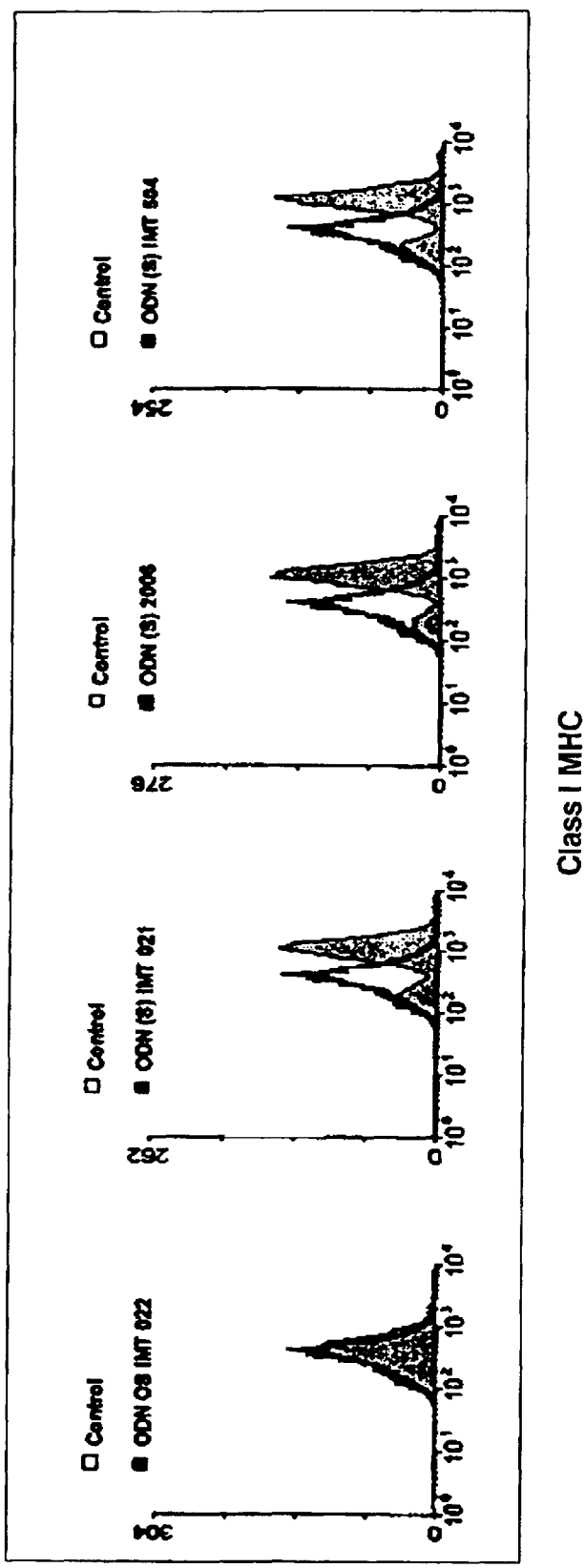

FIG. 8 shows the induction of CD86 (8a), CD40 (8b) and MHC I (8c) on CD 19+ (B cells) of a patient suffering B cell leukemia by non-CpG-ODNs bearing the motif $X_1X_2X_3X_4X_5X_6X_7X_8$ here disclosed. PMBC were cultured for 24 hr with indicated ODNs and then stained with fluorescent anti-CD19/anti-CD86 (8a) or, anti-CD19/anti-CD40 (8b) or, anti-CD19/anti-MHC I (8c). Flow cytometric results are presented as histograms. Open histograms correspond to cells cultured in absence of ODN and shaded histograms to cells cultured in presence of ODN. ODN (S) means phosphorothioate ODN.

Figure 9A:
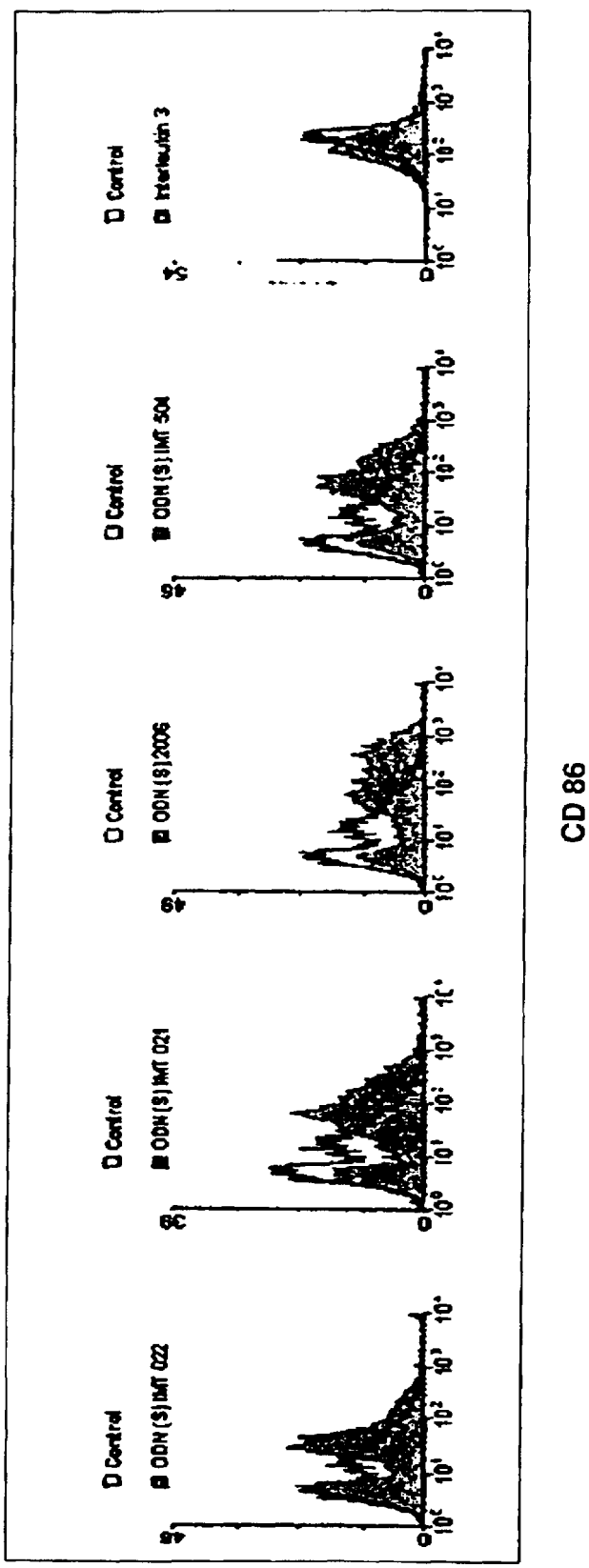
Figure 9B:
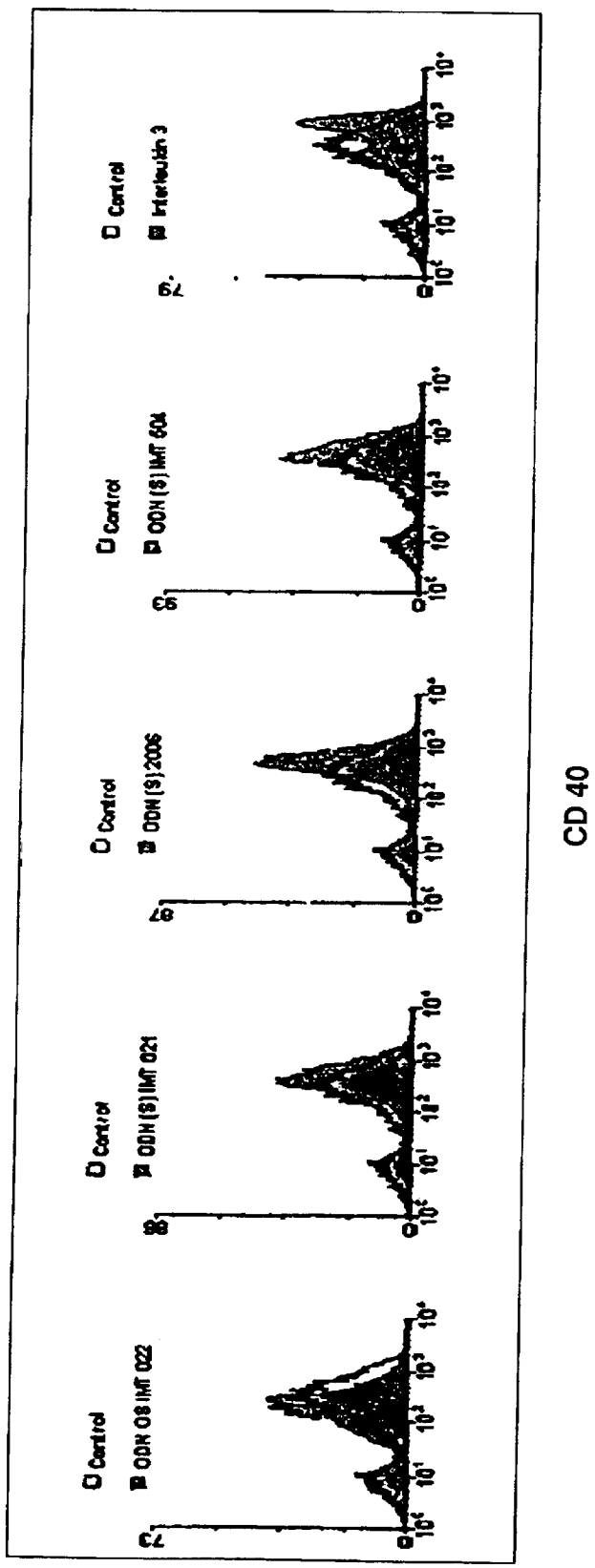
Figure 9C:
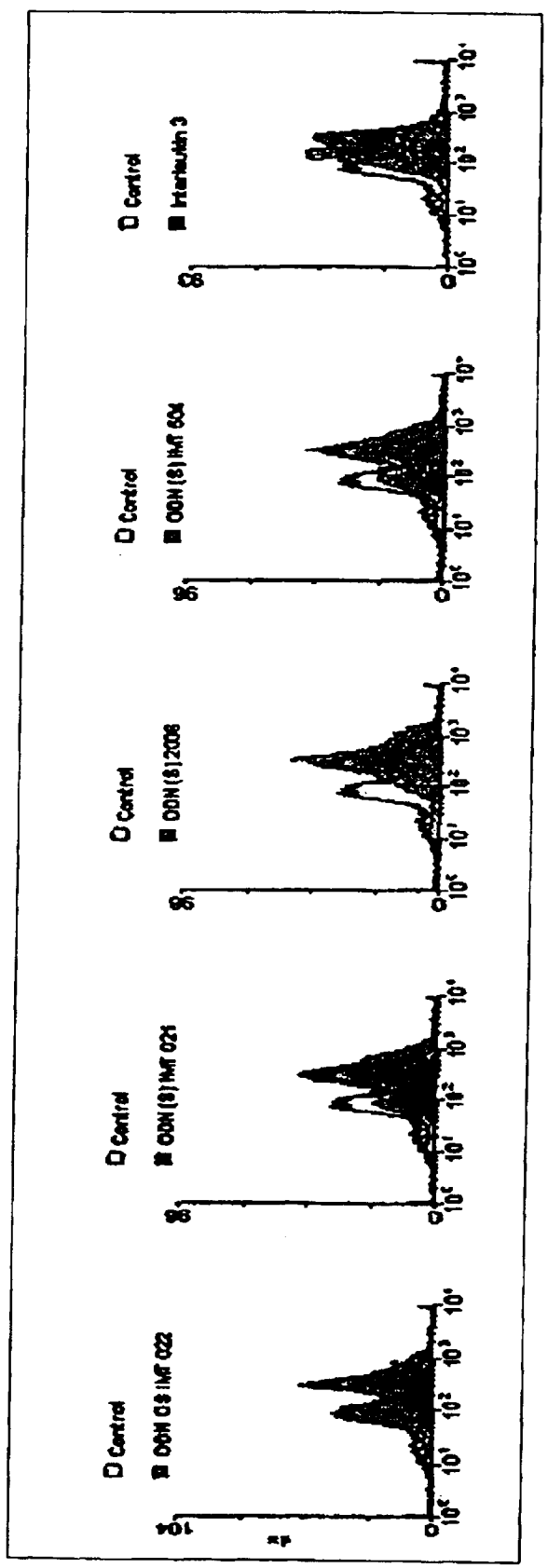

FIG. 9 shows the induction of CD86 (9a), CD40 (9b) and MHC I (9c) on purified plasmacytoid dendritic cells by non-CpG-ODNs bearing the motif $X_1X_2X_3X_4X_5X_6X_7X_8$ here disclosed. More than 95% pure plasmacytoid dendritic cells were cultured for 24 hr with indicated ODNs and then stained with fluorescent anti-CD19/anti-CD86 (9a) or, anti-CD19/anti-CD40 (9b) or, anti-CD19/anti-MHC I (9c). Flow cytometric results are presented as histograms. Open histograms correspond to cells cultured in absence of ODN and shaded histograms to cells cultured in presence of ODN. ODN (S) means phosphorothioate ODN.

DETAILED DESCRIPTION OF THE INVENTION

Definitions:

An "allergy" refers to acquired hypersensitivity to a substance (allergen). Examples of allergies are eczema, allergic rhinitis, asthma and urticaria.

An "immune system deficiency" refers to a disease in which the immune system is not functioning in normal capacity.

As used herein, the term "oligonucleotide" or "oligo" shall mean multiple nucleotides (i.e. molecules comprising a sugar (e.g. ribose or deoxyribose) linked to a phosphate group and to an exchangeable organic base, which is either a substituted pyrimidine (e.g. cytosine (C), thymine (T) or uracil (U)) or a substituted purine (e.g. adenine (A) or guanine (G)). The term "oligonucleotide" as used herein refers to both oligoribonucleotides (ORNs) and oligodeoxyribonucleotides (ODNs). The term "oligonucleotide" shall also include oligonucleosides (i.e. an oligonucleotide minus the phosphate) and any other organic base containing polymer. Oligonucleotides can be obtained from existing nucleic acid sources (e.g. genomic or cDNA), but are preferably synthetic (e.g. produced by oligonucleotide synthesis)

An "oligonucleotide" refers to multiple nucleotides linked by phosphodiester bonds.

An "immunostimulatory oligonucleotide" refers to an oligonucleotide which stimulates, (i.e. has a mitogenic effect on, or induces or increases cytokine expression by) a cell of the immune system (ie: a lymphocyte, a macrophage).

A "CpG" refers to an unmethylated cytosine-guanine dinucleotide.

A "CpG oligonucleotide" refers to an oligonucleotide which stimulates a cell of the immune system and its immunostimulatory activity critically depends of the presence of at least one CpG in its sequence.

A "non-CpG oligonucleotide" refers to an oligonucleotide which stimulates a cell of the immune system and its immunostimulatory activity does not critically depends of the presence of a CpG in its sequence.

A "subject" refers to an animal of the order Primate, including humans.

As used herein, the term "treating" refers to a process by which the symptoms of a disease, and more particularly infectious diseases or tumoral diseases or immunological disorders are ameliorated or completely eliminated.

As used herein, the term "preventing" refers to a process by which a disease, and more particularly infectious diseases or tumoral diseases or immunological disorders are obstructed or delayed.

In a preferred embodiment, the immunostimulatory oligonucleotides of the invention are advantageously modified into stabilized oligonucleotides. Such stabilized immunostimulatory oligonucleotide may be particularly useful to obtain a prolonged immunostimulation. As used herein, a "stabilized oligonucleotide" refers to an oligonucleotide that is relatively resistant to in vivo degradation (e.g. via an exo- or endo-nuclease). Preferred stabilized oligonucleotides of the present invention comprise a phosphate backbone modification. More particularly, the phosphate backbone modification is preferably a 5' inter-nucleotide linkage modification, for instance, at the first two nucleotides of the 5' end of the oligonucleotide of the invention. Furthermore, the phosphate backbone modification may be a 3' inter-nucleotide linkage modification. In such a case, the modification may occur, for instance, at the last two nucleotides of the 3' end of the oligonucleotide of the invention. Even more preferably, the immunostimulatory oligonucleotide of the invention may be stably modified so as to comprise a phosphorothioate-linked nucleotide (i.e. at least one of the phosphate oxygens is replaced by sulfur). In the most preferred embodiment, most if not all the nucleotides of the immunostimulatory oligonucleotides of the invention comprise a phosphorothioate-linked nucleotide.

Other stabilized oligonucleotides may alternatively include: nonionic DNA analogs, such as alkyl- and aryl-phosphonates (in which the charged phosphonate oxygen is replaced by an alkyl or aryl group), phosphodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

Description:

The present invention provides methods to augment the immune response of animals of the order Primate, including humans, adding to vaccines one or more of the oligonucleotides of this invention or performing a treatment based in the administration of one or more of the oligonucleotides of this invention to a person with a tumoral disease or an immunological disorder or contacting white blood cells obtained from a person with a tumoral disease or an immunological disorder with one or more of the oligonucleotides of this invention "ex vivo", and readministering these activated white blood cells to the same person.

Vaccines compositions useful containing one or more of the oligonucleotides of this invention can present antigens directly (i.e., in the form of a defined protein or polysaccharide) or as a part of a complex biological entity (i.e. complete viruses; complete bacterial cells; bacterial membranes or artificial conjugates like polysaccharide-protein conjugates). These antigens can be combined in multiple vaccines.

A vaccine composition including at least one antigen is formulated to include one or more of the oligonucleotides of this invention.

For example the antigen can be *Moraxella catharralis* killed cells or subcellular fractions of these cells or Hepatitis B virus surface antigen natural or produced by means of the DNA recombinant technology.

One or more of the oligonucleotides of this invention may be formulated alone or together with one or more antigens in a pharmaceutical composition, which may also include carriers, thickeners, diluents, buffers, preservatives, surface active agents, anti-microbial agents, anti-inflammatory agents, anesthetics and the like. The formulation can be liquid or lyophilized. The pharmaceutical composition may be administered in a number of ways depending of whether local or systemic treatment is desired, and on the area to be treated. Administration may be done topically, orally, by inhalation or parenterally. Formulation for topical administration may include ointments, lotions, creams, gels, drops, suppositories, sprays, liquids and powders. Pharmaceutical carriers, aqueous, powder or oily bases, thickeners and the like may be necessary or desirable. Formulations for oral administration include powders or granules, suspensions or solutions in water or non-aqueous media, capsules, tablets and the like. Thickeners, flavorings, diluents, emulsifiers and the like may be necessary or desirable. Formulations for parenteral administration include sterile aqueous solutions, which may also contain buffers, diluents and other additives. A vaccine containing one or more antigens and one or more of the oligonucleotides of this invention can be formulated and used for prophylactic or therapeutic purposes.

Common antigens used in viral prophylactic vaccines are from Hepatitis B virus, Hepatitis A virus and Influenza virus. Common antigens used in bacterial prophylactic vaccines are from *Streptococcus pneumoniae, Haemophilus influenzae, Moraxella catharralis, Klebsiella pneumoniae* and *Mycobacterium bovis* (*BCG*). Common antigens used in therapeutic vaccines are from Papilloma virus, HIV virus and melanoma cells.

A further refinement of a vaccine formulation is to incorporate one or more of the oligonucleotides of this invention as adjuvant/s and the antigen/s into a delivery vehicle to provide for delayed release of the active compounds of the vaccine over time. This can be accomplished by various means known in the art. Examples of these means are encapsulation into Poly (lactide-coglicolide) micro particles (Kersten, G. F. A. and Gander, B. 1996. Biodegradable Micro Spheres as vehicles for antigens, in: S. H. E. Kaufmann, ed. Concepts in Vaccine Development. Walter de Gruyter. Berlin-N.Y.), liposomes (Gregoriadis, G. et al. 2000. Liposomes as Immunological Adjuvants and Vaccine Carriers, in: S. H. E. Kaufmann, ed. Concepts in Vaccine Development. Walter de Gruyter. Berlin-N.Y.) and poly (methyl methacrylate) nanoparticles (Kreuter, J. 2000. Poly (Methyl Methacrylate) nanoparticles as vaccine adjuvants, in: S. H. E. Kaufmann, ed. Concepts in Vaccine Development. Walter de Gruyter. Berlin-N.Y.).

Another refinement of the vaccine formulation is to conjugate the antigen/s and one or more of the oligonucleotides of this invention, by chemical means (Mier W, Eritja R, Mohammed A, Haberkorn U, Eisenhut M. 2000. Preparation and evaluation of tumor-targeting peptide-oligonucleotide conjugates. Bioconjug. Chem. 11:855).

Many vaccine formulations are known in the art and can be used by substituting one or more of the oligonucleotides of this invention for the adjuvant previously known or by simply adding one or more of the oligonucleotides of this invention to the original formulation.

Based on their immunostimulatory properties, one or more of the oligonucleotides of this invention can also be administered to a subject in vivo to treat a tumoral disease or an immune system disorder.

Examples of common tumoral diseases are: Chronic Myelogenous Leukemia, Melanoma, Kaposi's Sarcoma, Multiple Myeloma, Renal Cell Carcinoma, Bladder Cancer, Lung Cancer, Skin Cancer, Brest Cancer, Colon Cancer and Uterus Cancer. Examples of common immunological disorders are: Allergy, Severe Combined Immunodeficiency, Chronic Granulomatous disease, and Acquired Immunodeficiency Disease.

The pharmaceutical composition for these treatments may include one or more of the oligonucleotides of this invention together with carriers, thickeners, diluents, buffers, preservatives, surface active agents, anti-microbial agents, anti-inflammatory agents, anesthetics and the like. The formulation can be liquid or lyophilized.

The pharmaceutical composition may be administered in a number of ways depending of whether local or systemic treatment is desired, and on the area to be treated. Administration may be done topically, orally, by inhalation or parenterally. Formulation for topical administration may include ointments, lotions, creams, gels, drops, suppositories, sprays, liquids and powders. Pharmaceutical carriers, aqueous, powder or oily bases, thickeners and the like may be necessary or desirable. Formulations for oral administration include powders or granules, suspensions or solutions in water or non-aqueous media, capsules, tablets and the like. Thickeners, flavorings, diluents, emulsifiers and the like may be necessary or desirable. Formulations for parenteral administration include sterile aqueous solutions, which may also contain buffers, diluents and other additives. Alternatively, one or more of the oligonucleotides of this invention can be contacted with immunocompetent cells (i.e. B cells or plasmacytoid dendritic cells) obtained from a subject having a tumoral disease or an immune system deficiency "ex vivo" and activated cells can then be reintroduced in the subject.

EXAMPLE 1

Materials and Methods

The following materials and methods were used generally throughout the examples.

1) Oligonucleotides

Oligonucleotides having phosphorothioate internucleotide linkages were purchased, purified by high-pressure liquid chromatography (HPLC), from Operon Technologies (Alameda, Calif.) or Annovis (Aston, Pa.) or Oligos Etc (Bethel, Me.). Oligonucleotides were suspended in depyrogenated water and kept at −20° C. until used.

2) Antibodies

Antibodies used in assays were purchased from Serotec (Raleigh, N.C.).

3) Peripheric Blood Mononuclear Leukocytes (PBMC)

Blood was obtained by venipuncture from healthy donors using heparin as anticoagulant. PMBC were isolated by Ficoll-Hypaque (Sigma Diagnostics Inc., St. Louis, Mo.) density gradient centrifugation. Briefly, blood samples diluted 1:2 in RPMI-1640 medium (PAA laboratories GmbH, Linz, Austria) supplemented with 2.0 mM L-glutamine and 50.0 µg/ml gentamicin and 20 mM HEPES were centrifuged at 1000×g for 40 minutes at 20° C. PMBC were isolated, washed and suspended in medium supplemented with 10% fetal calf serum.

4) Purification of Cells

B lymphocytes and plasmacytoid dendritic cells were purified from human PMBC by positive selection using the MACS magnetic cell separation systems (Miltenyi Biotec, Germany).

5) Cell Proliferation Assays

Blood was obtained by venipuncture from healthy donors using heparin as anticoagulant. PMBC were isolated by Ficoll-Hypaque (Sigma Diagnostics Inc., St. Louis, Mo.) density gradient centrifugation. Briefly, blood samples diluted 1:2 in RPMI-1640 medium (PAA laboratories GmbH, Linz, Austria) supplemented with 2.0 mM L-glutamine and 50.0 µg/ml gentamicin and 20 mM HEPES were centrifuged at 1000×g for 40 minutes at 20° C. PMBC were isolated, washed and suspended in medium supplemented with 10% fetal calf serum.

6) IL6 Assay

PBMC ($3 \times 10^5$/well) were cultured as described above with ODNs (6 µg/ml) for 24 hr. After this, supernatants were collected and IL6 levels measured by ELISA. Briefly, 96 well micro titer plates (NUNC, Denmark) were coated with anti-IL6 antibodies and blocked with RPMI 1640 media supplemented with 10% (v/v) heat inactivated FCS. IL6 was detected calorimetrically using biotin-labeled antibodies followed by peroxidase-conjugated strepto-avidin and then peroxidase-specific calorimetric substrate. Standard curves were generated using known amounts of recombinant IL6. The detection limit of these assays was 30 pg/ml. All assays were performed in duplicate.

6) IgM Secretion Assay

PBMC ($3 \times 10^5$/well) were cultured as described above with ODNs (1.5 µg/ml) for 72 hr. After this, supernatants were collected and IgM assayed by ELISA. Briefly, 96 microtiter plates (NUNC, Denmark) were coated with anti-IgM antibodies and blocked with RPMI 1640 media. IgM was detected calorimetrically using peroxidase-labeled antibodies followed by peroxidase-specific calorimetric substrate. Standard curves were generated using known amounts of purified IgM. The detection limit of these assays was 50 ng/ml. All assays were performed in duplicate.

6) Flow Cytometry

Staining of surface antigens was performed as described (J. Fló and E. Massouh. Age-related changes of native and memory CD4 rat lymphocyte subsets in mucosal and systemic lymphoid organs. Developmental and comparative Immunology 21: 443–453, 1997). Anti CD19 (Clone LT19), CD86 (Clone BU63), CD40 (clone LOB 7/6), CD4 (clone S 3.5), MHC class I (Clone W6/32) and MHC class II (Clone WR 18) antibodies were purchased from Serotec (Raleigh, N.C., USA).

Flow cytometric data of 10,000 cells/sample were acquired on a FACScan (Becton Dickinson Immunocytometry Systems, San Jose, Calif.). Data were analyzed using the computer program Win MDI, 2.8, Interface Flow Cytometry Application (Joseph Trotter Copyright 1993–1998).

7) Immunization of Monkeys Against Hepatitis B Surface Antigen (HBsAg) and Evaluation of the Humoral Response Twelve monkeys of the species *Cebus Apella* (2.5–3.5 Kg) were immunized with a pediatric dose of AgB (Pablo Cassara, Buenos Aires, Argentina) containing 10 μg of HBsAg adsobed to alumina (25 mg of $Al^{3+}$/mg of HBsAg). This was administered alone (n=3, 1 female, 2 males) or combined with indicated phosphorothioate ODN (150 μg/dose) (n=3, 1 female, 2 males). All vaccines were administered intramuscular (i.m.) in the quadriceps muscle in a total volume of 1 ml. Monkeys were maintained in the animal facility of the CEMIC (Centro Medico de Investigaciones Clinicas), Buenos Aires, Argentina. Animals were monitored daily by specialists and weighed once per week. Plasma was recovered by intravenous (i.v.) puncture before and at various times after immunization and immediately assayed for antibodies using the commercial kit AUSAB (Abbot Laboratories, Illinois, USA). Titers are expressed in milliinternational units per ml.

EXAMPLE 2
Selection of Oligonucleotide Sequences

WO 96/02555 and U.S. Pat. No. 6,239,116 patents teach that to be immunostimulatory, oligonucleotides require sequences containing unmethylated CpG motifs (WO 96/02555, col. 13 lines 19–20 and U.S. Pat. No. 6,239,116, col. 6 lines 1–3). EP 0 468 520 teaches that to be immunostimulatory, oligonucleotides require a palindromic sequence of at least 6 nucleotides long to be satisfactory (EP 0 468 520, col. 11, lines 34–37). Therefore, several non-CpG oliqonucleotides, without palindromic sequences of at least 6 nucleotides long were probed using proliferation assays, cell differentiation assays, cytokine IL6 secretion assays and IgM secretion assays performed on human peripheral blood mononuclear leukocytes (PBMC). As a positive control, the CpG oligonucleotide 2006 of composition:

5' TCGTCGTTTTGTCGTTTTGTCGTT 3' and phosphorothioate bonds described by Hartman and Krieg (Hartmann, G., Krieg, A. M. 2000. Mechanism and function of a newly identified CpG DNA motif in human primary B cells. J. Immunol. 164:944.) was used. As a background control the phosphorothioate oligonucleotide IMT 023 (SEQ ID No 9) or IMT 022 (SEQ ID No 8) with very low activity on human cells were used.

Also as a "presumably" negative control an oligonucleotide with the same composition of the oligonucleotide 2006 but in which all the CpG dinucleotides have been replaced by GpC dinucleotides:

5' TGCTGCTTTTGTGCTTTTGTGCTT 3' was used. This oligonucleotide was named ODN IMT 021 (SEQ ID No 1).

Figure 1:
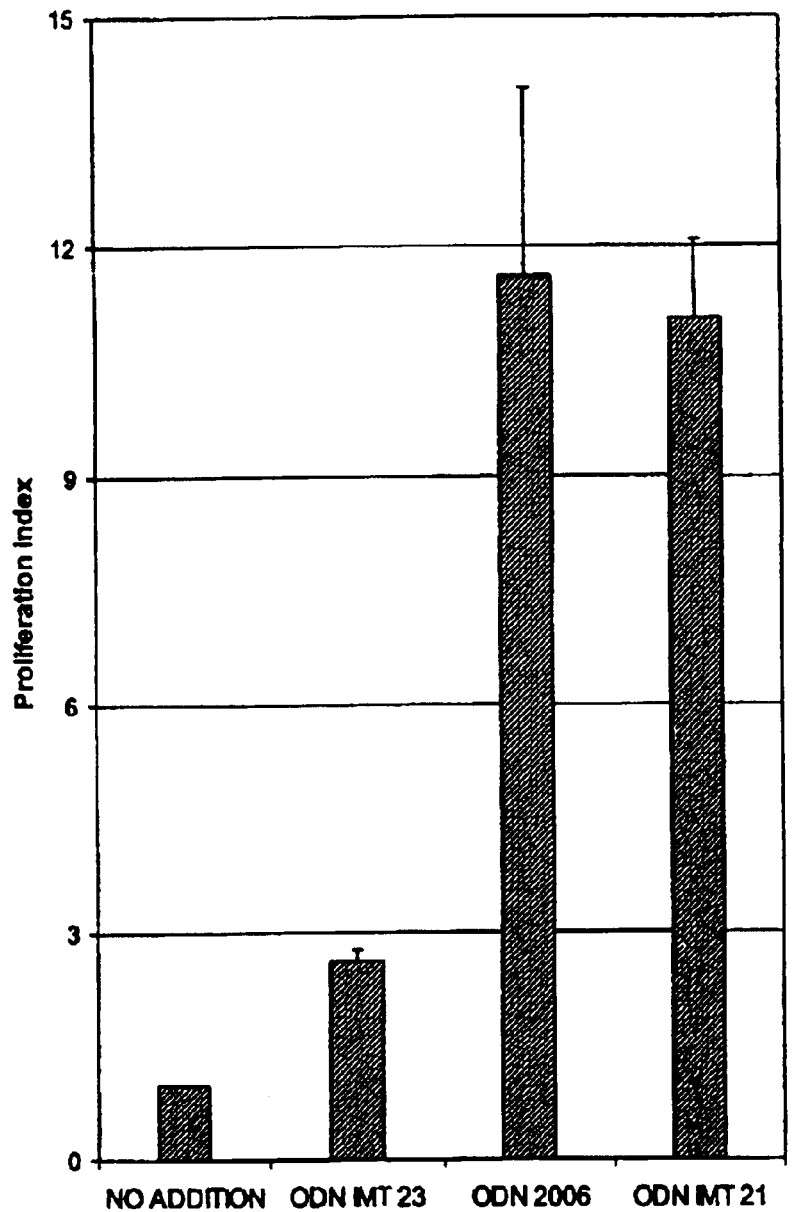
FIG. 1 is a graph plotting the proliferation index of human peripheral blood mononuclear leukocytes (PBMC) cultured with the phosphorothioate ODN IMT 023 (Seq. ID No 9), the phosphorothioate CpG ODN 2006.

FIG. 1 shows a proliferation assay performed with the above described oligonucleotides.

It was found, surprisingly, that the non CpG oligonucleotide IMT 021 was as active as the 2006 CpG oligonucleotide in proliferation assays (FIG. 1 and Table 1) if used at 1.5 mug/ml and approximately 40–60% active if used at 0.375 mug/ml.

TABLE 1

Induction of peripheral white blood cell proliferation by Phosphorothioate CpG (2006) and non-CpG oligonucleotides (IMT 021)

| | | PROLIFERATION INDEX | | | | | |
|---|---|---|---|---|---|---|---|
| | | (ODN at 1.5 μg/ml) | | | (ODN at 0.375 μg/ml) | | |
| ODN (S) | SEQUENCE (5'-3') | Avg. | N | SD | Avg. | N | SD |
| 2006 | TCGTCGTTTTGTCGTTTTGTCGTT | 17.95 | 4 | 2.39 | 13.83 | 14 | 1.55 |
| IMT 021 | TGCTGCTTTTGTGCTTTTGTGCTT | 17.41 | 5 | 2.74 | 8.02 | 15 | 1.21 |

MT 021 (SEQ. ID N° 1)
Avg.: Average; N: Number of Data; SD: Standard Deviation; ODN(S): phosphorothioate ODN Immunostimulation was also evaluated by Flow Cytometry using the CD 19 general marker for human B cells and the CD 86 activation marker for human B cells.

FIG. 2 shows the activation of human B cells incubated with the non CpG ODN (S) IMT 021 as compared to the activation induced by incubation with the CpG ODN (S) 2006. As can be observed, both ODNs show similar activation pattern as compared with the ODN(S) IMT 023 background control.

IL6 secretion was also evaluated in supernatants of PBMC incubated with the CpG ODN (S) 2006 and the non CpG ODN (S) IMT 021 (Table 2).

TABLE 2

Induction of human IL-6 secretion by phosphorothioate CpG and non-CpG oligonucleotides 2006 and IMT 021

| | IL-6 (pg/ml) | | | |
|---|---|---|---|---|
| ODN (S) | expt. 1 | expt. 2 | expt. 3 | expt. 4 |
| cells alone | 0 | 0 | 0 | 0 |
| 2006 | 568 | 159 | 597 | 374 |
| IMT 021 | 348 | 384 | 836 | 596 |

IMT 021 (SEQ. ID N° 1)

Results of this assay also indicate that the non-CpG ODN (S) IMT 021 is an effective immunostimulant. Therefore, other non-CpG sequence variants of the 2006 oligonucleotide were investigated. Table 3 shows the results for six of these variants in which the Cs or Gs of all the CpGs of this ODN were replaced by other nucleotides. As can be observed, the Gs of the CpGs in the ODN(S) 2006 are not necessary for B cell proliferation or IL6 secretion. However, modification of the Cs of the CpGs is detrimental if the replacement is for As or Gs but not if it is for Ts. These results clearly indicate that stimulation of the B cell proliferation and IL6 secretion by the ODN(S) 2006 is not at all associated with integrity of the CpG group.

The analysis of hundreds of ODNs (unshown) allowed definition of a core sequence (motif) responsible of the immunostimulatory activity as measured by B cell proliferation and IL6 secretion. This motif is the following:

$X_1X_2X_3X_4X_5X_6X_7X_8$, wherein $X_1$ is C,T,G or A (preferably T or C);
wherein $X_2$ is C,T,G or A;
wherein $X_7$ is C,T,G or A (preferably G);

TABLE 3

Induction of peripheral white blood cell proliferation and IL6 secretion by non-CpG variants of the ODN(S) 2006 oligonucleotide

| | | PROLIFERATION INDEX (ODN at 0.375 µg/ml) | | | IL-6 (pg/ml) (ODN at 6.0 µg/ml) | | |
|---|---|---|---|---|---|---|---|
| ODN (S) | SEQUENCE (5'-3') | Avg. | N | SD | Avg. | N | SD |
| 2006 | TCGTCGTTTTGTCGTTTTGTCGTT | 13.83 | 14 | 1.55 | 215.8 | 4 | 83.4 |
| IMT 504 | TCATCATTTTGTCATTTTGTCATT | 13.08 | 2 | 3.80 | 285.2 | 2 | 39.5 |
| IMT 505 | TCCTCCTTTTGTCCTTTTGTCCTT | 12.98 | 2 | 4.73 | 218.9 | 2 | 3.1 |
| IMT 506 | TCTTCTTTTGTCTTTTGTCTTT | 11.66 | 4 | 2.77 | 228.9 | 4 | 161.0 |
| IMT 501 | TAGTAGTTTTGTAGTTTTGTAGTT | 5.42 | 2 | 2.03 | 66.8 | 2 | 54.0 |
| IMT 502 | TGGTGGTTTTGTGGTTTTGTGGTT | 7.16 | 2 | 3.24 | 89.7 | 2 | 91.4 |
| IMT 503 | TTGTTGTTTTGTTGTTTTGTTGTT | 9.87 | 2 | 1.90 | 334.9 | 2 | 215.5 |

IMT 504 (SEQ ID N° 2); IMT 505 (SEQ ID N° 3); IMT 506 (SEQ ID N° 4); IMT 501 (SEQ ID N° 5); IMT 502 (SEQ ID N° 6); IMT 503 (SEQ ID N° 7)

EXAMPLE 3

Effect of Structure Modification on the Immunostimulatory Activity of Non-CpG Oligonucleotides: Definition of the Active Motif.

In order to study the influence of the primary structure on the immunostimulatory activity of the non-CpG ODNs, several variants of the 2006 and IMT 021 oligonucleotides were synthesized. Table 4 shows the primary structure of some of the IMT 021 variants and the results of a proliferation and IL-6 assays performed in order to evaluate its immunostimulatory activity.

The ODN(S) IMT 021 contains T in positions 7,8,9,10, 12,15,16,17,18,20,23 and 24. Replacement of these Ts with As (ODN IMT 022) or Cs (ODN IMT 023) results in a very significant loss of activity (about 76% and 75% respectively) in the proliferation assay and also in the IL-6 secretion assay (84% and 88% respectively). These results indicate that some or all the Ts in positions 7,8,9,10,12,15,16,17,18,20,23 and 24 are critical for the ODN IMT 021 immunostimulatory activity.

wherein at least three, and preferably all, of $X_3$, $X_4$, $X_5$, $X_6$ and $X_8$ are T.

Table 5 shows the effect of changes in each of the nucleotides of the two non-CpG motifs present in the ODN IMT 504 (motif: CATTTTGT). Replacement of the C in position 1 of the motif by A (ODN IMT 531) or G (ODN IMT 533) resulted in a loss of about 50% in the activity. However, replacement of this C by T (ODN IMT 532) does not change the activity. Thus, in order to obtain maximal activity the first position of the motif should be occupied by a pyrimidine nucleotide (C or T). In position 2, A (ODN IMT 504) or T (ODN IMT 535) or C (ODN IMT 534) are equivalent options.

In order to study the influence of a G nucleotide in position 2 of the motif without introduction of a CpG dinucleotide, ODNs with a T in the first position of the motif were synthesized (Table 6). As can be observed, any nucleotide in the second position of the immunostimulatory motif is equivalent.

Replacement of the G in position 7 of the immunostimulatory motif by A (ODN IMT 541), T (ODN IMT 542) or C (ODN IMT 543) is detrimental (Table 5). Thus, in order to obtain maximal activity position 7 should be preferably G.

TABLE 4

Induction of peripheral white blood cell proliferation and IL-6 secretion by Phosphorothioate non-CpG oligonucleotides derived from the inmunostimulatory IMT 021 oligonucleotide

| | | PROLIFERATION INDEX (ODN at 0.375 µg/ml) | | | IL-6 (pg/ml) (ODN at 6.0 µg/ml) | | |
|---|---|---|---|---|---|---|---|
| ODN (S) | SEQUENCE (5'-3') | Avg. | N | SD | Avg. | N | SD |
| IMT 021 | TGCTGCTTTTGTGCTTTTGTGCTT | 8.02 | 15 | 1.21 | 181.3 | 4 | 49.9 |
| IMT 022 | TGCTGCAAAAGAGCAAAAGAGCAA | 1.24 | 2 | 0.30 | 0.0 | 2 | 0.0 |
| IMT 023 | TGCTGCCCCCGCGCCCCCGCGCCC | 1.07 | 4 | 0.12 | 0.0 | 3 | 0.0 |

IMT 021 (SEQ. ID N° 1); IMT 022 (SEQ. ID N° 8); IMT 023 (SEQ. ID N° 9)

Regarding to the positions of the immunostimulatory motif occupied by Ts, the most sensitive (as measured by a change for an A) are 4 (ODN IMT 538), 5 (ODN ITM 539) and 8 (ODN IMT 544) and less sensitive are 3 (ODN IMT 537) and 6 (ODN IMT 540). Replacement of two or more of the Ts within the motif results in more than 70% loss of activity (ODNs IMT 545, IMT 546, IMT 547, IMT 548, IMT 549, IMT 550, IMT 551 and IMT 552). Therefore, in order to obtain a significant immunostimulatory activity three or more of positions 3,4,5,6 and 8 should be occupied by T.

different locations in a 24 nucleotides long poly T chain (FIG. 3). As can be seen, the poly T ODN (S) by itself has a significant mitogenic activity. On the other hand, introduction of only one CATTTTGT motif results in an increment of 1.2 to 1.8 times as measured by proliferation assays, or 2.4 to 3.5 times as measured by IL-6 secretion assays, in the immunostimulatory activity of the polyT chain depending on where the motif is located. A distance of at least two nucleotides from the 5' end or four from the 3' end seems to be necessary in order to reach maximal activity (ODNs

TABLE 5

Induction of peripheral white blood cell proliferation and IL-6 secretion by phosphorothioate non-CpG oligonucleotides of this invention derived from ODN IMT 504

| ODN (S) | SEQUENCE (5'-3') | PROLIFERATION INDEX (ODN at 0.375 µg/ml) | | | IL-6 (pg/ml) (ODN at 6.0 µg/ml) | | |
|---|---|---|---|---|---|---|---|
| | | Avg. | N | SD | Avg. | N | SD |
| IMT 022 | TGCTGCAAAAGAGCAAAAGAGCAA | 1.34 | 24 | 0.52 | 42.7 | 6 | 29.7 |
| IMT 504 | TCATCATTTTGTCATTTTGTCATT | 13.85 | 16 | 4.36 | 171.6 | 6 | 39.8 |
| IMT 531 | TCATAATTTTGTAATTTTGTCATT | 7.59 | 12 | 2.71 | 137.4 | 6 | 124.4 |
| IMT 532 | TCATTATTTTGTTATTTTGTCATT | 13.80 | 12 | 3.41 | 124.2 | 6 | 78.4 |
| IMT 533 | TCATGATTTTGTGATTTTGTCATT | 6.20 | 12 | 2.71 | 118.3 | 6 | 76.0 |
| IMT 534 | TCATCCTTTTGTCCTTTTGTCATT | 11.67 | 12 | 4.49 | 173.7 | 6 | 31.4 |
| IMT 535 | TCATCTTTTGTCTTTTGTCATT | 12.49 | 12 | 2.51 | 160.6 | 6 | 39.0 |
| IMT 537 | TCATCAATTGTCAATTTGTCATT | 10.17 | 12 | 4.00 | 183.5 | 6 | 63.6 |
| IMT 538 | TCATCATATTGTCATATTGTCATT | 7.12 | 12 | 2.95 | 133.2 | 6 | 86.7 |
| IMT 539 | TCATCATTATGTCATTATGTCATT | 9.80 | 12 | 4.22 | 171.7 | 6 | 53.4 |
| IMT 540 | TCATCATTAGTCATTTAGTCATT | 11.94 | 12 | 2.55 | 163.1 | 6 | 43.0 |
| IMT 541 | TCATCATTTTATCATTTTATCATT | 9.30 | 12 | 2.20 | 177.2 | 6 | 40.4 |
| IMT 542 | TCATCATTTTTCATTTTTCATT | 9.78 | 12 | 2.60 | 151.1 | 6 | 40.2 |
| IMT 543 | TCATCATTTTCTCATTTTCTCATT | 4.75 | 12 | 2.25 | 137.9 | 6 | 77.6 |
| IMT 544 | TCATCATTTTGACATTTTGACATT | 7.16 | 12 | 2.11 | 124.4 | 6 | 42.7 |
| IMT 545 | TCATCATTAGACATTTAGACATT | 4.19 | 12 | 1.81 | 129.4 | 6 | 53.8 |
| IMT 546 | TCATCATTATGACATTATGACATT | 2.90 | 12 | 1.16 | 105.0 | 6 | 67.2 |
| IMT 547 | TCATCATATTGACATATTGACATT | 3.34 | 12 | 1.16 | 110.3 | 6 | 43.5 |
| IMT 548 | TCATCATTAAGACATTAAGACATT | 3.40 | 12 | 1.53 | 91.5 | 6 | 33.1 |
| IMT 549 | TCATCATATAGACATATAGACATT | 3.51 | 12 | 1.03 | 121.3 | 6 | 41.3 |
| IMT 550 | TCATCATAATGACATAATGACATT | 1.91 | 12 | 0.71 | 79.3 | 6 | 30.8 |
| IMT 551 | TCATCATAAAGACATAAAGACATT | 2.17 | 12 | 0.72 | 60.7 | 6 | 26.4 |
| IMT 552 | TCATCAAAAAGACAAAAAGACATT | 1.37 | 12 | 0.83 | 21.6 | 6 | 13.5 |

IMT 022 (SEQ. ID N° 8); IMT 504 (SEQ ID N° 2); IMT 531 (SEQ ID N° 14); IMT 532 (SEQ ID N° 15); IMT 533 (SEQ ID N° 16); IMT 533 (SEQ ID N° 17); IMT 534 (SEQ ID N° 18); IMT 535 (SEQ ID N° 19); IMT 537 (SEQ ID N° 30); IMT 538 (SEQ ID N° 31); IMT 539 (SEQ ID N° 32); IMT 540 (SEQ ID N° 33); IMT 541 (SEQ ID N° 34); IMT 542 (SEQ ID N° 35); IMT 543 (SEQ ID N° 36); IMT 544 (SEQ ID N° 37); IMT 545 (SEQ ID N° 38); IMT 546 (SEQ ID N° 39); IMT 547 (SEQ ID N° 40); IMT 548 (SEQ ID N° 41); IMT 549 (SEQ ID N° 42); IMT 550 (SEQ ID N° 43); IMT 551 (SEQ ID N° 44); IMT 552 (SEQ ID N° 45)

TABLE 6

Induction of peripheric white blood cell proliferation and IL-6 secretion by Phosphorothioate non-CpG oligonucleotides with T in the first position of the immunostimulatory motif

| ODN (S) | SEQUENCE (5'-3') | PROLIFERATION INDEX (ODN at 0.375 µg/ml) | | | IL-6 (pg/ml) (ODN at 6.0 µg/ml) | | |
|---|---|---|---|---|---|---|---|
| | | Avg. | N | SD | Avg. | N | SD |
| IMT 532 | TCATTATTTTGTTATTTTGTCATT | 10.10 | 4 | 1.61 | 221.7 | 4 | 35.3 |
| IMT 197 | TCATTTTTTGTTTTTTGTCATT | 10.84 | 4 | 1.06 | 386.1 | 4 | 123.3 |
| IMT 198 | TCATTGTTTGTTGTTTTGTCATT | 10.00 | 4 | 1.75 | 235.3 | 4 | 27.1 |
| IMT 199 | TCATTCTTTGTTCTTTTGTCATT | 12.36 | 3 | 1.71 | 235.0 | 4 | 6.0 |

IMT 532 (SEQ ID N° 15); IMT 197 (SEQ. ID N° 10); IMT 198 (SEQ ID N° 11); IMT 199 (SEQ ID N° 12)

To investigate the effect of changes in the position of the motif within the ODN chain, the non-CpG motif CATTTTGT present in ODN IMT504 was introduced into IMT174 to IMT 179). Introduction of two motifs in optimal positions (ODN IMT182) results in an increment of 1.9 times as measured by proliferation assays, or 2.9 times as measured by IL-6 secretion assays, in the immunostimulatory activity of the polyT chain. This indicate that contribution of the second motif is negligible. On the other hand, the activity of the most effective ODNs like ODN IMT504 is more than 3 times larger than the activity of the poly T as measured by proliferation assays a fact that suggest that there is also a significant influence of the composition of at least some of the nucleotides surrounding the motif of this invention, in the overall activity of the ODN.

EXAMPLE 4
Effect of Structure Modification on the Immunostimulatory Activity of Non-CpG Oligonucleotides of this Invention: Influence of the Nucleotide Composition Outside of the Active Motif.

Results shown in FIG. 3 indicate that composition of the oligonucleotide outside the non-CpG core motif is important in order to reach optimal immunostimulatory activity.

Therefore, a number of oligonucleotides were synthesized with changes in the composition of the nucleotides surrounding the motifs. Table 7 shows the effect of changes in the composition of the first four nucleotides of the 5' end and of the last four nucleotides the 3' end in the immunostimulatory activity of ODN IMT 504. As can be observed, the best choices are: C or G in position −1 respect to the two motifs, C, T or G in position −2, any nucleotide in positions −3 and −4, A or T in position +1, G in position +2, any nucleotide in positions +3 and G is the best choice in position +4.

Of course, other nucleotide combinations not represented in this table may have equal or even better effect on the activity of the non CpG immunostimulatory oligonucleotides. One of ordinary skill in the art can empirically determine other effective combinations.

TABLE 7

Induction of peripheric white blood cell proliferation by non-CpG ODN(S) IMT 504 with variations in the composition outside the two immunostimulatory motifs

| ODN (S) | SEQUENCE (5'-3') | PROLIFERATION INDEX (ODN at 0.375 μg/ml) | | | IL-6 (pg/ml) (ODN at 6.0 μg/ml) | | |
|---|---|---|---|---|---|---|---|
| | | Avg. | N | SD | Avg. | N | SD |
| IMT 552 | TGCTGCAAAAGAGCAAAAGAGCAA | 1.9 | 12 | 0.7 | <39.9 | 4 | — |
| IMT 504 | TCATCATTTTGTCATTTTGTCATT | 11.0 | 8 | 0.9 | 171 | 2 | 14 |
| IMT 559 | ACATCATTTTGTCATTTTGTCATT | 13.4 | 4 | 1.0 | 128 | 3 | 3 |
| IMT 560 | CCATCATTTTGTCATTTTGTCATT | 12.1 | 4 | 0.9 | 145 | 4 | 32 |
| IMT 561 | GCATCATTTTGTCATTTTGTCATT | 9.5 | 4 | 1.1 | 209 | 4 | 74 |
| IMT 562 | TAATCATTTTGTCATTTTGTCATT | 12.4 | 4 | 1.5 | 171 | 4 | 24 |
| IMT 563 | TTATCATTTTGTCATTTTGTCATT | 11.1 | 3 | 0.7 | 172 | 4 | 63 |
| IMT 564 | TGATCATTTTGTCATTTTGTCATT | 12.8 | 4 | 0.9 | 118 | 4 | 38 |
| IMT 565 | TCCTCATTTTGTCATTTTGTCATT | 14.1 | 4 | 0.5 | 135 | 4 | 25 |
| IMT 566 | TCTTCATTTTGTCATTTTGTCATT | 13.9 | 4 | 2.2 | 157 | 4 | 28 |
| IMT 567 | TCGTCATTTTGTCATTTTGTCATT | 12.9 | 4 | 0.7 | 259 | 4 | 25 |
| IMT 568 | TCAACATTTTGTCATTTTGTCATT | 10.3 | 4 | 1.1 | 153 | 4 | 35 |
| IMT 569 | TCACCATTTTGTCATTTTGTCATT | 15.0 | 4 | 1.2 | 199 | 3 | 12 |
| IMT 570 | TCAGCATTTTGTCATTTTGTCATT | 12.5 | 4 | 0.4 | 181 | 3 | 2 |
| IMT 571 | TCATCATTTTGTCATTTTGTAATT | 14.2 | 4 | 0.7 | 163 | 4 | 26 |
| IMT 572 | TCATCATTTTGTCATTTTGTTATT | 13.2 | 4 | 1.4 | 182 | 3 | 67 |
| IMT 573 | TCATCATTTTGTCATTTTGTGATT | 8.7 | 4 | 0.7 | 177 | 4 | 29 |
| IMT 574 | TCATCATTTTGTCATTTTGTCCTT | 8.1 | 4 | 0.7 | 179 | 3 | 58 |
| IMT 575 | TCATCATTTTGTCATTTTGTCTTT | 10.8 | 4 | 0.8 | 150 | 3 | 47 |
| IMT 576 | TCATCATTTTGTCATTTTGTCGTT | 12.6 | 4 | 1.1 | 202 | 4 | 55 |
| IMT 577 | TCATCATTTTGTCATTTTGTCAAT | 10.0 | 4 | 1.4 | 243 | 3 | 8 |
| IMT 578 | TCATCATTTTGTCATTTTGTCACT | 10.9 | 4 | 0.9 | 213 | 2 | 9 |
| IMT 579 | TCATCATTTTGTCATTTTGTCAGT | 10.7 | 4 | 1.7 | 182 | 4 | 18 |
| IMT 580 | TCATCATTTTGTCATTTTGTCATA | 11.7 | 4 | 1.4 | 194 | 4 | 36 |
| IMT 581 | TCATCATTTTGTCATTTTGTCATC | 10.7 | 4 | 1.0 | 173 | 4 | 18 |
| IMT 582 | TCATCATTTTGTCATTTTGTCATG | 12.1 | 4 | 0.8 | 242 | 3 | 231 |

IMT 552 (SEQ. ID N° 45); IMT 504 (SEQ ID N° 2); IMT 559 (SEQ ID N° 46); IMT 560 (SEQ. ID N° 47); IMT 561 (SEQ ID N° 48); IMT 562 (SEQ ID N° 49); IMT 563 (SEQ ID N° 50); IMT 564 (SEQ ID N° 51); IMT 565 (SEQ ID N° 52); IMT 566 (SEQ ID N° 53); IMT 567 (SEQ ID N° 54); IMT 568 (SEQ ID N° 55); IMT 569 (SEQ ID N° 56); IMT 570 (SEQ ID N° 57); IMT 571 (SEQ ID N° 58); IMT 572 (SEQ ID N° 59); IMT 573 (SEQ ID N° 60); IMT 574 (SEQ ID N° 61); IMT 575 (SEQ ID N° 62); IMT 576 (SEQ ID N° 63); IMT 577 (SEQ ID N° 64); IMT 578 (SEQ ID N° 65); IMT 578 (SEQ ID N° 66); IMT 580 (SEQ ID N° 67); IMT 581 (SEQ ID N° 68); IMT 582 (SEQ ID N° 69)

EXAMPLE 5
Effect of Structure Modification on the Immunostimulatory Activity of Non-CpG Oligonucleotides of this Invention: Influence of the Size of the Oligonucleotide Table 8 shows that ODNs with one immunostimulatory motif are active if the chain is 16 or more nucleotides long. Activity is maximal if the ODN is 20 or more nucleotides long.

TABLE 8

Effect of the phosphorothioate non-CpG oligonucleotides size on B cells proliferation and IL6 secretion

| ODN (S) | SEQUENCE (5'-3') | PROLIFERATION INDEX (ODN at 0.375 µg/ml) | | | IL-6 (pg/ml) (ODN at 6.0 µg/ml) | | |
|---|---|---|---|---|---|---|---|
| | | Avg. | N | SD | Avg. | N | SD |
| IMT 187 | TTTTCATTTTGT | 0.56 | 8 | 0.20 | <50 | 4 | — |
| IMT 188 | TTTTCATTTTGTTTTT | 2.76 | 8 | 1.73 | 147 | 4 | 40 |
| IMT 189 | TTTTCATTTTGTTTTTTTTT | 8.21 | 8 | 3.19 | 227 | 4 | 21 |
| IMT 175 | TTTTCATTTTGTTTTTTTTTTTTT | 8.92 | 8 | 1.80 | 220 | 4 | 18 |
| IMT 179 | TTTTTTTTTTTTCATTTTGTTTTT | 6.06 | 8 | 2.00 | 224 | 4 | 82 |
| IMT 191 | TTTTCATTTTGTTTTTTTTTTTTTTTTT | 6.64 | 8 | 2.37 | 205 | 4 | 15 |

IMT 187 (SEQ ID N° 70); IMT 188 (SEQ ID N° 71); IMT 189 (SEQ ID N° 72); IMT 179 (SEQ ID N° 73); IMT 191 (SEQ ID N° 77)

EXAMPLE 6

Induction of Peripheric White Blood Cell IgM Secretion by Phosphorothioate Non-CpG Oligonucleotides of this Invention Induction of IgM secretion in peripheral white blood cells is another important marker of immunostimulatory activity of oligonucleotides. Table 9 shows the stimulation of IgM secretion by several of the phosphorothioate non-CpG oligonucleotides described above. As can be observed, the most active non-CpG ODN(S)s in induction of proliferation and IL6 secretion are also the best in induction of IgM secretion.

TABLE 9

Induction of peripheral white blood cell IgM secretion by phosphorothioate non-CpG oligonucleotides of this invention

| ODN (S) | SEQUENCE (5'-3') | IgM SECRETION (ng/ml) (ODN at 1.50 µg/ml) | | |
|---|---|---|---|---|
| | | Avg. | N | SD |
| cells alone | | 76 | 9 | 50 |
| 2006 | TCGTCGTTTTGTCGTTTTGTCGTT | 778 | 47 | 204 |
| IMT 021 | TGCTGCTTTTGTGCTTTTGTGCTT | 850 | 25 | 264 |
| IMT 501 | TAGTAGTTTTGTAGTTTTGTAGTT | 585 | 25 | 179 |
| IMT 502 | TGGTGGTTTTGTGGTTTTGTGGTT | 555 | 19 | 277 |
| IMT 503 | TTGTTGTTTTGTTGTTTTGTTGTT | 640 | 19 | 220 |
| IMT 504 | TCATCATTTTGTCATTTTGTCATT | 912 | 24 | 244 |
| IMT 505 | TCCTCCTTTTGTCCTTTTGTCCTT | 664 | 23 | 336 |
| IMT 506 | TCTTCTTTTTGTCTTTTTGTCTTT | 751 | 43 | 237 |
| IMT 509 | AAAAAACTAAAAAAAACTAAAAAA | 195 | 17 | 77 |

IMT 021 (SEQ. ID N° 1); IMT 504 (SEQ ID N° 2); IMT 505 (SEQ ID N° 3); IMT 506 (SEQ ID N° 4); IMT 501 (SEQ ID N° 5); IMT 502 (SEQ ID N° 6); IMT 503 (SEQ ID N° 7); IMT 509 (SEQ ID N° 13)

EXAMPLE 7

Stimulation of the Expression of CD40, MHC I and MHC II in B Lymphocytes by Phosphorothioate Non-CpG Oligonucleotides of this Invention As previously shown (FIG. 2), the non CpG ODN IMT 021 is able to stimulate the expression of CD86 on CD19+ cells (B lymphocytes). In order to extent this observation to other important cell surface markers, human PMBC were incubated with ODN IMT 504, ODN 2006 as a positive control and ODN IMT 022 as a negative control (FIG. 4). As can be observed, ODN IMT 504 is as active as the CpG ODN 2006 for stimulation of the expression of CD40, MHC I and MHC II on B lymphocytes.

EXAMPLE 8

Stimulation of Purified B Lymphocytes by Non-CpG Oligonucleotides of this Invention Human CD19+ (B) cells were purified to more than 95% purity. Table 10 and FIG. 5 shows that the immunostimulatory activity on this purified cells is comparable to the one observed using human PMBC. These results indicate that stimulation by the non-CpG oligonucleotides of this invention on human cells is direct.

TABLE 10

Induction of proliferation, IL6 and IgM secretion on purified B cells by phosphorothioate non-CpG oligonucleotides of this invention

| ODN (S) | SEQUENCE (5'-3') | Proliferation Index (ODN at 0.375 µg/ml) | | | IL-6 (pg/ml) (ODN at 6.0 µg/ml) | | | IgM (ng/ml) (ODN at 1.5 µg/ml) | | |
|---|---|---|---|---|---|---|---|---|---|---|
| | | Ave. | N | SD | Ave. | N | SD | Ave. | N | SD |
| IMT 022 | TGCTGCAAAAGAGCAAAAGAGCAA | 1.28 | 16 | 0.80 | 1019 | 5 | 665 | 469 | 7 | 182 |
| IMT 021 | TGCTGCTTTTGTGCTTTTGTGCTT | 24.48 | 16 | 5.16 | 9588 | 5 | 729 | 946 | 9 | 386 |
| IMT 504 | TCATCATTTTGTCATTTTGTCATT | 47.95 | 16 | 6.41 | 11002 | 5 | 884 | 1274 | 9 | 252 |
| IMT 506 | TCTTCTTTTTGTCTTTTTGTCTTT | 25.58 | 16 | 7.84 | 10933 | 3 | 1628 | 1083 | 10 | 430 |
| 2006 | TCGTCGTTTTGTCGTTTTGTCGTT | 60.82 | 24 | 9.79 | 7631 | 6 | 997 | 1292 | 12 | 245 |

IMT 021 (SEQ. ID N° 1); IMT 022 (SEQ. ID N° 8); IMT 504 (SEQ ID N° 2); IMT 506 (SEQ ID N° 4)

EXAMPLE 9

Immunostimulation by Phosphodiester Non-CpG Oligonucleotides of this Invention

FIG. 6 and Table 11 shows the effect of phosphodiester non-CpG oligonucleotides of this invention on human PMBC. Since phosphodiester oligonucleotides are very sensitive to nucleases they were added to the culture three times (0, 4, and 16 hs) to a final concentration of 30 µg/ml. A very potent phosphodiester CpG ODN (ODN 2080) was used as positive control in cytometric assays (Hartmann G, Weeratna R, Ballas Z K, Payette P, Suparto, I, Rasmussen W L, Wadschmidt M, Sajuthi D, Purcells R H, Davis H L, Krieg A M. Delineation of a CpG phosphorothioate oligodeoxynucleotide for activating primate immune responses in vitro and in vivo. J. Immunol.164, 1617–1624, (2000)). As can be observed, under these conditions phosphodiester ODNs bearing non CpG motifs of this invention have immunostimulatory activity.

TABLE 11

Immune-stimulation by phosphodiester non-CpG oligonucleotides of this invention

| ODN (S) | SEQUENCE (5'-3') | IL-6 Secretion (ng/ml) (ODN at 6.0 µg/ml) | | |
|---|---|---|---|---|
| | | Avg. | N | SD |
| IMT 022 | TGCTGCAAAAGAGCAAAAGAGCAA | 23 | 8 | 10 |
| IMT 053 | TTTTTTTTTTTTTTTTTTTTTTTT | 24 | 4 | 24 |
| IMT 504 | TCATCATTTTGTCATTTTGTCATT | 207 | 6 | 46 |
| IMT 506 | TCTTCTTTTTGTCTTTTTGTCTTT | 403 | 3 | 220 |
| 2006 | TCGTCGTTTTGTCGTTTTGTCGTT | 228 | 4 | 40 |

IMT 022 (SEQ. ID N° 8); IMT 504 (SEQ ID N° 2); IMT 053 (SEQ ID N° 19); IMT 506 (SEQ ID N° 4)

EXAMPLE 10

Induction of Cell Proliferation in Peripheral White Blood Cells of Monkeys of the Species *Cebus apella* and *Macaca fascicularis* by Non-CpG ODN(S)s of this Invention Non-CpG ODN(S)s of this invention are not very effective immunostimulants in mouse, pig and sheep. However, they are effective in monkeys. For example, FIG. 7 shows the immunostimulatory activity of non-CpG ODN(S)s on peripheral white blood cells of monkeys of the species *Cebus apella* and *Macaca fascicularis*. According to these results the most effective non-CpG ODNs in primates are those bearing the CATTTTGT motif. Therefore, monkeys can be used as animal models for research on clinical applications of these non-CpG ODN(S)s.

EXAMPLE 11

Vaccination of Subjects

Vaccine formulations containing the non-CpG ODNs adjuvant of this invention can be used to vaccinate subjects against a variety of bacterial and viral disease agents and against tumoral cells. Table 12 shows the effect of inoculation of monkeys of the species *Cebus apella* with a vaccine formulation that includes recombinant Hepatitis B surface antigen (rHBsAg) and alumina in presence or absence of ODN IMT 504 or ODN IMT 021 as adjuvant.

TABLE 12

Anti-HBs responses in Cebus apella immunized against HBsAg with IMT ODNs

| ODN (S) | Pre - prime | Post - prime | | Post - boost |
|---|---|---|---|---|
| | | 14 days | 28 days | 14 days |
| None | 0 | 0.4 ± 0.1 | 14 ± 20 | 190 ± 52 |
| IMT 021 | 0 | 23 ± 32 | 231 ± 287 | 902 ± 169 |
| IMT 504 | 0 | 10 ± 14 | 113 ± 114 | 659 ± 296 |
| 2006 | 0 | 22 ± 24 | 67 ± 57 | 705 ± 315 |

As can be observed there is a dramatic increment in the title of anti-HBsAg in animals vaccinated with HBsAg plus IMT ODN(S) 504 or 21 as compared with those vaccinated with HBsAg alone. CpG ODN 2006 have a performance as adjuvant similar to the non-CpG ODNs of this invention.

In particular, a human can be vaccinated against hepatitis B by administration of a vaccine formulation that includes recombinant Hepatitis B surface antigen (rHBsAg) and alumina and one or more of the oligonucleotides of this invention as adjuvants. The amount of rHBsAg in each dose, and the administration schedule, can vary as appropriate for the age of the human. For example, for humans from about birth to about 12 years old, a three dose schedule of from about 2.5 µg to about 5 µg of rHBsAg can be administered at 0, 1–3 months afterward and 4–18 months afterward, preferably at 0, 2 and 6 months. One or more of the oligonucleotides of this invention can be present in the formulation from about 10 µg to about 1,000 µg per dose.

For humans from about 12 to about 60 years old, a three dose schedule of from about 5 µg to about 40 µg of rHBsAg can be administered at 0, 1–3 months afterward and 4–18 months afterward, preferably at 0, 2 and 6 months. One or more of the oligonucleotides of this invention can be present in the formulation from about 10 µg to about 1,000 µg per dose.

EXAMPLE 12
Stimulation of the Expression of Costimulatory Molecules in Malignant B-Lymphocytes by Phosphorothioate Non-CpG Oligonucleotides The stimulation of malignant B lymphocytes recovered from blood of patients suffering chronic lymphocytic leukemia (CLL) by phosphorothioate non-CpG oligonucleotides of this invention was examined by flow cytometric (FACS) analysis. The results of a typical FACS analysis are shown in FIG. 8.

As can be seen the phosphorothioate non-CpG oligonucleotides IMT 021 and IMT 504 of this invention are able to stimulate expression of CD86, CD40 and MHC class I surface costimulatory molecules on malignant B lymphocytes as well as the CpG ODN 2006.

EXAMPLE 13

Stimulation of the Expression of Costimulatory Molecules on Plasmacytoid Dendritic Cells by Phosphorothioate Non-CpG Oligonucleotides of this Invention The stimulation of plasmacytoid dendritic cells recovered from blood of normal donors by phosphorothioate non-CpG oligonucleotides of this invention was examined by flow cytometric (FACS) analysis. The results of a typical FACS analysis are shown in FIG. 9. As can be seen the phosphorothioate non-CpG oligonucleotides IMT 021 and IMT 504 of this invention are able to stimulate expression of CD86, CD40 and MHC class I surface molecules on plasmacytoid dendritic cells as well as the CpG ODN 2006.

EXAMPLE 14

Treatment of Subjects with Tumoral Disease

Pharmaceutical formulations containing one or more of the oligonucleotides immunostimulatory of this invention, can be used to treat subjects against a variety of tumoral diseases. In particular, a human with a Melanoma can be treated by administration of a pharmaceutical formulation containing the oligonucleotide of this invention as the active component. The amount of oligonucleotide in each dose, and the administration schedule, can vary appropriate for the corporal mass of the subject and stage in tumor progression. For example, for a human of about 70 Kg. having an advance, unresectable metastatic melanoma, a dose of about 1 mg of the oligonucleotide of this invention can be administered 3 times per week during about 10 weeks.

What is claimed is:

1. An immunostimulatory oligonucleotide having 24 to 100 nucleotides, comprising the nucleotide sequence TCATCATTTTGTCATTTTGTCATT (SEQ ID No 2).

2. The immunostimulatory oligonucleotide of claim 1, wherein the immunostimulatory oligonucleotide is encapsulated in a slow release delivery vehicle.

3. The immunostimulatory oligonucleotide of claim 1, wherein the immunostimulatory oligonucleotide is included in a pharmaceutically acceptable carrier.

4. A pharmaceutical composition comprising an immunostimulatory oligonucleotide according to claim 1 and a pharmaceutically acceptable carrier.

5. A composition according to claim 4, wherein said immunostimulatory oligonucleotide is included in a plasmid.

6. A composition according to claim 4, further comprising an antigen.

7. A composition according to claim 6, wherein the antigen is selected from the group consisting of viruses, bacteria, fungi, parasites, tumor cells, toxins, allergens, proteins, glycolipids, and polysaccharides.

8. A composition according to claim 6, wherein the antigen is a viral antigen, a bacterial antigen, a human or animal tumor cell antigen, or a fungal antigen.

9. A composition according to claim 4, further comprising a plasmid encoding an antigen.

10. A composition according to claim 9, wherein the encoded antigen is a viral antigen, a bacterial antigen, a human or animal tumor cell antigen, or a fungal antigen.

11. An immunostimulatory oligonucleotide consisting of the nucleotide sequence
TCATCATTTTGTCATTTTGTCATT (SEQ ID No 2).

* * * * *